US008188115B2

(12) United States Patent
Torrens Jover et al.

(10) Patent No.: US 8,188,115 B2
(45) Date of Patent: *May 29, 2012

(54) 5-HT₇ RECEPTOR ANTAGONISTS

(75) Inventors: Antoni Torrens Jover, Barcelona (ES);
Josep Mas Prio, Barcelona (ES);
Susana Yenes Minguez, Barcelona (ES);
Mónica Garcia Lopez, Barcelona (ES);
Alberto Dordal Zueras, Barcelona (ES);
Luz Romero Alonso, Barcelona (ES);
Helmut Henrich Buschmann, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 721 days.

This patent is subject to a terminal disclaimer.

(21) Appl. No.: 11/658,924

(22) PCT Filed: Aug. 18, 2005

(86) PCT No.: PCT/EP2005/008978
§ 371 (c)(1),
(2), (4) Date: Dec. 19, 2008

(87) PCT Pub. No.: WO2006/018308
PCT Pub. Date: Feb. 23, 2006

(65) Prior Publication Data
US 2009/0163542 A1      Jun. 25, 2009

(30) Foreign Application Priority Data

Aug. 18, 2004 (EP) .................................. 04380171
Aug. 18, 2004 (ES) .................................. 200402049

(51) Int. Cl.
*C07D 217/18* (2006.01)
*A61K 31/47* (2006.01)

(52) U.S. Cl. .................. 514/307; 546/139; 546/147

(58) Field of Classification Search .................. None
See application file for complete search history.

(56) References Cited

U.S. PATENT DOCUMENTS
5,294,621 A    3/1994  Russell

FOREIGN PATENT DOCUMENTS
| EP | 0 021 580 | 12/1983 |
| EP | 0 076 072 | 5/1987 |
| WO | WO 97/29097 | 8/1997 |
| WO | WO 97/48681 | 12/1997 |
| WO | WO 97/49695 | 12/1997 |
| WO | WO 99/24022 | 5/1999 |
| WO | WO 00/00472 | 1/2000 |
| WO | WO 03/037887 | 5/2003 |
| WO | WO 03/048118 | 6/2003 |

OTHER PUBLICATIONS

Kitagawa et al, Biochimica et Biophysica Acta, 987(2), 1989, pp. 235-238.*
Terron, J. A., IDrugs, vol. 1(3), pp. 302-310, 1998.
Lovenberg et al., Neuron, vol. 11, pp. 449-458, 1993.
Terron, J. A., Br. J. Pharmacol., vol. 121, pp. 563-571, 1997.
Schoeffter et al., Br. J. Pharmacol., vol. 117, pp. 993-994, 1996.
Terron, J. A., Eur. J. Pharmacol., vol. 439, pp. 1-11, 2002.
De Ponti et al., Drugs, vol. 61, pp. 317-332, 2001.
Read et al., Br. J. Pharmacol., vol. 140, pp. 53-60, Jul. 29, 2003.
Wesolowska, A., Polish J. Pharmacol., vol. 54, pp. 327-341, 2002.
Mokrosz et al., J. Med. Chem., vol. 39, pp. 1125-1129, 1996.
Contreras et al., J. Med. Chem., vol. 42, pp. 730-741, 1999.
Alvarez et al., J. Med. Chem., vol. 30, pp. 1186-1193, 1987.
Alvarez et al., Anales Quimica, vol. 80, pp. 283-290, 1984.
Austin et al., Bioorg. Med. Chem. Lett., vol. 9, pp. 179-184, 1999.
Greene et al., Protective Groups in Organic Synthesis, 3rd Ed., John Wiley & Sons, Inc., pp. v, xi, xii, 1999.
Mach et al., Bioorg. Med. Chem. Lett., vol. 14(1), pp. 195-202, Jan. 5, 2004.
Munson et al., Anal Biochem., vol. 107, pp. 220-239, 1980.
Bon et al., J. Org. Chem., vol. 59, pp. 1904-1906, 1994.
Zhu et al., J. Med. Chem., vol. 46, pp. 831-837, Jan. 21, 2003.
Yamazaki et al., vol. 79, pp. 1014-1018, 1960, English Language Translation.
Yamazaki et al., Chemical Abstracts, vol. 54, Abstract 28777, 1960.
Vermeulen et al., J. Med. Chem., vol. 47, pp. 5451-5466, Sep. 2004.

* cited by examiner

*Primary Examiner* — Zinna Northington Davis
(74) *Attorney, Agent, or Firm* — Locke Lord LLP

(57)  ABSTRACT

The invention relates to compounds having pharmacological activity towards the 5-HT7 receptor, and more particularly to some tetrahydroisoquinoline substituted sulfonamide compounds, to processes of preparation of such compounds, to pharmaceutical compositions comprising them, and to their use for the treatment and or prophylaxis of a disease in which 5-HT is involved, such as CNS disorders.

10 Claims, No Drawings

5-HT$_7$ RECEPTOR ANTAGONISTS

This application is a national stage entry under 35 U.S.C. §371 of International Application No. PCT/EP2005/008978, filed Aug. 18, 2005, herein incorporated by reference in its entirety, which itself claims priority to Spanish Application No. P200402049 filed Aug. 18, 2004 and European Application 04380171.1 filed Aug. 18, 2004, each herein incorporated by reference in its entirety.

FIELD OF THE INVENTION

The present invention relates to compounds having pharmacological activity towards the 5-HT7 receptor, and more particularly to some tetrahydroisoquinoline substituted sulfonamide compounds, to processes of preparation of such compounds, to pharmaceutical compositions comprising them, and to their use in therapy, in particular for the treatment and or prophylaxis of a disease in which 5-HT$_7$ is involved, such as CNS disorders.

BACKGROUND OF THE INVENTION

The search for new therapeutic agents has been greatly aided in recent years by better understanding of the structure of proteins and other biomolecules associated with target diseases. One important class of proteins that has been the subject of extensive study is the family of 5-hydroxytryptamine (serotonin, 5-HT) receptors. The 5-HT$_7$ receptor discovered in 1993 belongs to this family and has attracted great interest as a valuable new drug target (Terrón, J. A. *Idrugs*, 1998, vol. 1, no. 3, pages 302-310: "*The* 5HT$_7$ *receptor: A target for novel therapeutic avenues?*").

5-HT$_7$ receptors have been cloned from rat, mouse, guinea pig and human cDNA and exhibit a high degree of interspecies homology (approx. 95%), but it is unique in that it has a low sequence homology with other 5-HT receptors (less than 40%). Its expression pattern, in particular structures of the central nervous system (CNS) (highest in hypothalamus (in particular suprachiasmatic nuclei) and thalamus) and other peripheral tissues (spleen, kidney, intestinal, heart and coronary artery), implicates the 5-HT$_7$ receptor in a variety of functions and pathologies. This idea is reinforced by the fact that several therapeutic agents, such as tricyclic antidepressants, typical and atypical antipsychotics and some 5-HT$_2$ receptor antagonists, display moderate to high affinity for both recombinant and functional 5-HT$_7$ receptors.

Functionally, the 5-HT$_7$ receptor has been implicated in regulation of circadian rhythms in mammals (Lovenberg, T. W. et al. *Neuron*, 1993, 11:449-458 "*A novel adnylyl cyclase-activating serotonin receptor* (5-HT$_7$) *implicated in the regulation of circadian rhythms*"). It is known that disruption of circadian rhythms is related to a number of CNS disorders including depression, seasonal affective disorder, sleep disorders, shift worker syndrome and jet lag among others.

Distribution and early pharmacological data also suggest that the 5-HT$_7$ receptor is involved in the vasodilatation of blood vessels. This has been demonstrated in vivo (Terrón, J. A., *Br J Pharmacol*, 1997, 121:563-571 "*Role of* 5-HT$_7$ *receptors in the long lasting hypotensive response induced by 5-hydroxytryptamine in the rat*"). Thus selective 5-HT$_7$ receptor agonists have a potential as novel hypertensive agents:

The 5-HT$_7$ receptor has also been related with the pathophysiology of migraine through smooth muscle relaxation of cerebral vessels (Schoeffter, P. et al., 1996, *Br J Pharmacol*, 117:993-994; Terrón, J. A., 2002, *Eur. J. Pharmacol.*, 439.1-11 "*Is the* 5-HT$_7$ *receptor involved in the pathogenesis and prophylactic treatment of migraine?*"). In a similar manner, involvement of 5-HT$_7$ in intestinal and colon tissue smooth muscle relaxation makes this receptor a target for the treatment of irritable bowel syndrome (De Ponti, F. et al., 2001, *Drugs*, 61:317-332 "*Irritable bowel syndrome. New agents targeting serotonin receptor subtypes*"). Recently, it has also been related to urinary incontinence (*British J of Pharmacology*, September 2003, 140(1) 53-60: "Evidence for the involvement of central 5HT-7 receptors in the micurition reflex in anaesthetized female rats").

In view of the potential therapeutic applications of agonists or antagonists of the 5HT$_7$ receptor, a great effort has been directed to find selective ligands. Despite intense research efforts in this area, very few compounds with selective 5-HT$_7$ antagonist activity have been reported (Wesolowska, A., *Polish J. Pharmacol.*, 2002, 54:327-341, "*In the search for selective ligands of* 5-HT$_5$, 5-HT$_6$ *and* 5-HT$_7$ *serotonin receptors*").

WO 97/48681 discloses sulfonamide derivatives, which are 5-HT$_7$ receptor antagonists, for the treatment of CNS disorders. The sulphur atom is linked to an aromatic group and to a N-containing heterocyclic group, optionally containing a further heteroatom selected from oxygen or sulphur.

WO 97/29097 describes sulfonamide derivatives for the treatment of disorders in which antagonism of the 5-HT$_7$ receptor is beneficial. The sulphur atom is linked to an aromatic group and to a $C_1$-$C_6$ alkyl substituted N atom.

WO97/49695 describes further sulfonamide derivatives in which the N linked to the sulphur atom is also fully substituted, for example forming part of a piperidine.

WO 03/048118 describes another group of 5HT$_7$ receptor antagonists. In this case aryl and heteroaryl sulfonamide derivatives wherein the sulfonamide group is a substituent on a cycloalkane or cycloalkene ring which additionally bears an amino substituent. The N linked to sulphur atom is fully substituted.

WO99/24022 discloses tetrahydroisoquinoline derivatives for use against CNS disorders and binding to serotonin receptors, in particular 5-HT$_7$.

WO 00/00472 refers to compounds which are 5-HT7 receptor antagonists. The compounds contain a N-containing fused heterocycle such as tetrahydroisoquinoline.

EP 21580 and EP 76072 describe sulfonamide compounds having antiarrhythmic activity, corresponding to the formula $R_2N(CH_2)_n$—NH—$SO_2R_1$, 5-HT$_7$ activity is not mentioned.

There is still a need to find compounds that have pharmacological activity towards the receptor 5-HT$_7$, being both effective and selective, and having good "drugability" properties, i.e. good pharmaceutical properties related to administration, distribution, metabolism and excretion.

SUMMARY OF THE INVENTION

We have now found a family of structurally distinct class of sulfonamide compounds which are particularly selective inhibitors of the 5-HT$_7$ receptor. The compounds present a tetrahydroisoquinoline moiety, linked through a straight alkylene chain of a certain size with a sulfonamide moiety. We have found that when the N of the sulfonamide is a secondary amine and the linker has 4, 5 or 6 —$CH_2$— units the compounds display IC-50 values in the nM range (>10 nM) at human 5-HT7 receptors and exhibit at least 30-fold selectivity for these receptors vs 5-HT1A, 5-HT2A, 5-HT2B, 5-HT2C, 5-HT3, 5-HT4, 5-HT5A, D1, D2, D3, D4, adrenergic α1A, α1B, α1B, β1, and β2 receptors.

In one aspect the invention is directed to a compound of the formula I:

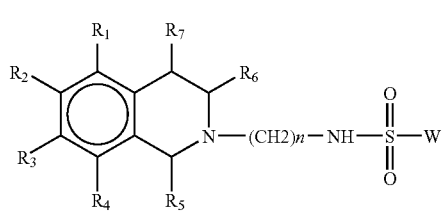

wherein
W is a substituted or unsubstituted alkyl, substituted or unsubstituted alkenyl, substituted or unsubstituted cycloalkyl, substituted or unsubstituted aryl, substituted or unsubstituted heterocyclyl;
$R_1$, $R_2$, $R_3$, $R_4$, $R_5$, $R_6$ and $R_7$ are each independently selected from the group formed by hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_8$, —$C(O)OR_8$, —$C(O)NR_8R_9$, —C=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$ or halogen, wherein t is 1, 2 or 3;
$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen;
n is 4, 5 or 6;
or a pharmaceutically acceptable salt, isomer, prodrug or solvate thereof.
In one embodiment n is preferably 4 or 5, most preferably n is 4.

It is preferred that W is substituted or unsubstituted aryl, substituted or unsubstituted heterocyclyl, preferably substituted or unsubstituted phenyl. Good results were obtained when W is alkyl or halo substituted phenyl.

It is preferred that in the tetrahydrosioquinoline moiety $R_5$, $R_6$ and $R_7$ are H.

In one embodiment $R_1$ and $R_4$ are also H.

Good results are obtained when $R_2$ and $R_3$ are alkoxy, in particular methoxy.

In another aspect the invention is directed to a pharmaceutical composition which comprises a compound as above defined or a pharmaceutically acceptable salt, enantiomer, prodrug or solvate thereof, and a pharmaceutically acceptable carrier, adjuvant or vehicle.

In a further aspect the invention is directed to the use of a compound as defined above in the manufacture of a medicament for the treatment of a 5-$HT_7$ mediated disease or condition, i.e. diseases caused by failures in central and peripheral serotonin-controlling functions, such as pain, sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

DETAILED DESCRIPTION OF THE INVENTION

The typical compounds of this invention effectively and selectively inhibit the 5-HT7 receptor without inhibition of other 5-HT receptors such as 5-HT1A, 5-HT2A, 5-HT2B, 5-HT2C, 5-HT3, 5-HT4, 5-HT5A, D1, D2, D3, D4, adrenergic α1A, α1B, α1B, β1, and β2 receptors, Tachykinin NK-1 opiate, GABA, estrogen, glutamate, adenosine, nicotinic, muscarinic receptors and calcium, potassium and sodium channels and neurotransmitter transporters (serotonin, dopamine, norepinephrine, GABA).

In the above definition of compounds of formula (I) the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2 C atoms and having one or more unsaturated bonds.

"Cycloalkyl" refers to a stable 3-to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3-to 15 membered ring radical which consists of carbon atoms and from one to five heteroatoms selected from the group consisting of nitrogen, oxygen, and sulfur, preferably a 4-to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —ORa where Ra is an alkyl radical as defined above, e.g., methoxy, ethoxy, propoxy, etc.

"Alkoxycarbonyl" refers to a radical of the formula —C(O)ORa where Ra is an alkyl radical as defined above, e.g., methoxycarbonyl, ethoxycarbonyl, propoxycarbonyl, etc.

"Alkylthio" refers to a radical of the formula —SRa where Ra is an alkyl radical as defined above, e.g., methylthio, ethylthio, propylthio, etc.

"Amino" refers to a radical of the formula —NH2, —NHRa or —NRaRb, optionally quaternized.

"Halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Particular individual compounds of the invention include the compounds 1-338 in the examples, either as salts or as free bases.

In an embodiment the tetrahydroisoquinoline in the compounds of formula I above is not substituted, $R_1$ to $R_7$ are all H. Good activity results are obtained with such compounds.

In another embodiment $R_2$ and $R_3$ are alkoxy, preferably methoxy and the rest of the substituents of the tetrahydroisoquinoline ($R_1$ and $R_4$ to $R_7$) are H. In this case it appears that the selectivity is improved.

In another embodiment the group W linked to the sulfonamide is aromatic, such as substituted or unsubstituted aryl, substituted or unsubstituted heterocyclyl, preferably substituted or unsubstituted phenyl. Good results were obtained when W is alkyl, alkoxy or halo substituted phenyl. In particular halo substituted phenyl, having one or more halo substituents being the same or different are preferred.

In another embodiment it is important that n is 4, best results were obtained with this length of the chain linking the tetrahydroisoquinoline and the sulfonamide.

The above embodiments and preferences for W, $R_1$ to $R_7$ and n can be combined to give further preferred compounds.

Representative compounds of the above embodiments which are preferred are Naphthalene-2-sulfonic acid [4-(3,4-dihydro-1H-isoquinolin-2-yl)-butyl]-amide hydrochloride; N-[4-(3,4-Dihydro-1H-isoquinolin-2-yl)-butyl]-benzenesulfonamide hydrochloride; 5-Chloro-N-[4-(6,7-dimethoxy-3,4-dihydro-1H-isoquinolin-2-yl)-butyl]-2,4-difluoro-benzenesulfonamide; 2-Chloro-N-[4-(6,7-dimethoxy-3,4-dihydro-1H-isoquinolin-2-yl)-butyl]-benzenesulfonamide hydrochloride; N-[4-(3,4-Dihydro-1H-isoquinolin-2-yl)-butyl]-2,5-difluoro-benzenesulfonamide hydrochloride; N-[4-(3,4-Dihydro-1H-isoquinolin-2-yl)-butyl]-2,4,5-trifluoro-benzenesulfonamide hydrochloride; 2-Chloro-N-[4-(6,7-dimethoxy-3,4-dihydro-1H-isoquinolin-2-yl)-butyl]-4,5-difluoro-benzenesulfonamide hydrochloride; 2-Bromo-N-[4-(3,4-dihydro-1H-isoquinolin-2-yl)-butyl]-4,6-difluoro-benzenesulfonamide hydrochloride; N-[4-(6,7-Dimethoxy-3,4-dihydro-1H-isoquinolin-2-yl)-butyl]-3-methyl-benzenesulfonamide hydrochloride; 4-Chloro-N-[4-(6,7-dimethoxy-3,4-dihydro-1H-isoquinolin-2-yl)-butyl]-2,5-dimethyl-benzenesulfonamide hydrochloride; N-[4-(6,7-Dimethoxy-3,4-dihydro-1H-isoquinolin-2-yl)-butyl]-2,5-dimethoxy-benzenesulfonamide hydrochloride or 2-Bromo-N-[4-(6,7-dimethoxy-3,4-dihydro-1H-isoquinolin-2-yl)-butyl]-benzenesulfonamide hydrochloride. Although the hydrochloride salts are listed, other salts or the free bases also form part of this group of preferred compounds.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C— or 14C-enriched carbon or $^{15}$N-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds of formula (I) defined above can be obtained by available synthetic procedures. For example, they can be prepared by the coupling of a compound of Formula (II):

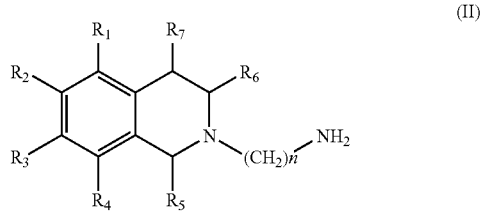

(II)

in which R1-R7 and n are as defined in Formula (I), with a compound of Formula (III):

(III)

in which W is as defined in Formula (I) and X is an halogen, typically Cl.

The reaction of compounds of formulas (II) and (III) is preferably carried out in an aprotic solvent, but not limited to, such as dichloromethane in the presence of an organic base, such as diisopropylethylamine or triethylamine.

Compounds of Formula (III) are commercially available or can be prepared by conventional methods.

Compounds of Formula (II) can be prepared from compounds of Formula (IV) using the reactions and techniques described below. Compounds of Formula (IV) are commercially available or may be prepared according to known methods.

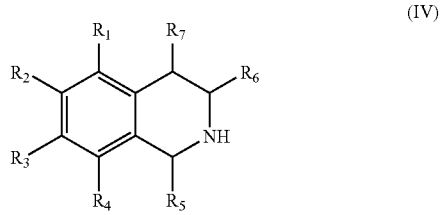

(IV)

The reactions are performed in a solvent appropriate to the reagents and materials employed and suitable for the transformations. The functionality present on the molecule should be consistent with the transformations proposed. This will sometimes require a selection of a particular process scheme over another in order to obtain the desired compound of the invention. Preferred methods included, but are not limited to, those described below. References for cited described methods are incorporated.

Compounds of Formula (II) can be prepared by alkylation as shown in Scheme 1.

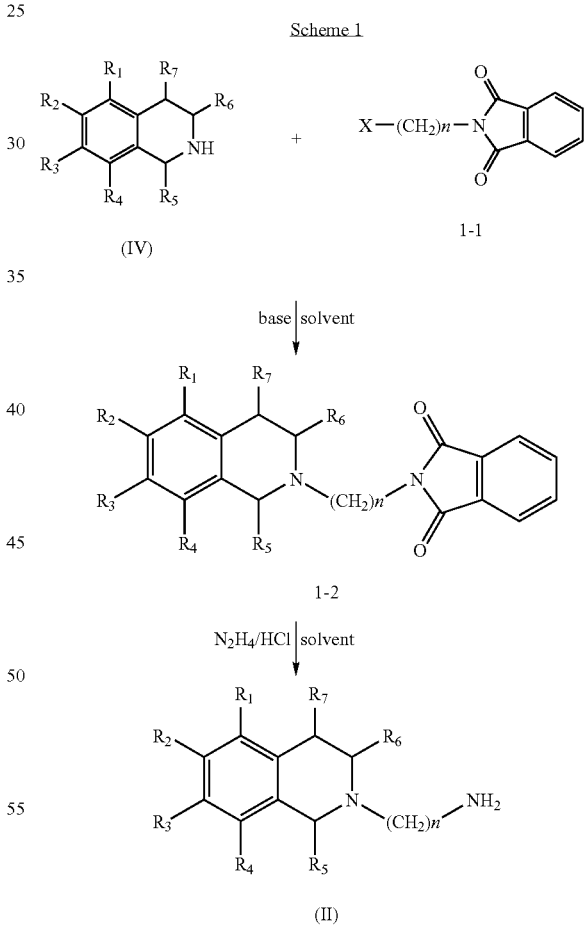

In the first step, the amine of Formula (IV) is allowed to react with a commercially available N-(n-haloalkyl)phtalimide (1-1) in the presence of an appropriate base and solvent. Useful bases include, but are not limited to, metal carbonates such as $K_2CO_3$ or $Cs_2CO_3$, metal hydroxides, hindered alkoxides or tertiary organic amines.

Typical solvents include polar aprotic liquids such as DMF or THF, or protic liquids such as alcohols. The use of buthanol or xylene have been previously described (*J. Med. Chem.* 1996, 39(5), 1125-1129, *J. Med. Chem.* 1999, 42(4), 730-741) but the yield is improved, (from 50% to 90%), with the use of N,N-dimethylformamide and $K_2CO_3$ as the base.

In a second step, the hydrazinolysis of the alkylated compound 1-2 using hydrazine in a polar protic solvent, such as ethanol, and hydrochloric acid gives the desired compound of Formula (II).

A similar route to compounds of Formula (II) is illustrated in Scheme 2.

as N,N-diisopropylethylamine, triethylamine, etc. The activated species are usually not isolated, but are allowed to react in situ with the amine partner (IV).

After the hydrazinolysis of phtalimide 2-2, the reduction of the amide intermediate 2-3 may be performed with a reducing agent, such as borane or lithium aluminum hydride in appropriate solvent, typically THF (*J. Med. Chem.* 1987, 30, 1186-1193, *Anales Quimica,* 1983, 80, 283-290).

A similar method to compounds of Formula (II) is illustrated in Scheme 3.

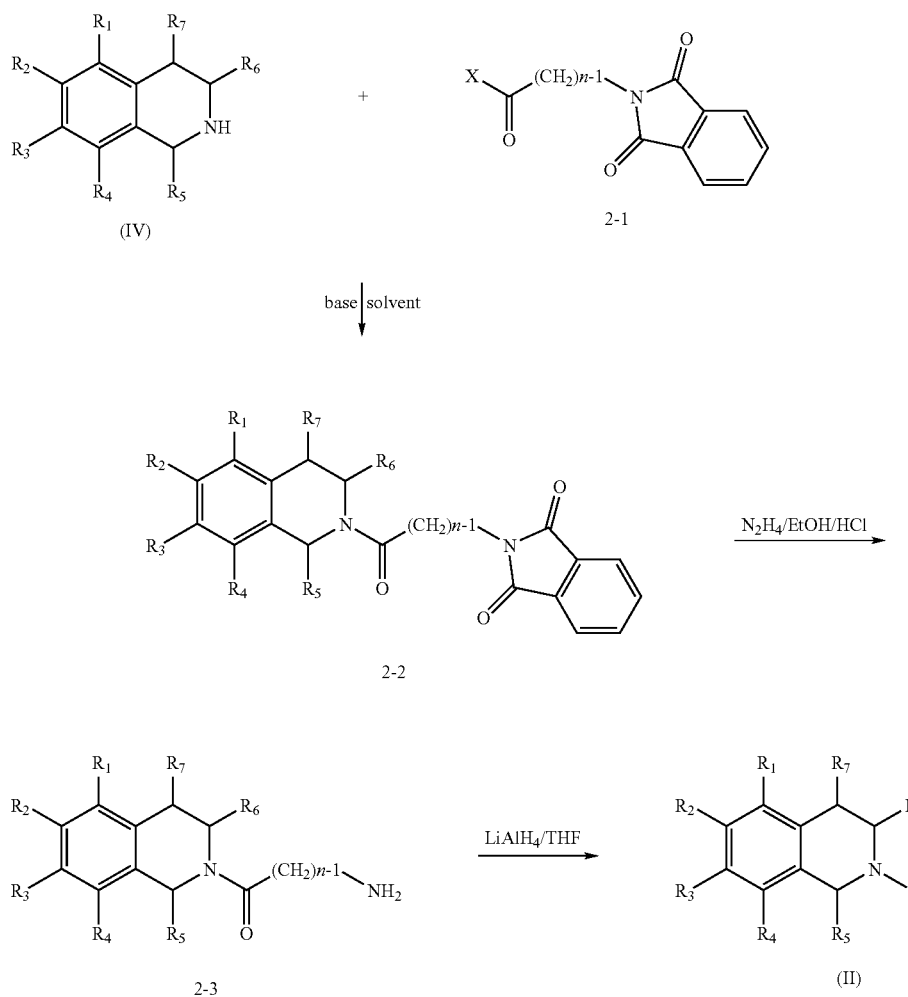

The acylation of compounds of Formula (IV) with carboxyalkylphtalimides derivatives (2-1), instead of the alkylation with N-(n-haloalkyl)phthalimides (1-1), may be convenient in some cases. When X is a Cl, the base used for acylation could be a tertiary organic amine such as triethylamine or N,N-diisopropylethylamine and the hydrazinolysis can be performed as cited in Scheme 1. When X is an OH, a coupling reagent must be used for the activation of carboxy group. Many coupling reagents are known in the literature to form amide bonds from carboxylic acids and amines, including DCC, HBTU, TBTU, BOP, PyBOP, etc. Appropriate bases for such coupling reactions include tertiary amines such

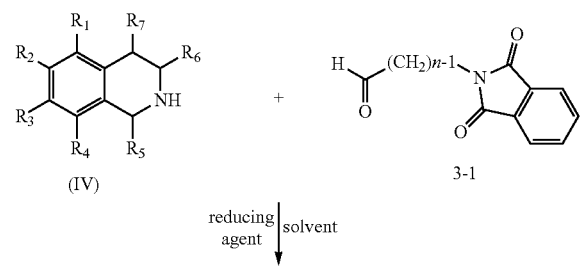

-continued

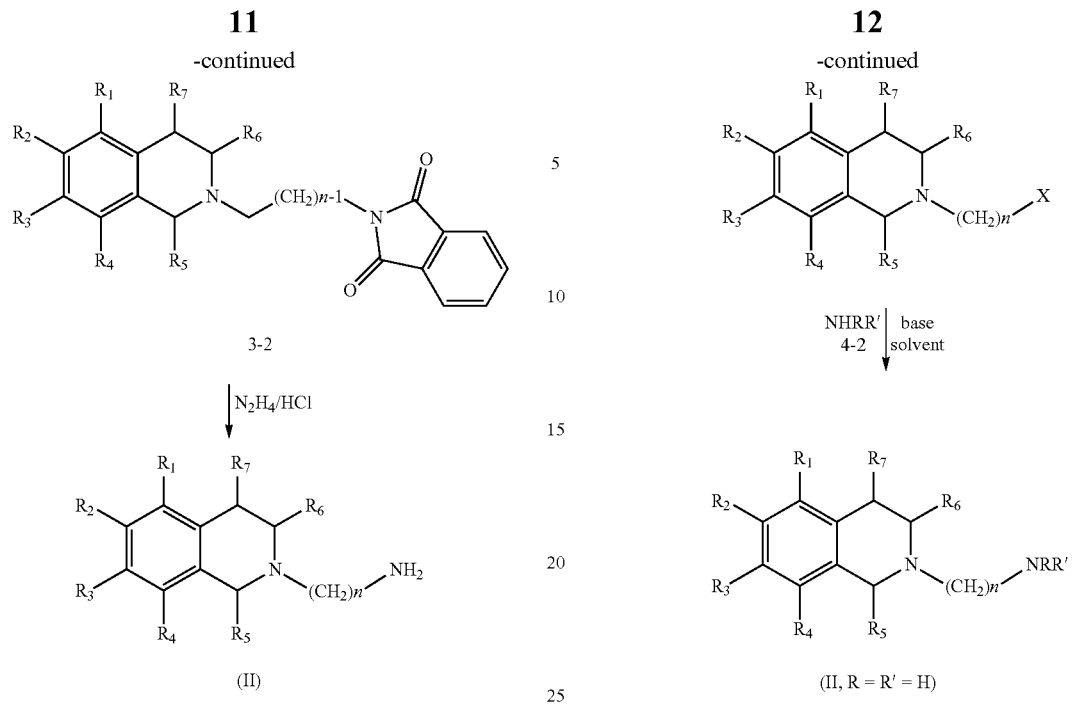

A reductive amination with phtalimidoalkylaldehydes (3-1), following by hydrazinolysis may also be performed. Condensation of the amine (IV) with aldehydes 3-1 can be performed in the presence of an hydride, such as sodium triacetoxyborohydride NaBH(OAc)$_3$ or sodium cyanoborohydride (NaBH$_4$CN) (*Bioorg. Med. Chem. Lett.* 1999, 9, 179-184). Phtalimide intermediate 3-2 is treated as is described in Schemes 1 and 2 in order to obtain the desired compound of Formula (II).

In all these Schemes, other protecting groups for the nitrogen atom, instead of the phtalimide, may be used. Some examples include other cyclic imide derivatives, such as maleimides or succinimides, a variety of carbamates, such as BOC; Fmoc, etc. a variety of amides, such as acetainides, and alkyl and aryl amine derivatives, such as N-benzyl or N-allyl. Additional examples of Nitrogen protecting groups can be found in reference books such as Greene and Wuts' "Protective Groups in Organic Synthesis", John Wiley & Sons, Inc., New York, 1999.

An alternate sequence for the preparation of some compounds of Formula (II) is illustrated in Scheme 4.

Compounds of Formula (II) can be prepared in a sequential way by treatment of a dialkylating agent (4-1) with the corresponding amine (IV) in the presence of a base in an appropriate solvent, followed by the alkylation of another amine (4-2).

Examples of useful alkylating agents (4-1) are those where Y is a good to excellent leaving group, such as Br, I, aryl or alkylsulfonate, etc. and X is a good leaving group, such as Br or Cl. Useful bases include, but are not limited to, metal carbonates such as K$_2$CO$_3$ or Cs$_2$CO$_3$, metal hydroxides, hindered alkoxides or tertiary organic amines.

Typical solvents include polar aprotic liquids such as DMF or THF, or protic liquids such as alcohols. The rate of the second alkylation may be enhanced, particularly when X is Cl, by the addition of a catalytic amount of an iodide salt, such as NaI or KI. The required alkylating agents (4-1) are generally commercially available.

Where convenient, compounds of Formula (II) can be prepared as shown in Scheme 5.

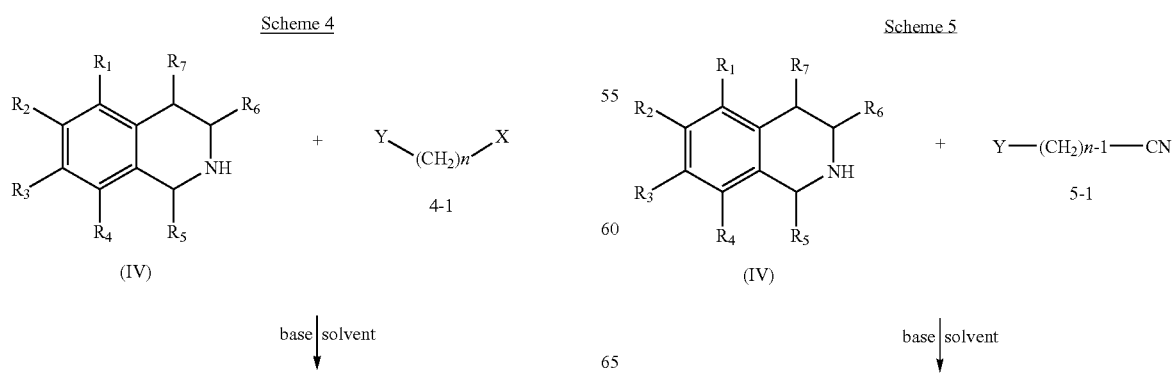

-continued

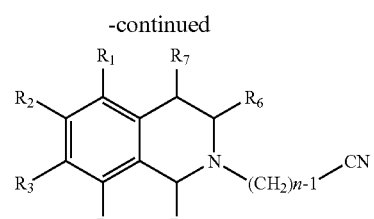

5-2 reducing agent | base solvent

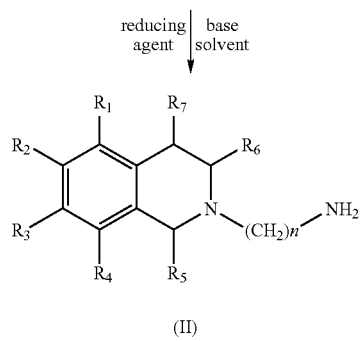

(II)

The alkylation of compounds of Formula (IV) with commercially available haloalkylnitriles (5-1) can be performed in the presence of a variety of bases and solvents cited in schemes above. For the reduction of the cyano group of 5-2, common reducing agents, such as LiAlH$_4$ in THF, can be used. A catalytic hydrogenation with Pd/C in ethanol is also possible (*Bioorg. Med. Chem. Lett.* 2004, 14, 195-202, *J. Med. Chem.* 1999, 42(4), 730-741).

In some cases, an acylation with carboxynitriles to form an amide is preferred instead of the alkylation with the corresponding haloalkylnitriles (Scheme 6).

Scheme 6

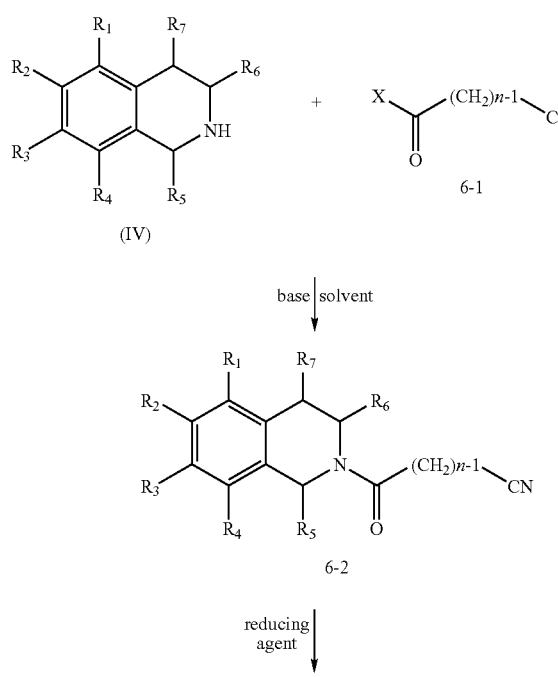

-continued

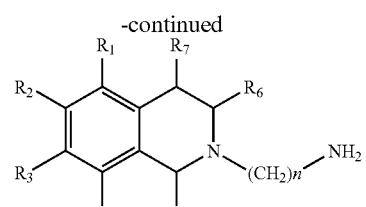

(II)

The acylation with compounds 6-1, where X is a good leaving group, such as I, Br, aryl or alkylsulphonate, is carried out in the presence of an appropriate base and solvent, which were described in schemes above. The reduction of cyano an keto group of 6-2 can be performed simultaneously in the presence of an excess of a reducing agent such as LiAlH$_4$ or borane. When X is OH, a coupling reagent must also be used for the activation of carboxy group. The coupling reagents used are the same as are cited in Scheme 2.

Scheme 6 is also possible when X is an H. Reductive amination is carried out by a condensation of amine of Formula (IV) with aldehyde 6-1 in appropriate base and solvent, to form an imine or enamine intermediate, followed by a reduction with a reducing agent, such as an hydride.

An alternate sequence for the preparation of some compounds of Formula (II) is illustrated in Scheme 7.

Scheme 7

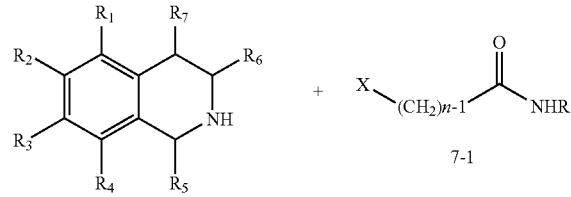

7-1 base | solvent

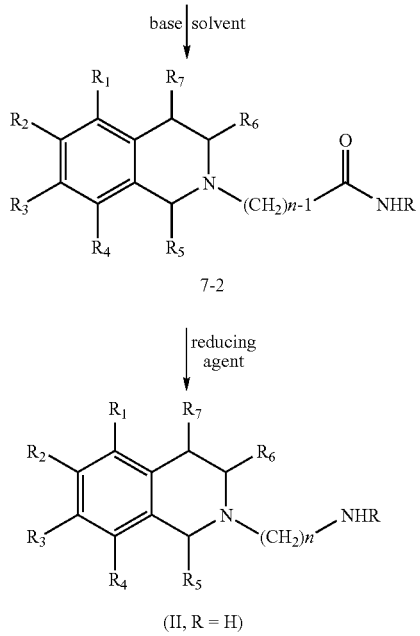

Amines of Formula (IV) may be alkylated with haloalkylamides 7-1 in an appropriate solvent and base, the same as are cited in Schemes above. Intermediate (7-2) may be reduced in the presence of an hydride, such as $LiAlH_4$ or borane.

The obtained reaction products may, if desired, be purified by conventional methods, such as crystallisation, chromatography and trituration. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing an 5-$HT_7$ mediated disease which method comprises administering to a patient in need of such a treatment a therapeutically effective amount of a compound of formula (I) or a pharmaceutical composition thereof. Among the 5-$HT_7$ mediated diseases that can be treated are diseases caused by failures in central and peripheral serotonin-controlling functions, such as pain, sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

The starting materials of general formula (II) were prepared by means of conventional organic chemistry methods known to those skilled in the art. The preparation of some of the intermediates of general formulas (II) and (IV) is shown below:

Example A

The starting materials of general formulas (IV) were prepared by means of conventional organic chemistry methods known to those skilled in the art.
Synthesis of a Compound of General Formula (IV)
7-Nitro-1,2,3,4-tetrahydroisoquinoline Hydrochloride.
This compound is described in the literature for Buolamwini et al. *J. Med. Chem.* 2003, 46, 831-837, which are hereby incorporated by reference and form part of the disclosure.

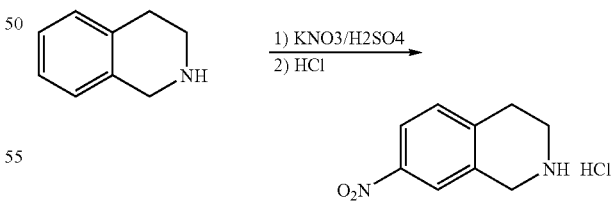

A cold solution of 1,2,3,4-tetrahydroisoquinoline (13.3 g, 0.1 mol) in concentrated sulfuric acid (50 mL) was treated with potassium nitrate (11.12 g, 1.1 mol) in small portions, keeping the temperature below 5° C. The reaction was left overnight at room temperature and poured onto ice. The resulting solution was basified with ammonium hydroxide, extracted with $CH_2Cl_2$, dried and evaporated to dryness in vacuo. The crude was dissolved in 100 mL ethanol. A 2.8 M solution of hydrogen chloride in ethanol (40 mL) was then added. The precipitate formed was collected by filtration and crystallized from methanol to give the product (10.30 g, 48% yield) as a white solid.
Melting point: 268-270° C.
IR cm$^{-1}$(KBr):2944,2764, 1589, 1523, 1429, 1345, 1090.
$^1$H NMR (300 MHz, DMSO-d6) d ppm: 3.13 (t, J=6.15 Hz, 2H), 3.35 (t, J=6.22 Hz, 2H), 4.35 (s, 2H), 7.50 (d, J=8.49 Hz, 1H), 8.08 (dd, J=8.49, 2.49 Hz, 1H), 8.19 (d, J=2.34 Hz, 1H), 9.96 (s, 2H)

Example B

Synthesis of a Compound of General Formula (II)

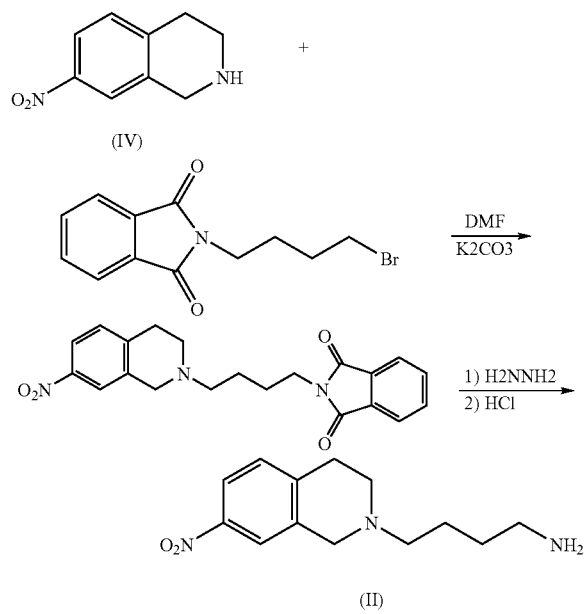

a) 2-(4-N-phtalimidobutyl)-7-nitro-1,2,3,4-tetrahydroisoquinoline

A mixture of 7-nitro-1,2,3,4-tetrahydroisoquinoline hydrochloride (9.87 g, 0.046 mol), N-(4-Bromobutyl)phtalimide (12.97 g, 0.046 mol), potassium carbonate (25.43 g, 0.184 mol) in dry N,N-dimethylformamide (150 mL), was stirred overnight at room temperature. The mixture was vacuum concentrated and the residue was dissolved in water (150 mL) and extracted with ethyl acetate (3×50 mL), washed with water, the organic layer was dried and evaporated to give the product (16.58 g, 95% yield) which was used without further purification.
1H NMR (300 MHz, DMSO-D6) d ppm 1.64 (m, 2H), 1.79 (m, 2H), 2.60 (m, 2H), 2.78 (m, 2H), 2.96 (m, 2H), 3.72 (m, 4H), 7.23 (m, 1H), 7.71 (m, 2H), 7.79 (m, 3H), 8.01 (m, 1H)

b) 2-(4-aminobutyl)-7-nitro-1,2,3,4-tetrahydroisoquinoline Dihydrochloride

A solution of 2-(4-N-Phtalimidobutyl)-7-nitro-1,2,3,4-tetrahydroisoquinoline (16.30 g, 0.043 mol) and hydrazine hydrate (13.4 mL, 0.43 mol) in ethanol (350 mL) was refluxed for 1 h. The reaction mixture was cooled down and treated with an additional amount of ethanol (350 mL) and concentrated HCl (45 mL). Then the reaction mixture was refluxed for 4 h and left overnight in a refrigerator. The precipitate was filtered off, and the solvent was evaporated. The residue was basified with ammonium hydroxide (120 mL) and was extracted with CH$_2$Cl$_2$ (3×120 mL), the organic layer was dried over Na$_2$SO$_4$, and evaporated to dryness. The crude was dissolved in 100 mL ethanol. A 2.8 M solution of hydrogen chloride in ethanol (35 mL) was then added. The precipitate formed was collected by filtration and crystallized from methanol and 2-propanol to give the product (8.59 g, 62% yield) as a brown solid.
Melting point: 220-224° C.
IR cm$^{-1}$(KBr): 3024, 2934, 2561, 1529, 1344, 1095, 740.
$^1$H NMR (300 MHz, DMSO-d6) d ppm: 1.66 (m, 2H), 1.89 (m, 2H), 2.83 (m, 2H), 3.21 (m, 3H), 3.32 (m, 2H), 3.72 (m, 1H), 4.38 (dd, J=15.96, 7.61 Hz, 1H), 4.68 (d, J=14.50 Hz, 1H), 7.55 (d, J=8.35 Hz, 1H), 8.05 (s, 2H), 8.14 (m, 2H), 11.51 (s, 1H).

Example C

The compounds of general formula (I) were prepared by the coupling of a compound of formula (II) with a compound of formula (III) by means of conventional organic chemistry methods known to those skilled in the art.

Naphthalene-1-sulfonic Acid [4-(3,4-dihydro-1H-isoquinolin-2-yl)-butyl]amide Hydrochloride

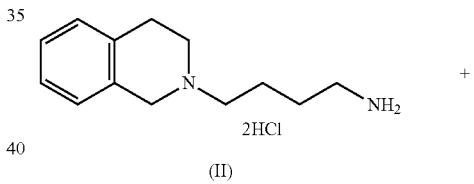

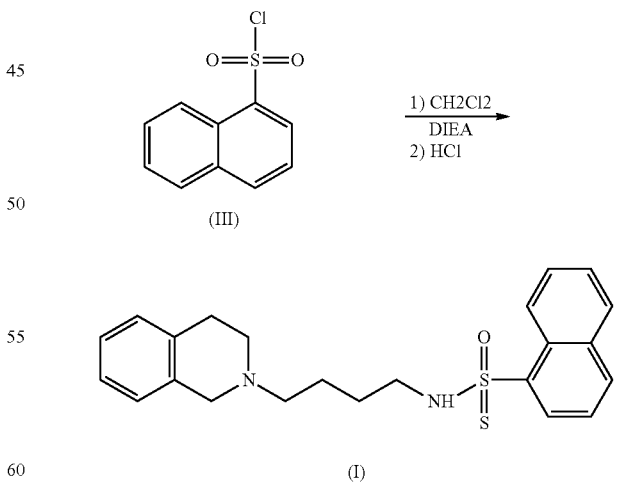

A solution of 2-(4-aminobutyl)-1,2,3,4-tetrahydroisoquinoline dihydrochloride (272 mg, 1 mmol), N,N-diisopropylethylamine (517 mg, 4 mmol) in CH$_2$Cl$_2$ (10 mL), was added naphtalene-1-sulfonyl chloride (238 mg, 1.05 mmol) and was stirred overnight at room temperature. The resulting solution was washed with water (3×15 mL) and dried over Na₂SO₄, and evaporated to dryness. The free base was dissolved in 2-propanol (5 mL). A 2.8 M solution of hydrogen chloride in ethanol (0.40 mL) was then added. The product was crystallized and collected by filtration, and vacuum dried to give a white solid (310 mg, 72%).

Melting point: 203-206° C.

IR cm$^{-1}$(KBr): 3087, 2941, 2679, 2601, 1446, 1420, 1314, 1153, 1132, 801, 775, 747.

$^1$H NMR (300 MHz, DMSO-d6) d ppm 1.38 (m, 2H), 1.66 (d, J=6.77 Hz, 2H), 2.81 (q, J=6.47 Hz, 2H), 2.91 (s, 1H), 2.99 (d, J=9.34 Hz, 2H), 3.18 (m, 2H), 3.52 (d, J=6.41 Hz, 1H), 4.12 (m, 1H), 4.36 (m, 1H), 7.21 (m, 4H), 7.69 (m, 3H), 8.10 (m, 3H), 8.23 (d, J=8.24 Hz, 1H), 8.66 (d, J=8.61 Hz, 1H), 11.02 (s, 1H).

The spectroscopic data for the identification of some of the sulfonamides compounds of the invention having general formula (I), prepared analogously to the methods described in the above examples, are shown in the following table 1:

| N° | STRUCTURE | Autonom | ¹H-NMR | MS (APCI) (M + H)⁺ |
|---|---|---|---|---|
| 1 | 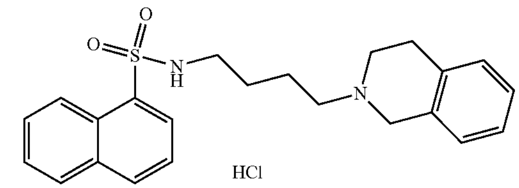 | Naphthalene-1-sulfonic acid [4-(3,4-dihydro-1H-isoquinolin-2-yl)-butyl]-amide hydrochloride | 1H NMR (300 MHz, DMSO-D6) δ ppm 1.38 (m, 2H), 1.66 (d, J = 6.77 Hz, 2H), 2.81 (q, J = 6.47 Hz, 2H), 2.91 (s, 1H), 2.99 (d, J = 9.34 Hz, 2H), 3.18 (m, 2H), 3.52 (d, J = 6.41 Hz, 1H), 4.12 (m, 1H), 4.36 (m, 1H), 7.21 (m, 4H), 7.69 (m, 3H), 8.10 (m, 3H), 8.23 (d, J = 8.24 Hz, 1H), 8.66 (d, J = 8.61 Hz, 1H), 11.02 (s, 1H) | 395 |
| 2 | 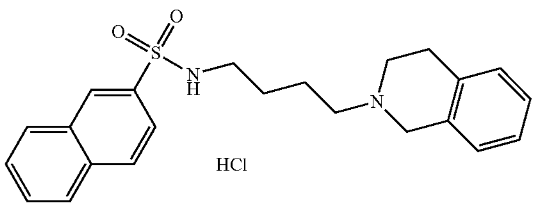 | Naphthalene-2-sulfonic acid [4-(3,4-dihydro-1H-isoquinolin-2-yl)-butyl]-amide hydrochloride | 1H NMR (300 MHz, DMSO-D6) δ ppm 1.44 (m, 2H), 1.72 (s, 2H), 2.79 (d, J = 6.41 Hz, 2H), 2.96 (m, 1H), 3.09 (s, 2H), 3.20 (s, 2H), 3.59 (s, 1H), 4.17 (m, 1H), 4.43 (m, 1H), 7.21 (m, 4H), 7.68 (m, 2H), 7.82 (m, 2H), 8.04 (d, J = 8.42 Hz, 1H), 8.15 (m, 2H), 8.43 (s, 1H), 10.64 (s, 1H) | 395 |
| 3 | 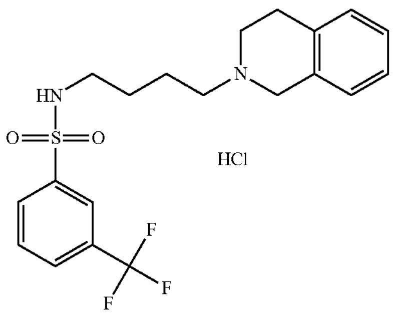 | N-[4-(3,4-Dihydro-1H-isoquinolin-2-yl)-butyl]-3-trifluoromethyl-benzenesulfonamide hydrochloride | 1H NMR (300 MHz, DMSO-D6) δ ppm 1.44 (m, 2H), 1.76 (d, J = 6.41 Hz, 2H), 2.79 (q, J = 6.59 Hz, 2H), 3.00 (m, 1H), 3.11 (s, 2H), 3.23 (m, 2H), 3.62 (d, J = 7.14 Hz, 1H), 4.20 (m, 1H), 4.45 (m, 1H), 7.23 (m, 4H), 7.87 (t, J = 7.78 Hz, 1H), 8.07 (m, 4H), 10.78 (s, 1H) | 413 |
| 4 | 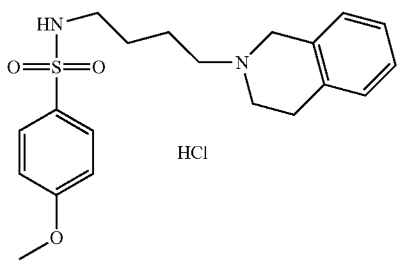 | N-[4-(3,4-Dihydro-1H-isoquinolin-2-yl)-butyl]-4-methoxy-benzenesulfonamide hydrochloride | 1H NMR (300 MHz, DMSO-D6) δ ppm 1.43 (m, 2H), 1.76 (m, 2H), 2.72 (q, J = 6.59 Hz, 2H), 2.98 (m, 1H), 3.10 (s, 2H), 3.22 (m, 2H), 3.61 (s, 1H), 3.79 (m, 3H), 4.21 (dd, J = 15.11, 7.42 Hz, 1H), 4.45 (m, 1H), 7.12 (m, 2H), 7.22 (m, 4H), 7.57 (t, J = 5.86 Hz, 1H), 7.73 (m, 2H), 10.81 (s, 1H) | 375 |

-continued

| Nº | STRUCTURE | Autonom | ¹H-NMR | MS (APCI) (M + H)+ |
|---|---|---|---|---|
| 5 | (tetrahydroisoquinoline-N-butyl-NH-SO2-phenyl) · HCl | N-[4-(3,4-Dihydro-1H-isoquinolin-2-yl)-butyl]-benzenesulfonamide hydrochloride | 1H NMR (300 MHz, DMSO-D6) δ ppm 1.45 (m, 2H), 1.75 (m, 2H), 2.76 (q, J = 6.71 Hz, 2H), 2.98 (m, 1H), 3.10 (s, 2H), 3.18 (s, 1H), 3.26 (s, 1H), 3.60 (m, 1H), 4.20 (m, 1H), 4.45 (d, J = 15.75 Hz, 1H), 7.23 (m, 4H), 7.62 (m, 3H), 7.77 (m, 3H), 10.71 (s, 1H) | 345 |
| 6 | (tetrahydroisoquinoline-N-butyl-NH-SO2-phenyl-O-phenyl-Br) · HCl | 4-(4-Bromo-phenoxy)-N-[4-(3,4-dihydro-1H-isoquinolin-2-yl)-butyl]-benzenesulfonamide hydrochloride | 1H NMR (300 MHz, DMSO-D6) δ ppm 1.43 (m, 2H), 1.75 (m, 2H), 2.75 (q, J = 6.23 Hz, 2H), 3.01 (m, 1H), 3.11 (s, 2H), 3.23 (m, 2H), 3.61 (s, 1H), 4.21 (m, 1H), 4.46 (m, 1H), 7.13 (m, 5H), 7.24 (d, J = 5.68 Hz, 2H), 7.61 (m, 2H), 7.71 (m, 1H), 7.79 (d, J = 6.96 Hz, 2H), 10.78 (s, 1H) | 515 |
| 7 | (tetrahydroisoquinoline-N-butyl-NH-SO2-thiophene) · HCl | Thiophene-2-sulfonic acid [4-(3,4-dihydro-1H-isoquinolin-2-yl)-butyl]-amide hydrochloride | 1H NMR (300 MHz, DMSO-D6) δ ppm 1.51 (m, 2H), 1.76 (m, 2H), 2.80 (m, 2H), 3.00 (m, 1H), 3.13 (m, 2H), 3.25 (m, 2H), 3.61 (s, 1H), 4.25 (m, 1H), 4.48 (m, 1H), 7.23 (m, 5H), 7.58 (dd, J = 2.93, 1.65 Hz, 1H), 7.90 (m, 2H), 10.48 (s, 1H) | 351 |
| 8 | (tetrahydroisoquinoline-N-butyl-NH-SO2-CH2-camphor) · HCl | N-[4-(3,4-Dihydro-1H-isoquinolin-2-yl)-butyl]-C-(7,7-dimethyl-2-oxo-bicyclo[2.2.1]hept-1-yl)-methanesulfonamide hydrochloride | 1H NMR (300 MHz, DMSO-D6) δ ppm 0.83 (m, 3H), 1.02 (m, 4H), 1.36 (m, 1H), 1.51 (m, 3H), 1.82 (m, 1H), 1.91 (m, 1H), 2.01 (m, 1H), 2.33 (m, 2H), 3.01 (m, 2H), 3.17 (m, 3H), 3.31 (m, 2H), 3.71 (m, 1H), 4.27 (dd, J = 15.66, 8.15 Hz, 1H), 4.50 (d, J = 14.65 Hz, 1H), 7.09 (m, 1H), 7.24 (m, 4H), 10.19 (s, 1H) | 419 |

| N° | STRUCTURE | Autonom | ¹H-NMR | MS (APCI) (M + H)⁺ |
|---|---|---|---|---|
| 9 | 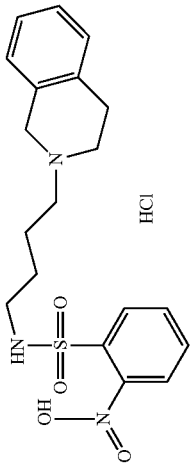 | N-[4-(3,4-Dihydro-1H-isoquinolin-2-yl)-butyl]-2-nitro-benzenesulfonamide hydrochloride | 1H NMR (300 MHz, DMSO-D6) δ ppm 1.48 (m, 2H), 1.74 (m, 2H), 2.94 (m, 2H), 3.04 (m, 1H), 3.14 (m, 2H), 3.24 (m, 2H), 3.62 (d, J = 4.39 Hz, 1H), 4.22 (m, 1H), 4.46 (m, 1H), 7.22 (m, 4H), 7.86 (m, 2H), 7.98 (m, 2H), 8.24 (m, 1H), 10.68 (s, 1H) | 390 |
| 10 | 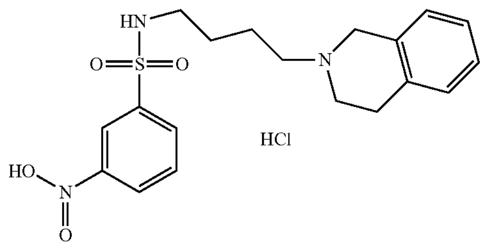 | N-[4-(3,4-Dihydro-1H-isoquinolin-2-yl)-butyl]-3-nitro-benzenesulfonamide hydrochloride | 1H NMR (300 MHz, DMSO-D6) δ ppm 1.45 (m, 2H), 1.72 (m, 2H), 2.79 (m, 2H), 3.02 (s, 1H), 3.10 (m, 2H), 3.23 (m, 2H), 3.60 (m, 1H), 4.21 (m, 1H), 4.45 (m, 1H), 7.23 (m, 4H), 7.92 (m, 1H), 8.11 (m, 1H), 8.23 (m, 1H), 8.49 (m, 2H), 10.52 (s, 1H) | 390 |
| 11 | 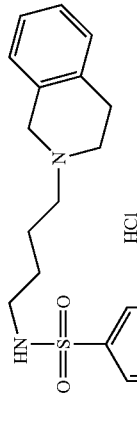 | N-[4-(3,4-Dihydro-1H-isoquinolin-2-yl)-butyl]-4-methanesulfonyl-benzenesulfonamide hydrochloride | 1H NMR (300 MHz, DMSO-D6) δ ppm 1.46 (m, J = 7.12 Hz, 2H), 1.76 (m, 2H), 2.81 (q, J = 6.59 Hz, 2H), 2.98 (m, 1H), 3.10 (m, 2H), 3.23 (m, 2H), 3.30 (s, 3H), 3.60 (m, 1H), 4.19 (m, 1H), 4.44 (m, 1H), 7.23 (m, 4H), 8.10 (m, 5H), 10.91 (s, 1H) | 423 |
| 12 | 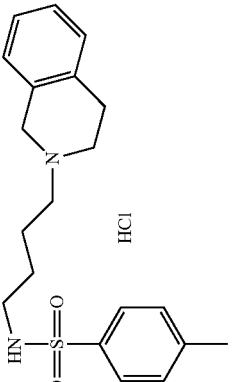 | N-[4-(3,4-Dihydro-1H-isoquinolin-2-yl)-butyl]-4-methyl-benzenesulfonamide hydrochloride | 1H NMR (300 MHz, DMSO-D6) δ ppm 1.44 (m, 2H), 1.75 (m, 2H), 2.36 (s, 3H), 2.72 (q, J = 6.59 Hz, 2H), 2.97 (m, 1H), 3.08 (d, J = 5.31 Hz, 2H), 3.22 (m, 2H), 3.60 (s, 1H), 4.21 (m, 1H), 4.44 (d, J = 15.20 Hz, 1H), 7.23 (m, 4H), 7.39 (d, J = 7.87 Hz, 2H), 7.65 (m, 3H), 10.75 (s, 1H) | 359 |

| N° | STRUCTURE | Autonom | ¹H-NMR | MS (APCI) (M + H)⁺ |
|---|---|---|---|---|
| 13 | 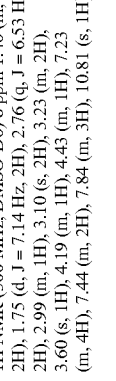 | N-[4-(3,4-Dihydro-1H-isoquinolin-2-yl)-butyl]-4-fluoro-benzenesulfonamide hydrochloride | 1H NMR (300 MHz, DMSO-D6) δ ppm 1.46 (m, 2H), 1.75 (d, J = 7.14 Hz, 2H), 2.76 (q, J = 6.53 Hz, 2H), 2.99 (m, 1H), 3.10 (s, 2H), 3.23 (m, 2H), 3.60 (s, 1H), 4.19 (m, 1H), 4.43 (m, 1H), 7.23 (m, 4H), 7.44 (m, 2H), 7.84 (m, 3H), 10.81 (s, 1H) | 363 |
| 14 | 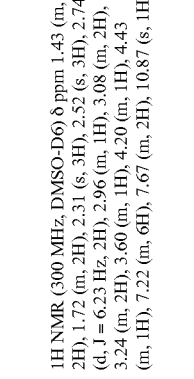 | N-[4-(3,4-Dihydro-1H-isoquinolin-2-yl)-butyl]-2,4-dimethyl-benzenesulfonamide hydrochloride | 1H NMR (300 MHz, DMSO-D6) δ ppm 1.43 (m, 2H), 1.72 (m, 2H), 2.31 (s, 3H), 2.52 (s, 3H), 2.74 (d, J = 6.23 Hz, 2H), 2.96 (m, 1H), 3.08 (m, 2H), 3.24 (m, 2H), 3.60 (m, 1H), 4.20 (m, 1H), 4.43 (m, 1H), 7.22 (m, 6H), 7.67 (m, 2H), 10.87 (s, 1H) | 373 |
| 15 | 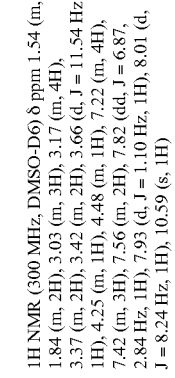 | 2-Naphthalen-1-yl-ethanesulfonic acid [4-(3,4-dihydro-1H-isoquinolin-2-yl)-butyl]-amide hydrochloride | 1H NMR (300 MHz, DMSO-D6) δ ppm 1.54 (m, 2H), 1.84 (m, 2H), 3.03 (m, 3H), 3.17 (m, 4H), 3.37 (m, 2H), 3.42 (m, 2H), 3.66 (d, J = 11.54 Hz, 1H), 4.25 (m, 1H), 4.48 (m, 1H), 7.22 (m, 4H), 7.42 (m, 3H), 7.56 (m, 2H), 7.82 (dd, J = 6.87, 2.84 Hz, 1H), 7.93 (d, J = 1.10 Hz, 1H), 8.01 (d, J = 8.24 Hz, 1H), 10.59 (s, 1H) | 423 |

| N° | STRUCTURE | Autonom | 1H-NMR | MS (APCI) (M + H)+ |
|---|---|---|---|---|
| 16 | (structure with 5-chloro-3-methylbenzothiophene-2-sulfonamide linked via butyl to tetrahydroisoquinoline, HCl salt) | 5-Chloro-3-methyl-benzo[b]thiophene-2-sulfonic acid [4-(3,4-dihydro-1H-isoquinolin-2-yl)-butyl]-amide hydrochloride | 1H NMR (300 MHz, DMSO-D6) δ ppm 1.47 (m, 2H), 1.71 (d, J = 7.14 Hz, 2H), 2.60 (s, 3H), 2.94 (m, 3H), 3.11 (m, 3H), 3.23 (d, J = 8.24 Hz, 1H), 3.60 (d, J = 10.99 Hz, 1H), 4.20 (dd, J = 15.38, 7.87 Hz, 1H), 4.44 (m, 1H), 7.20 (m, 4H), 7.53 (dd, J = 8.79, 2.01 Hz, 1H), 8.02 (m, 2H), 8.22 (m, 1H), 10.07 (s, 1H) | 449 |
| 17 | (4-acetylphenylsulfonamide linked via butyl to tetrahydroisoquinoline, HCl salt) | 4-Acetyl-N-[4-(3,4-dihydro-1H-isoquinolin-2-yl)-butyl]-benzenesulfonamide hydrochloride | 1H NMR (300 MHz, DMSO-D6) □ ppm 1.44 (m, 2H), 1.72 (s, 3H), 2.59 (s, 3H), 2.80 (s, 2H), 3.00 (m, 1H), 3.12 (s, 3H), 3.28 (s, 1H), 3.64 (d, J = 11.72 Hz, 1H), 4.23 (dd, J = 15.29, 7.96 Hz, 1H), 4.47 (d, J = 14.65 Hz, 1H), 7.22 (m, 4H), 7.91 (d, J = 8.24 Hz, 3H), 8.11 (d, J = 8.42 Hz, 2H), 10.02 (s, 1H) | 387 |
| 18 | (4-bromophenylsulfonamide linked via butyl to tetrahydroisoquinoline, HCl salt) | 4-Bromo-N-[4-(3,4-dihydro-1H-isoquinolin-2-yl)-butyl]-benzenesulfonamide hydrochloride | 1H NMR (300 MHz, DMSO-D6) δ ppm 1.43 (m, 2H), 1.71 (m, 2H), 2.76 (s, 2H), 3.07 (m, 4H), 3.28 (m, 3H), 3.65 (d, J = 12.08 Hz, 1H), 4.24 (dd, J = 15.11, 8.15 Hz, 1H), 4.48 (d, J = 15.38 Hz, 1H), 7.22 (m, 3H), 7.51 (m, 2H), 7.76 (m, 4H), 9.84 (s, 1H) | 423 |
| 19 | (ethanesulfonamide linked via butyl to tetrahydroisoquinoline, HCl salt) | Ethanesulfonic acid [4-(3,4-dihydro-1H-isoquinolin-2-yl)-butyl]-amide hydrochloride | 1H NMR (300 MHz, DMSO-D6) δ ppm 1.17 (t, J = 7.42 Hz, 3H), 1.51 (m, 2H), 1.80 (m, 2H), 2.96 (m, 5H), 3.17 (dd, J = 10.44, 5.31 Hz, 3H), 3.31 (d, J = 6.23 Hz, 1H), 3.68 (d, J = 10.99 Hz, 1H), 4.26 (dd, J = 15.66, 7.97 Hz, 1H), 4.50 (d, J = 13.92 Hz, 1H), 7.22 (m, 5H), 10.08 (s, 1H) | 297 |

| N° | STRUCTURE | Autonom | 1H-NMR | MS (APCI) (M + H)+ |
|---|---|---|---|---|
| 20 | 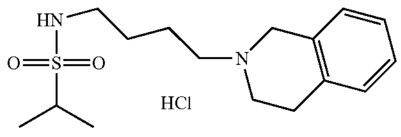 | Propane-2-sulfonic acid [4-(3,4-dihydro-1H-isoquinolin-2-yl)-butyl]-amide hydrochloride | 1H NMR (300 MHz, DMSO-D6) δ ppm 1.17 (s, 3H), 1.20 (s, 3H), 1.49 (m, 2H), 1.80 (m, 2H), 2.95 (m, 2H), 3.05 (m, 1H), 3.13 (m, 4H), 3.32 (m, 1H), 3.68 (d, J = 11.90 Hz, 1H), 4.26 (m, 1H), 4.50 (m, 1H), 7.04 (m, 1H), 7.20 (m, 4H), 9.98 (s, 1H) | 311 |
| 21 | 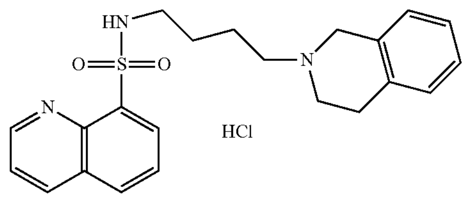 | Quinoline-8-sulfonic acid [4-(3,4-dihydro-1H-isoquinolin-2-yl)-butyl]-amide hydrochloride | 1H NMR (300 MHz, DMSO-D6) δ ppm 1.41 (m, 2H), 1.68 (m, 2H), 2.81 (s, 2H), 3.01 (m, 1H), 3.09 (m, 2H), 3.16 (m, 2H), 3.60 (d, J = 10.62 Hz, 1H), 4.20 (m, 1H), 4.44 (d, J = 16.85 Hz, 1H), 7.20 (m, 5H), 7.72 (m, 2H), 8.30 (m, 2H), 8.54 (d, J = 7.69 Hz, 1H), 9.07 (dd, J = 4.21, 1.65 Hz, 1H) | 396 |
| 22 | 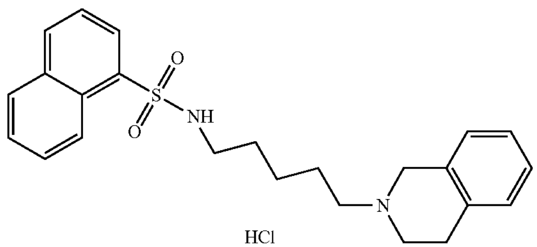 | Naphthalene-1-sulfonic acid [5-(3,4-dihydro-1H-isoquinolin-2-yl)-pentyl]-amide hydrochloride | 1H NMR (300 MHz, DMSO-D6) δ ppm 1.21 (m, 2H), 1.34 (m, 2H), 1.57 (d, J = 7.87 Hz, 2H), 2.78 (s, 2H), 3.04 (m, 3H), 3.23 (m, 2H), 3.60 (m, 1H), 4.19 (dd, J = 15.29, 8.15 Hz, 1H), 4.44 (d, J = 14.46 Hz, 1H), 7.18 (m, 5H), 7.63 (m, 4H), 7.92 (s, 1H), 8.02 (m, 1H), 8.13 (dd, J = 16.57, 7.78 Hz, 3H), 8.65 (d, J = 8.42 Hz, 1H), 9.87 (s, 1H) | 409 |
| 23 | 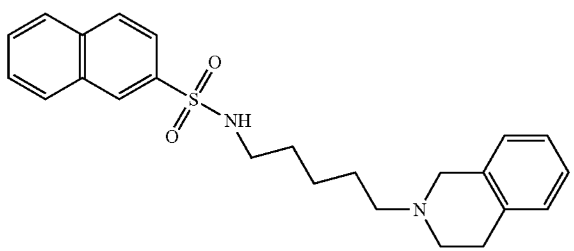 | Naphthalene-2-sulfonic acid [5-(3,4-dihydro-1H-isoquinolin-2-yl)-pentyl]-amide | 1H NMR (300 MHz, CHLOROFORM-D) δ ppm 1.34 (m, 2H), 1.52 (qt, J = 7.23 Hz, 4H), 1.63 (s, 1H), 2.41 (m, 2H), 2.66 (t, J = 5.95 Hz, 2H), 2.88 (t, J = 5.86 Hz, 2H), 2.99 (t, J = 6.23 Hz, 2H), 3.55 (s, 2H), 4.82 (s, 1H), 6.99 (m, 1H), 7.10 (m, 3H), 7.62 (m, 2H), 7.75 (dd, J = 8.61, 1.83 Hz, 1H), 7.93 (m, 3H), 8.40 (d, J = 1.28 Hz, 1H) | 409 |

| N° | STRUCTURE | Autonom | 1H-NMR | MS (APCI) (M + H)+ |
|---|---|---|---|---|
| 24 | 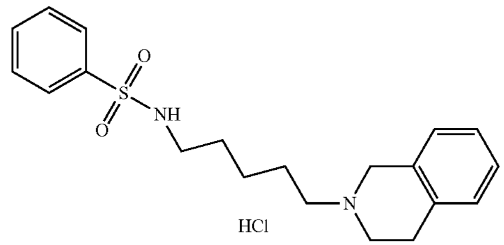 | N-[5-(3,4-Dihydro-1H-isoquinolin-2-yl)-pentyl]-benzenesulfonamide hydrochloride | 1H NMR (300 MHz, DMSO-D6) δ ppm 1.25 (m, 2H), 1.39 (d, J = 7.14 Hz, 2H), 1.68 (d, J = 7.69 Hz, 2H), 2.73 (s, 2H), 2.96 (s, 1H), 3.14 (m, 3H), 3.27 (d, J = 10.25 Hz, 1H), 3.66 (d, J = 11.35 Hz, 1H), 4.23 (dd, J = 15.47, 7.96 Hz, 1H), 4.49 (d, J = 13.92 Hz, 1H), 7.20 (m, 4H), 7.58 (m, 4H), 7.77 (m, 2H), 10.04 (s, 1H) | 359 |
| 25 | 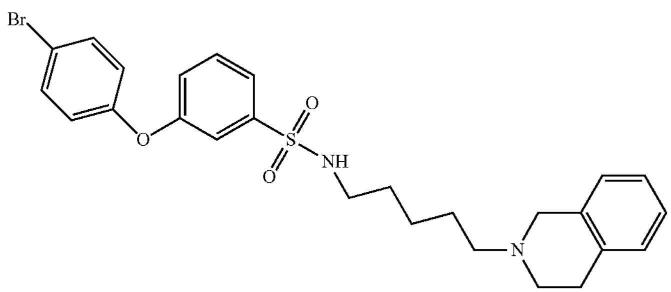 | 3-(4-Bromo-phenoxy)-N-[5-(3,4-dihydro-1H-isoquinolin-2-yl)-pentyl]-benzenesulfonamide | 1H NMR (300 MHz, CHLOROFORM-D) δ ppm 1.38 (m, 2H), 1.54 (m, 4H), 1.67 (s, 1H), 2.47 (m, 2H), 2.71 (t, J = 5.86 Hz, 2H), 2.93 (m, 3H), 3.59 (s, 2H), 4.74 (t, J = 5.68 Hz, 1H), 6.94 (m, 2H), 7.00 (m, 3H), 7.11 (m, 3H), 7.51 (m, 2H), 7.75 (m, 2H) | 529 |
| 26 | 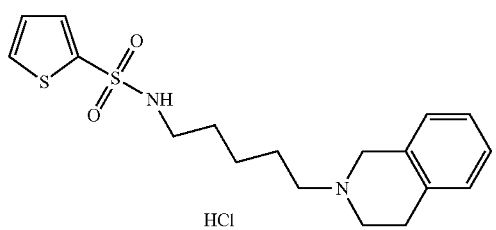 | Thiophene-2-sulfonic acid [5-(3,4-dihydro-1H-isoquinolin-2-yl)-pentyl]-amide hydrochloride | 1H NMR (300 MHz, DMSO-D6) δ ppm 1.31 (d, J = 6.96 Hz, 2H), 1.44 (m, 2H), 1.69 (s, 2H), 2.82 (s, 2H), 3.14 (m, 5H), 3.67 (d, J = 9.70 Hz, 1H), 4.24 (m, 1H), 4.50 (d, J = 17.21 Hz, 1H), 7.18 (m, 5H), 7.55 (m, 1H), 7.83 (m, 2H), 10.05 (s, 1H) | 365 |
| 27 | 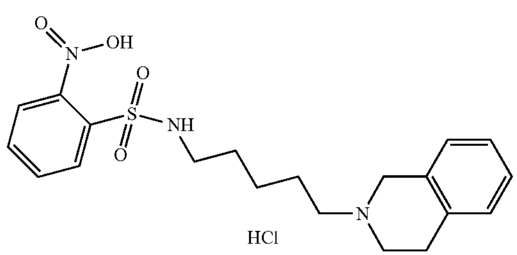 | N-[5-(3,4-Dihydro-1H-isoquinolin-2-yl)-pentyl]-2-nitro-benzenesulfonamide hydrochloride | 1H NMR (300 MHz, DMSO-D6) δ ppm 1.30 (d, J = 6.96 Hz, 2H), 1.47 (d, J = 6.77 Hz, 2H), 1.68 (m, 2H), 2.89 (d, J = 5.49 Hz, 3H), 3.11 (m, 3H), 3.26 (d, J = 7.32 Hz, 1H), 3.65 (d, J = 10.62 Hz, 1H), 4.22 (m, 1H), 4.48 (m, 1H), 7.18 (m, 4H), 7.81 (m, 3H), 7.97 (ddd, J = 5.22, 3.94, 1.46 Hz, 2H), 9.99 (s, 1H) | 404 |

| N° | STRUCTURE | Autonom | 1H-NMR | MS (APCI) (M + H)+ |
|---|---|---|---|---|
| 28 | 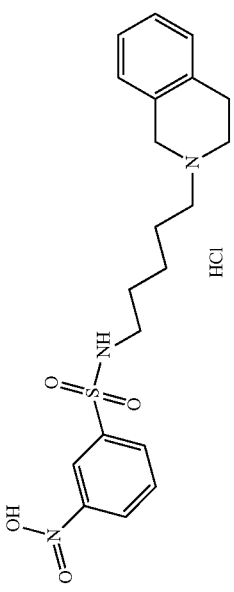 | N-[5-(3,4-Dihydro-1H-isoquinolin-2-yl)-pentyl]-3-nitro-benzenesulfonamide hydrochloride | 1H NMR (300 MHz, DMSO-D6) δ ppm 1.28 m, 2H), 1.41 (d, J = 7.32 Hz, 2H), 1.68 (m, 2H), 2.79 (s, 2H), 3.08 (m, 4H), 3.26 (m, 1H), 3.67 (m, 1H), 4.23 (m, 1H), 4.49 (d, J = 15.38 Hz, 1H), 7.19 (m, 4H), 7.85 (t, J = 7.96 Hz, 1H), 7.98 (s, 1H), 8.18 (m, 1H), 8.43 (dt, J = 8.29, 1.17 Hz, 1H), 8.52 (t, J = 1.92 Hz, 1H), 10.04 (s, 1H) | 404 |
| 29 | 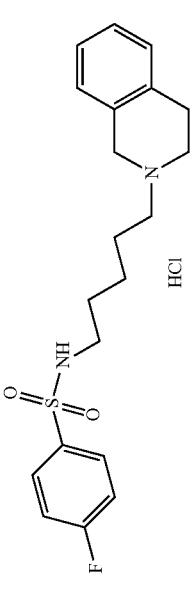 | N-[5-(3,4-Dihydro-1H-isoquinolin-2-yl)]-4-fluoro-benzenesulfonamide hydrochloride | 1H NMR (300 MHz, DMSO-D6) δ ppm 1.28 (m, 2H), 1.40 (m, 2H), 1.67 (m, 2H), 2.72 (m, 2H), 3.02 (m, 1H), 3.11 (m, 3H), 3.27 (m, J = 8.24 Hz, 1H), 3.66 (m, J = 11.35 Hz, 1H), 4.24 (dd, J = 15.47, 8.33 Hz, 1H), 4.49 (d, J = 14.83 Hz, 1H), 7.21 (m, 4H), 7.37 (d, J = 6.77 Hz, 2H), 7.64 (s, 1H), 7.83 (m, 2H), 9.96 (s, 1H) | 377 |
| 30 | 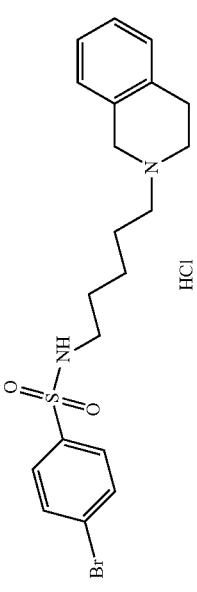 | 4-Bromo-N-[5-(3,4-dihydro-1H-isoquinolin-2-yl)-pentyl]-benzenesulfonamide hydrochloride | 1H NMR (300 MHz, DMSO-D6) δ ppm 1.25 (m, 2H), 1.40 (m, 2H), 1.68 (ddd, J = 15.38, 7.96, 7.78 Hz, 2H), 2.73 (m, 2H), 2.99 (m, 1H), 3.12 (d, J = 6.96 Hz, 3H), 3.27 (m, J = 9.16 Hz, 1H), 3.68 (m, 1H), 4.23 (dd, J = 15.38, 8.06 Hz, 1H), 4.50 (m, 1H), 7.21 (m, 4H), 7.72 (m, 5H), 10.04 (s, 1H) | 437 |
| 31 | 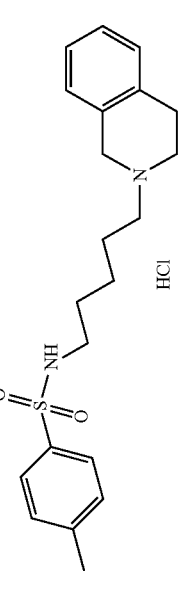 | N-[5-(3,4-Dihydro-1H-isoquinolin-2-yl)-pentyl]-4-methyl-benzenesulfonamide hydrochloride | 1H NMR (300 MHz, DMSO-D6) δ ppm 1.28 (d, J = 6.41 Hz, 2H), 1.41 (d, J = 6.96 Hz, 2H), 1.68 (m, 2H), 2.33 (s, 3H), 2.70 (t, J = 6.23 Hz, 2H), 2.98 (m, 1H), 3.13 (d, J = 5.68 Hz, 3H), 3.26 (m, J = 8.97 Hz, 1H), 3.65 (d, J = 10.80 Hz, 1H), 4.22 (m, 1H), 4.48 (d, J = 15.38 Hz, 1H), 7.20 (m, 4H), 7.34 (d, J = 8.06 Hz, 2H), 7.50 (s, 1H), 7.65 (d, J = 7.87 Hz, 2H), 10.11 (s, 1H) | 373 |

| N° | STRUCTURE | Autonom | 1H-NMR | MS (APCI) (M + H)+ |
|---|---|---|---|---|
| 32 | (structure) HCl | N-[5-(3,4-Dihydro-1H-isoquinolin-2-yl)-pentyl]-2,4-dimethyl-benzenesulfonamide hydrochloride | 1H NMR (300 MHz, DMSO-D6) δ ppm 1.25 (m, 2H), 1.40 (m, 2H), 1.64 (m, 2H), 2.27 (s, 3H), 2.49 (s, 3H), 2.72 (m, 2H), 3.01 (m, 1H), 3.11 (m, 3H), 3.26 (m, J = 8.06 Hz, 2H), 3.65 (d, J = 11.35 Hz, 1H), 4.23 (dd, J = 15.66, 8.33 Hz, 1H), 4.48 (d, J = 15.56 Hz, 1H), 7.16 (m, 6H), 7.51 (s, 1H), 7.65 (d, J = 7.87 Hz, 1H), 9.83 (s, 1H) | 387 |
| 33 | (structure) HCl | 2-Naphthalen-1-yl-ethanesulfonic acid [5-(3,4-dihydro-1H-isoquinolin-2-yl)-pentyl]-amide hydrochloride | 1H NMR (300 MHz, DMSO-D6) δ ppm 1.36 (m, 2H), 1.51 (m, 2H), 1.76 (m, 2H), 3.00 (m, 3H), 3.15 (m, 3H), 3.33 (m, 3H), 3.43 (m, 2H), 3.69 (m, 1H), 4.25 (dd, J = 15.38, 8.24 Hz, 1H), 4.50 (d, J = 14.65 Hz, 1H), 7.21 (m, 5H), 7.42 (m, 2H), 7.55 (m, 2H), 7.79 (m, 1H), 7.91 (d, J = 8.24 Hz, 1H), 8.00 (d, J = 8.42 Hz, 1H), 10.11 (s, 1H) | 437 |
| 34 | (structure) HCl | Quinoline-8-sulfonic acid [5-(3,4-dihydro-1H-isoquinolin-2-yl)-pentyl]-amide hydrochloride | 1H NMR (300 MHz, DMSO-D6) δ ppm 1.20 (m, 2H), 1.36 (m, 2H), 1.59 (m, 2H), 2.78 (t, J = 6.50 Hz, 2H), 3.04 (m, 4H), 3.23 (m, 1H), 3.61 (m, 1H), 4.20 (dd, J = 15.47, 8.15 Hz, 1H), 4.45 (d, J = 15.20 Hz, 1H), 7.18 (m, 5H), 7.69 (m, 2H), 8.27 (dd, J = 15.29, 7.60 Hz, 2H), 8.52 (m, 1H), 9.05 (dd, J = 4.12, 1.56 Hz, 1H), 9.80 (s, 1H) | 410 |
| 35 | (structure) HCl | 5-Chloro-3-methyl-benzo[b]thiophene-2-sulfonic acid [5-(3,4-dihydro-1H-isoquinolin-2-yl)-pentyl]-amide hydrochloride | 1H NMR (300 MHz, DMSO-D6) δ ppm 1.27 (m, 2H), 1.42 (m, 2H), 1.65 (m, 2H), 2.62 (s, 3H), 2.89 (m, 2H), 3.06 (m, 4H), 3.25 (m, 1H), 3.62 (d, J = 10.25 Hz, 1H), 4.20 (dd, J = 15.56, 8.06 Hz, 1H), 4.45 (d, J = 15.20 Hz, 1H), 7.19 (m, 4H), 7.51 (dt, J = 8.70, 1.88 Hz, 1H), 8.00 (m, 2H), 8.14 (s, 1H), 9.88 (s, 1H) | 463 |

| N° | STRUCTURE | Autonom | ¹H-NMR | MS (APCI) (M + H)⁺ |
|---|---|---|---|---|
| 36 | 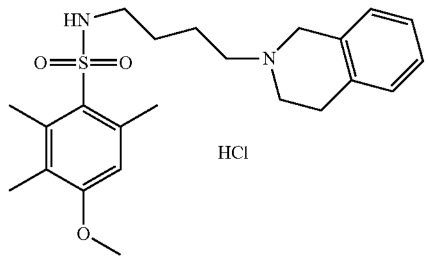 | N-[4-(3,4-Dihydro-1H-isoquinolin-2-yl)-butyl]-4-methoxy-2,3,6-trimethyl-benzenesulfonamide hydrochloride | 1H NMR (300 MHz, DMSO-D6) δ ppm 1.42 (m, 2H), 1.66 (m, 2H), 2.04 (m, 6H), 2.56 (s, 3H), 2.73 (t, J = 6.41 Hz, 2H), 3.01 (m, 1H), 3.09 (m, 3H), 3.23 (m, 1H), 3.61 (d, J = 11.17 Hz, 1H), 3.76 (s, 3H), 4.20 (dd, J = 15.47, 7.96 Hz, 1H), 4.44 (d, J = 14.65 Hz, 1H), 6.76 (s, 1H), 7.20 (m, 4H), 7.37 (s, 1H), 10.16 (s, 1H) | 417 |
| 37 | 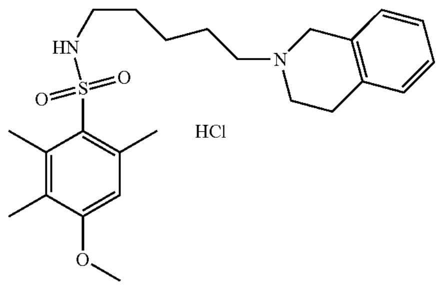 | N-[5-(3,4-Dihydro-1H-isoquinolin-2-yl)-pentyl]-4-methoxy-2,3,6-trimethyl-benzenesulfonamide hydrochloride | 1H NMR (300 MHz, DMSO-D6) δ ppm 1.25 (m, J = 6.59 Hz, 2H), 1.38 (m, 2H), 1.63 (m, J = 7.32 Hz, 2H), 2.06 (m, 6H), 2.56 (s, 3H), 2.70 (m, 2H), 3.05 (m, 4H), 3.25 (m, 1H), 3.64 (d, J = 11.35 Hz, 1H), 3.75 (s, 3H), 4.22 (dd, J = 15.11, 8.15 Hz, 1H), 4.47 (d, J = 14.65 Hz, 1H), 6.76 (s, 1H), 7.21 (m, 5H), 10.03 (s, 1H) | 431 |
| 38 | 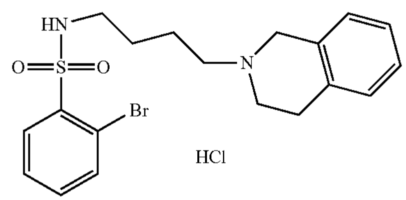 | 2-Bromo-N-[4-(3,4-dihydro-1H-isoquinolin-2-yl)-butyl]-benzenesulfonamide hydrochloride | 1H NMR (300 MHz, DMSO-D6) δ ppm 1.45 (m, 2H), 1.72 (m, 2H), 2.87 (q, J = 6.04 Hz, 2H), 2.99 (m, 1H), 3.12 (m, 3H), 3.26 (m, 1H), 3.64 (d, J = 12.08 Hz, 1H), 4.23 (dd, J = 15.29, 7.96 Hz, 1H), 4.46 (m, 1H), 7.20 (m, 4H), 7.50 (m, 2H), 7.81 (d, J = 7.32 Hz, 1H), 7.90 (s, 1H), 7.97 (d, J = 7.51 Hz, 1H), 9.93 (s, 1H) | 423 |
| 39 | 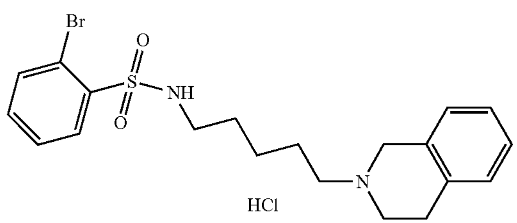 | 2-Bromo-N-[5-(3,4-dihydro-1H-isoquinolin-2-yl)-pentyl]-benzenesulfonamide hydrochloride | | 437 |

| N° | STRUCTURE | Autonom | ¹H-NMR | MS (APCI) (M + H)⁺ |
|---|---|---|---|---|
| 40 | 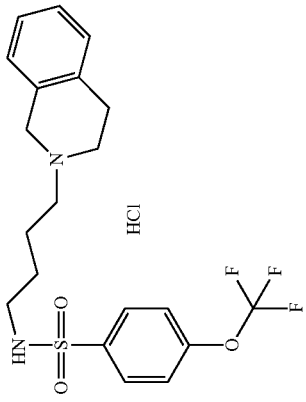 | N-[4-(3,4-Dihydro-1H-isoquinolin-2-yl)-butyl]-4-trifluoromethoxy-benzenesulfonamide hydrochloride | 1H NMR (300 MHz, DMSO-D6) δ ppm 1.45 (m, 2H), 1.73 (m, 2H), 2.78 (s, 2H), 2.99 (m, 1H), 3.14 (m, 3H), 3.26 (d, J = 6.96 Hz, 1H), 3.65 (m, 1H), 4.24 (m, 1H), 4.48 (d, J = 15.20 Hz, 1H), 7.19 (m, 4H), 7.53 (d, J = 8.61 Hz, 2H), 7.90 (m, 3H), 10.12 (s, 1H) | 429 |
| 41 | 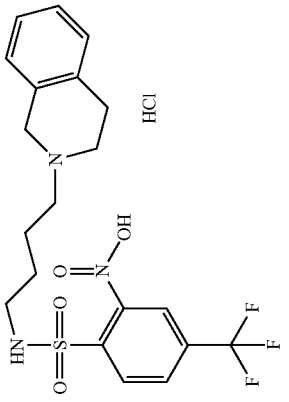 | N-[4-(3,4-Dihydro-1H-isoquinolin-2-yl)-butyl]-2-nitro-4-trifluoromethyl-benzenesulfonamide hydrochloride | 1H NMR (300 MHz, DMSO-D6) δ ppm 1.50 (m, 2H), 1.75 (m, 2H), 2.97 (m, 3H), 3.14 (m, 3H), 3.31 (m, 1H), 3.65 (m, 1H), 4.24 (dd, J = 15.38, 8.30 Hz, 1H), 4.48 (d, J = 14.65 Hz, 1H), 7.20 (m, 4H), 8.20 (m, 2H), 8.47 (s, 2H), 10.01 (s, 1H) | 458 |
| 42 | 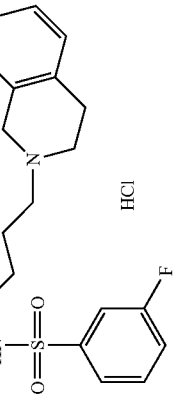 | N-[4-(3,4-Dihydro-1H-isoquinolin-2-yl)-butyl]-3-fluoro-benzenesulfonamide hydrochloride | 1H NMR (300 MHz, DMSO-06) δ ppm 1.44 (m, 2H), 1.72 (m, 2H), 2.78 (s, 2H), 2.99 (m, 1H), 3.12 (m, 3H), 3.27 (m, 1H), 3.65 (m, 1H), 4.23 (dd, J = 14.92, 8.33 Hz, 1H), 4.47 (d, J = 16.11 Hz, 1H), 7.18 (m, 4H), 7.41 (m, J = 7.64, 5.36, 1H), 7.58 (m, 3H), 7.79 (s, 1H), 9.91 (s, 1H) | 363 |

| N° | STRUCTURE | Autonom | ¹H-NMR | MS (APCI) (M + H)⁺ |
|---|---|---|---|---|
| 43 | 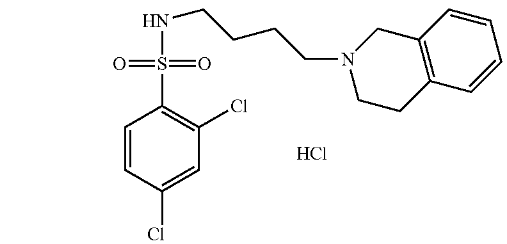 | 2,4-Dichloro-N-[4-(3,4-dihydro-1H-isoquinolin-2-yl)-butyl]-benzenesulfonamide hydrochloride | 1H NMR (300 MHz, DMSO-D6) δ ppm 1.44 (m, 2H), 1.70 (m, 2H), 2.86 (q, J = 6.51 Hz, 2H), 2.95 (m, 1H), 3.12 (m, 3H), 3.26 (m, 1H), 3.63 (d, J = 11.23 Hz, 1H), 4.22 (dd, J = 15.38, 7.57 Hz, 1H), 4.45 (m, 1H), 7.20 (m, 4H), 7.55 (m, 1H), 7.75 (m, 1H), 7.93 (m, 1H), 8.03 (s, 1H), 10.06 (s, 1H) | 413 |
| 44 | 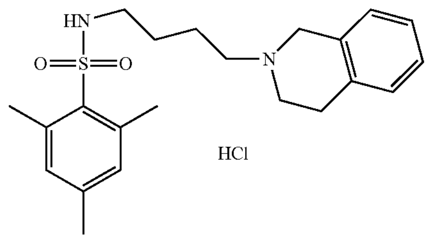 | N-[4-(3,4-Dihydro-1H-isoquinolin-2-yl)-butyl]-2,4,6-trimethyl-benzenesulfonamide hydrochloride | 1H NMR (300 MHz, DMSO-D6) δ ppm 1.41 (m, 2H), 1.68 (m, 2H), 2.18 (s, 3H), 2.53 (s, 6H), 2.74 (m, 2H), 3.06 (m, 4H), 3.25 (m, 1H), 3.63 (m, 1H), 4.21 (dd, J = 15.56, 7.51 Hz, 1H), 4.45 (d, J = 14.28 Hz, 1H), 6.98 (s, 2H), 7.20 (m, 4H), 7.45 (s, 1H), 9.96 (s, 1H) | 387 |
| 45 | 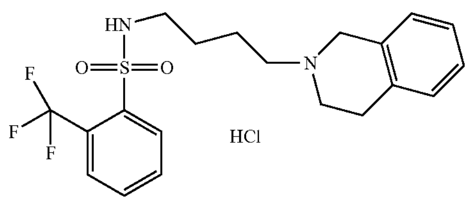 | N-[4-(3,4-Dihydro-1H-isoquinolin-2-yl)-butyl]-2-trifluoromethyl-benzenesulfonamide hydrochloride | 1H NMR (300 MHz, DMSO-D6) δ ppm 1.50 (m, 2H), 1.74 (d, J = 6.59 Hz, 2H), 2.91 (m, 2H), 3.02 (m, 1H), 3.14 (m, J = 6.59 Hz, 3H), 3.27 (m, 1H), 3.64 (m, 1H), 4.24 (dd, J = 15.38, 8.42 Hz, 1H), 4.47 (d, J = 15.20 Hz, 1H), 7.20 (m, 4H), 7.79 (m, 2H), 7.90 (d, J = 7.51 Hz, 1H), 8.06 (d, J = 7.51 Hz, 2H), 9.92 (s, 1H) | 413 |
| 46 | 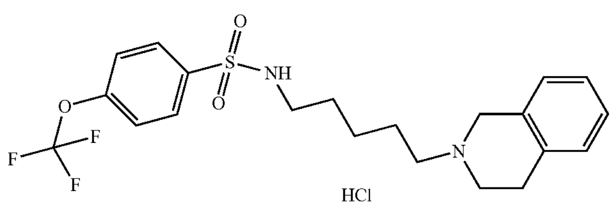 | N-[5-(3,4-Dihydro-1H-isoquinolin-2-yl)-pentyl]-4-trifluoromethoxy-benzenesulfonamide hydrochloride | 1H NMR (300 MHz, DMSO-D6) δ ppm 1.26 (m, 2H), 1.40 (m, 2H), 1.66 (m, 2H), 2.74 (t, J = 6.87 Hz, 2H), 2.97 (m, 1H), 3.11 (m, 3H), 3.26 (m, 1H), 3.64 (m, 1H), 4.22 (dd, J = 15.38, 8.24 Hz, 1H), 4.47 (m, 1H), 7.18 (m, 4H), 7.45 (d, J = 8.61 Hz, 2H), 7.68 (s, 1H), 7.87 (m, 2H), 9.80 (s, 1H) | 443 |

| N° | STRUCTURE | Autonom | 1H-NMR | MS (APCI) (M + H)+ |
|---|---|---|---|---|
| 47 | 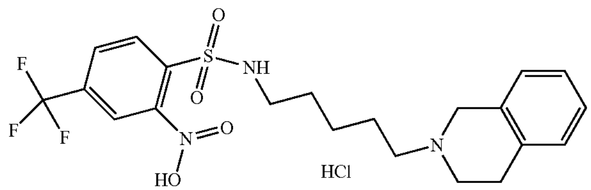 | N-[5-(3,4-Dihydro-1H-isoquinolin-2-yl)-pentyl]-2-nitro-4-trifluoromethyl-benzenesulfonamide hydrochloride | 1H NMR (300 MHz, DMSO-D6) δ ppm 1.29 (m, 2H), 1.47 (m, 2H), 1.68 (m, 2H), 2.92 (q, J = 6.53 Hz, 2H), 3.01 (m, 1H), 3.11 (m, 3H), 3.28 (m, 1H), 3.66 (m, 1H), 4.23 (dd, J = 15.20, 8.42 Hz, 1H), 4.48 (d, J = 15.56 Hz, 1H), 7.17 (m, 4H), 8.18 (m, 2H), 8.38 (s, 2H), 9.74 (s, 1H) | 472 |
| 48 | 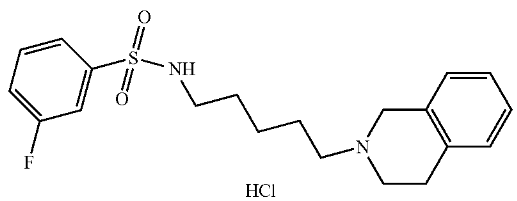 | N-[5-(3,4-Dihydro-1H-isoquinolin-2-yl)-pentyl]-3-fluoro-benzenesulfonamide hydrochloride | 1H NMR (300 MHz, DMSO-D6) δ ppm 1.28 (m, 2H), 1.40 (m, 2H), 1.66 (m, 2H), 2.75 (d, J = 6.35 Hz, 2H), 2.98 (m, 1H), 3.09 (m, 3H), 3.25 (m, 1H), 3.66 (m, 1H), 4.25 (d, J = 8.06 Hz, 1H), 4.47 (d, J = 14.40 Hz, 1H), 7.19 (m, 4H), 7.36 (m, 1H), 7.57 (m, 4H), 9.86 (s, 1H) | 377 |
| 49 | 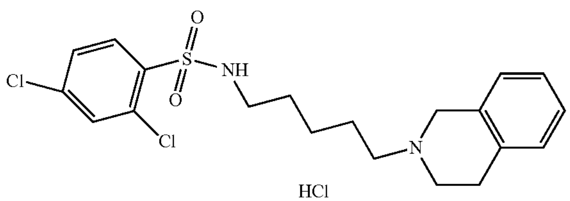 | 2,4-Dichloro-N-[5-(3,4-dihydro-1H-isoquinolin-2-yl)-pentyl]-benzenesulfonamide hydrochloride | 1H NMR (300 MHz, DMSO-D6) δ ppm 1.26 (m, 2H), 1.40 (m, 2H), 1.64 (m, 2H), 2.80 (m, 2H), 2.95 (m, 1H), 3.09 (m, 3H), 3.26 (m, 1H), 3.63 (d, J = 10.01 Hz, 1H), 4.21 (dd, J = 15.26, 7.93 Hz, 1H), 4.45 (d, J = 15.38 Hz, 1H), 7.15 (m, 4H), 7.48 (dd, J = 8.55, 2.20 Hz, 1H), 7.67 (d, J = 2.20 Hz, 1H), 7.90 (d, J = 8.55 Hz, 2H), 9.88 (s, 1H) | 427 |
| 50 | 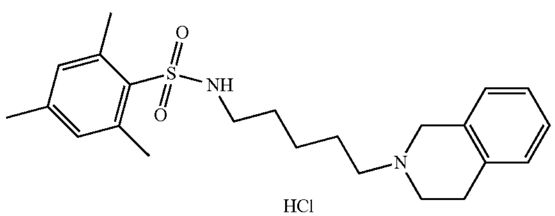 | N-[5-(3,4-Dihydro-1H-isoquinolin-2-yl)-pentyl]-2,4,6-trimethyl-benzenesulfonamide hydrochloride | 1H NMR (300 MHz, DMSO-D6) δ ppm 1.25 (m, 2H), 1.37 (m, 2H), 1.64 (m, 2H), 2.19 (s, 3H), 2.51 (s, 6H), 2.71 (t, J = 6.35 Hz, 2H), 3.06 (m, 4H), 3.22 (m, 1H), 3.63 (m, 1H), 4.21 (dd J = 15.26, 8.18 Hz, 1H), 4.46 (d, J = 14.89 Hz, 1H), 6.95 (s, 2H), 7.20 (m, 4H), 7.36 (s, 1H), 10.04 (s, 1H) | 401 |

| N° | STRUCTURE | Autonom | ¹H-NMR | MS (APCI) (M + H)⁺ |
|---|---|---|---|---|
| 51 | 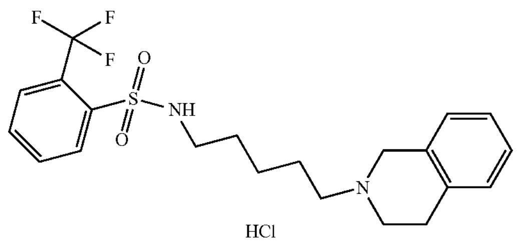 | N-[5-(3,4-Dihydro-1H-isoquinolin-2-yl)-pentyl]-2-trifluoromethyl-benzenesulfonamide hydrochloride | 1H NMR (300 MHz, DMSO-D6) δ ppm 1.30 (m, 2H), 1.46 (m, 2H), 1.69 (m, 2H), 2.87 (m, 2H), 2.97 (m, 1H), 3.12 (m, 3H), 3.27 (d, J = 11.47 Hz, 1H), 3.66 (d, J = 10.74 Hz, 1H), 4.23 (dd, J = 15.50, 8.18 Hz, 1H), 4.48 (d, J = 14.89 Hz, 1H), 7.19 (m, 4H), 7.77 (m, 2H), 7.88 (d, J = 7.81 Hz, 2H), 8.04 (d, J = 7.81 Hz, 1H), 9.94 (s, 1H) | 427 |
| 52 | 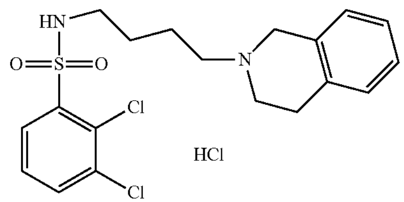 | 2,3-Dichloro-N-[4-(3,4-dihydro-1H-isoquinolin-2-yl)-butyl]-benzenesulfonamide hydrochloride | 1H NMR (300 MHz, DMSO-D6) δ ppm 1.46 (m, 2H), 1.77 (m, 2H), 2.88 (q, J = 6.71 Hz, 2H), 3.00 (s, 1H), 3.15 (s, 4H), 3.60 (m, 1H), 4.20 (dd, J = 15.29, 7.60 Hz, 1H), 4.43 (m, 1H), 7.20 (m, 4H), 7.56 (t, J = 7.96 Hz, 1H), 7.95 (m, 2H), 8.21 (m, 1H), 10.98 (s, 1H) | 413 |
| 53 | 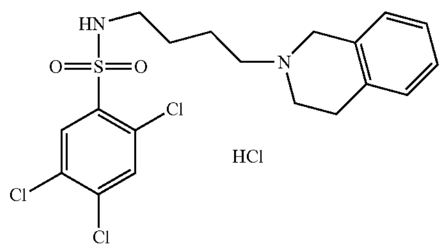 | 2,4,5-Trichloro-N-[4-(3,4-dihydro-1H-isoquinolin-2-yl)-butyl]-benzenesulfonamide hydrochloride | 1H NMR (300 MHz, DMSO-D6) δ ppm 1.46 (m, 2H), 1.75 (m, 2H), 2.87 (s, 2H), 3.01 (m, 1H), 3.12 (m, 3H), 3.23 (m, 1H), 3.61 (m, 1H), 4.21 (dd, J = 15.01, 8.06 Hz, 1H), 4.44 (d, J = 15.93 Hz, 1H), 7.23 (m, 4H), 8.07 (m, 1H), 8.13 (m, 1H), 8.28 (s, 1H), 10.83 (s, 1H) | 447 |
| 54 | 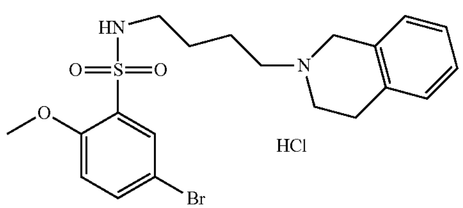 | 5-Bromo-N-[4-(3,4-dihydro-1H-isoquinolin-2-yl)-butyl]-2-methoxy-benzenesulfonamide hydrochloride | 1H NMR (300 MHz, DMSO-D6) δ ppm 1.44 (m, 2H), 1.77 (m, 2H), 2.81 (q, J = 6.77 Hz, 2H), 2.98 (m, 1H), 3.10 (m, 2H), 3.24 (m, 2H), 3.61 (m, 1H), 3.89 (s, 3H), 4.20 (m, 1H), 4.44 (m, 1H), 7.22 (m, 5H), 7.56 (t, J = 5.95 Hz, 1H), 7.78 (m, 2H), 11.03 (s, 1H) | 453 |

| N° | STRUCTURE | Autonom | ¹H-NMR | MS (APCI) (M + H)⁺ |
|---|---|---|---|---|
| 55 | 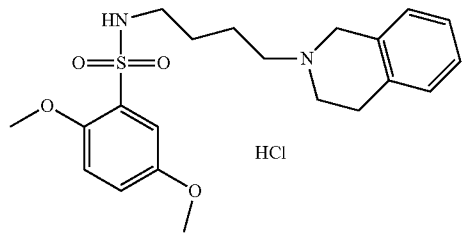 | N-[4-(3,4-Dihydro-1H-isoquinolin-2-yl)-butyl]-2,5-dimethoxy-benzenesulfonamide hydrochloride | 1H NMR (300 MHz, DMSO-D6) δ ppm 1.44 (m, 2H), 1.76 (m, 2H), 2.79 (q, J = 6.65 Hz, 2H), 2.98 (m, 1H), 3.09 (m, 2H), 3.22 (m, 2H), 3.61 (m, 1H), 3.74 (s, 3H), 3.84 (s, 3H), 4.21 (m, 1H), 4.44 (d, J = 15.20 Hz, 1H), 7.22 (m, 7H), 7.33 (t, J = 5.95 Hz, 1H), 10.89 (s, 1H) | 405 |
| 56 | 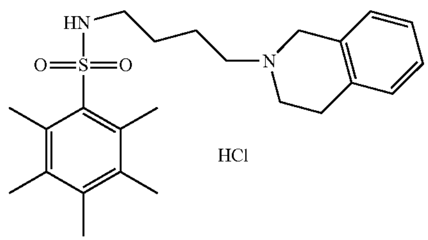 | N-[4-(3,4-Dihydro-1H-isoquinolin-2-yl)-butyl]-2,3,4,5,6-pentamethyl-benzenesulfonamide hydrochloride | 1H NMR (300 MHz, DMSO-D6) δ ppm 1.43 (m, 2H), 1.73 (m, 2H), 2.18 (s, 6H), 2.22 (s, 3H), 2.48 (s, 6H), 2.74 (q, J = 6.59 Hz, 2H), 2.97 (m, 1H), 3.09 (s, 2H), 3.19 (d, J = 9.34 Hz, 2H), 3.58 (m, 1H), 4.18 (dd, J = 15.66, 7.78 Hz, 1H), 4.43 (m, 1H), 7.23 (m, 4H), 7.48 (t, J = 5.86 Hz, 1H), 10.80 (s, 1H) | 415 |
| 57 | 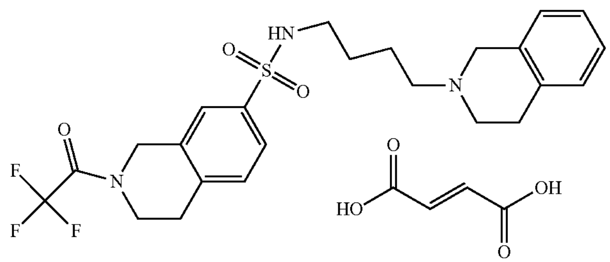 | 2-(2,2,2-Trifluoro-acetyl)-1,2,3,4-tetrahydro-isoquinoline-7-sulfonic acid [4-(3,4-dihydro-1H-isoquinolin-2-yl)-butyl]-amide fumarate | | 496 |
| 58 | 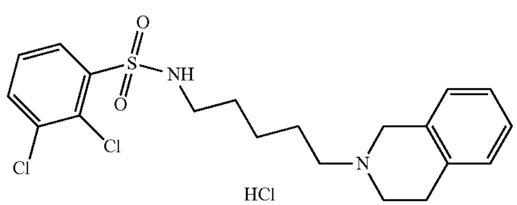 | 2,3-Dichloro-N-[5-(3,4-dihydro-1H-isoquinolin-2-yl)-pentyl]-benzenesulfonamide hydrochloride | 1H NMR (300 MHz, DMSO-D6) δ ppm 1.25 (m, 2H), 1.42 (m, 2H), 1.71 (m, 2H), 2.86 (q, J = 6.71 Hz, 2H), 2.95 (m, 1H), 3.07 (m, 2H), 3.21 (m, 2H), 3.62 (m, 1H), 4.19 (d, J = 7.69 Hz, 1H), 4.23 (s, 1H), 4.47 (d, J = 15.93 Hz, 4H), 7.22 (m, 4H), 7.56 (t, J = 8.06 Hz, 1H), 7.93 (ddd, J = 7.92, 6.36, 1.46 Hz, 2H), 8.14 (m, 1H), 10.70 (s, 1H) | 427 |

| N° | STRUCTURE | Autonom | ¹H-NMR | MS (APCI) (M + H)⁺ |
|---|---|---|---|---|
| 59 | (2,4,5-trichlorophenyl sulfonamide with tetrahydroisoquinoline-pentyl) · HCl | 2,4,5-Trichloro-N-[5-(3,4-dihydro-1H-isoquinolin-2-yl)-pentyl]-benzenesulfonamide hydrochloride | 1H NMR (300 MHz, DMSO-D6) δ ppm 1.27 (m, 2H), 1.44 (m, 2H), 1.73 (m, 2H), 2.88 (m, J = 6.04 Hz, 2H), 2.99 (m, 1H), 3.08 (m, 2H), 3.23 (m, 2H), 3.61 (m, 1H), 4.21 (dd, J = 15.20, 7.51 Hz, 1H), 4.46 (d, J = 15.01 Hz, 1H), 7.22 (m, 4H), 8.06 (s, 1H), 8.13 (s, 1H), 8.22 (m, 1H), 10.93 (s, 1H) | 461 |
| 60 | (5-bromo-2-methoxyphenyl sulfonamide with tetrahydroisoquinoline-pentyl) · HCl | 5-Bromo-N-[5-(3,4-dihydro-1H-isoquinolin-2-yl)-pentyl]-2-methoxy-benzenesulfonamide hydrochloride | 1H NMR (300 MHz, DMSO-D6) δ ppm 1.28 (m, 2H), 1.41 (m, 2H), 1.70 (m, 2H), 2.79 (m, 2H), 2.98 (m, 1H), 3.08 (m, 2H), 3.21 (m, 2H), 3.61 (m, 1H), 3.89 (s, 3H), 4.22 (dd, J = 14.83, 8.24 Hz, 1H), 4.47 (d, J = 16.66 Hz, 1H), 7.19 (s, 2H), 7.24 (dd, J = 6.32, 3.39 Hz, 3H), 7.50 (m, 1H), 7.78 (m, 2H), 10.63 (s, 1H) | 467 |
| 61 | (2,5-dimethoxyphenyl sulfonamide with tetrahydroisoquinoline-pentyl) · HCl | N-[5-(3,4-Dihydro-1H-isoquinolin-2-yl)-pentyl]-2,5-dimethoxy-benzenesulfonamide hydrochloride | 1H NMR (300 MHz, DMSO-D6) δ ppm 1.26 (m, 2H), 1.40 (m, 2H), 1.69 (m, 2H), 2.77 (q, J = 6.41 Hz, 2H), 3.08 (m, 3H), 3.22 (m, 2H), 3.66 (m, 1H), 3.74 (s, 3H), 3.83 (s, 3H), 4.22 (dd, J = 15.84, 8.88 Hz, 1H), 4.47 (d, J = 15.01 Hz, 1H), 7.23 (m, 8H), 10.51 (s, 1H) | 419 |
| 62 | (pentamethylphenyl sulfonamide with tetrahydroisoquinoline-pentyl) · HCl | N-[5-(3,4-Dihydro-1H-isoquinolin-2-yl)-pentyl]-2,3,4,5,6-pentamethyl-benzenesulfonamide hydrochloride | 1H NMR (300 MHz, DMSO-D6) δ ppm 1.26 (m, 2H), 1.41 (m, 2H), 1.69 (m, 2H), 2.18 (s, 6H), 2.22 (s, 3H), 2.47 (s, 6H), 2.72 (q, J = 6.47 Hz, 2H), 3.03 (m, 3H), 3.23 (m, 2H), 3.63 (m, 1H), 4.20 (dd, J = 15.66, 7.78 Hz, 1H), 4.46 (d, J = 15.56 Hz, 1H), 7.23 (m, 4H), 7.41 (t, J = 5.77 Hz, 1H), 10.67 (s, 1H) | 429 |

-continued

| N° | STRUCTURE | Autonom | 1H-NMR | MS (APCI) (M + H)+ |
|---|---|---|---|---|
| 63 | 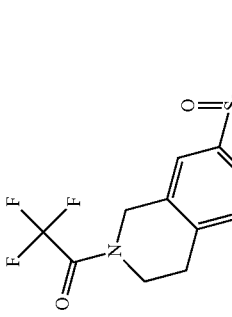 | 2-(2,2,2-Trifluoro-acetyl)-1,2,3,4-tetrahydro-isoquinoline-7-sulfonic acid [5-(3,4-dihydro-1H-isoquinolin-2-yl)-pentyl]-amide hydrochloride | 1H NMR (300 MHz, DMSO-D6) δ ppm 1.29 (m, 2H), 1.41 (m, 2H), 1.45 (s, 2H), 1.73 (m, 2H), 2.74 (m, 2H), 2.99 (m, 1H), 3.08 (m, 2H), 3.24 (m, 2H), 3.63 (m, 1H), 3.81 (m, 2H), 4.21 (m, 1H), 4.47 (m, 1H), 4.84 (m, 2H), 7.24 (m, 4H), 7.42 (d, J = 8.24 Hz, 1H), 7.63 (m, 3H), 10.82 (s, 1H) | 510 |
| 64 | 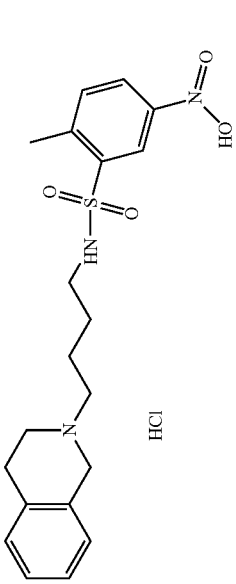 | N-[4-(3,4-Dihydro-1H-isoquinolin-2-yl)-butyl]-2-methyl-5-nitro-benzenesulfonamide hydrochloride | | 404 |
| 65 | 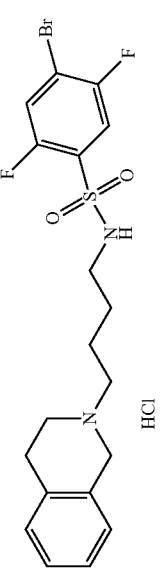 | 4-Bromo-N-[4-(3,4-dihydro-1H-isoquinolin-2-yl)-butyl]-2,5-difluoro-benzenesulfonamide hydrochloride | 1H NMR (300 MHz, DMSO-D6) δ ppm 1.46 (m, 2H), 1.75 (m, 2H), 2.91 (m, 2H), 3.02 (m, 1H), 3.15 (m, 2H), 3.24 (m, 2H), 3.63 (m, 1H), 4.23 (dd, J = 14.79, 7.32 Hz, 1H), 4.46 (d, J = 14.35 Hz, 1H), 7.25 (m, 4H), 7.72 (dd, J = 7.76, 6.15 Hz, 1H), 8.06 (dd, J = 9.15, 5.34 Hz, 1H), 8.27 (m, 1H), 10.44 (s, 1H) | 459 |
| 66 | 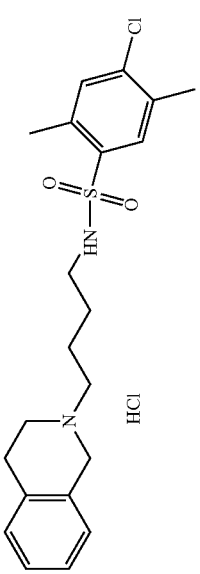 | 4-Chloro-N-[4-(3,4-dihydro-1H-isoquinolin-2-yl)-butyl]-2,5-dimethyl-benzenesulfonamide hydrochloride | 1H NMR (300 MHz, DMSO-D6) δ ppm 1.42 (m, 2H), 1.69 (m, 2H), 2.28 (s, 3H), 2.48 (s, 3H), 2.77 (t, J = 5.37 Hz, 2H), 2.97 (m, 1H), 3.10 (d, J = 6.35 Hz, 3H), 3.25 (dd, J = 9.03 Hz, 1H), 3.61 (m, 1H), 4.21 (dd, J = 15.63, 8.30 Hz, 1H), 4.44 (m, 1H), 7.16 (m, 4H), 7.36 (s, 1H), 7.71 (s, 2H), 9.91 (s, 1H) | 407 |

| N° | STRUCTURE | Autonom | 1H-NMR | MS (APCI) (M + H)+ |
|---|---|---|---|---|
| 67 | 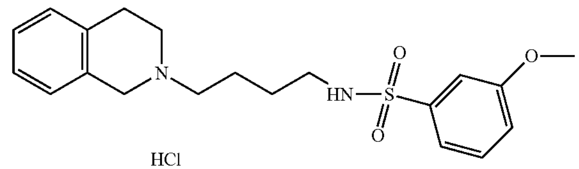 | N-[4-(3,4-Dihydro-1H-isoquinolin-2-yl)-butyl]-3-methoxy-benzenesulfonamide hydrochloride | 1H NMR (300 MHz, DMSO-D6) δ ppm 1.43 (m, 2H), 1.72 (m, 2H), 2.76 (t, J = 6.59 Hz, 2H), 2.98 (m, 1H), 3.12 (m, 3H), 3.26 (m, 1H), 3.63 (m, 1H), 3.77 (s, 3H), 4.22 (dd, J = 15.14, 8.06 Hz, 1H), 4.46 (m, 1H), 7.18 (m, 5H), 7.31 (m, 2H), 7.43 (t, J = 7.93 Hz, 1H), 7.62 (s, 1H), 9.95 (s, 1H) | 375 |
| 68 | 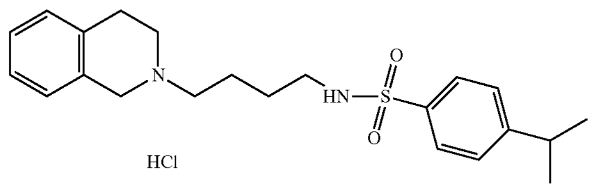 | N-[4-(3,4-Dihydro-1H-isoquinolin-2-yl)-butyl]-4-isopropyl-benzenesulfonamide hydrochloride | | 387 |
| 69 | 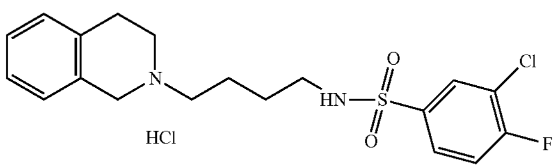 | 3-Chloro-N-[4-(3,4-dihydro-1H-isoquinolin-2-yl)-butyl]-4-fluoro-benzenesulfonamide hydrochloride | 1H NMR (300 MHz, DMSO-D6) δ ppm 1.44 (m, 2H), 1.72 (m, 2H), 2.78 (t, J = 6.84 Hz, 2H), 2.99 (m, 1H), 3.11 (m, 3H), 3.27 (m, 1H), 3.65 (m, 1H), 4.23 (m, 1H), 4.47 (m, 4H), 7.19 (m, 4H), 7.56 (t, J = 8.91 Hz, 1H), 7.78 (ddd, J = 8.67, 4.52, 2.20 Hz, 2H), 7.93 (dd, J = 6.84, 2.44 Hz, 1H), 9.82 (s, 1H) | 397 |
| 70 | 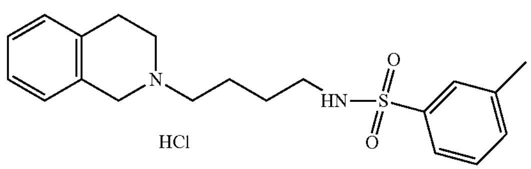 | N-[4-(3,4-Dihydro-1H-isoquinolin-2-yl)-butyl]-3-methyl-benzenesulfonamide hydrochloride | 1H NMR (300 MHz, DMSO-D6) δ ppm 1.44 (m, 2H), 1.72 (m, 2H), 2.37 (s, 3H), 2.75 (m, 2H), 3.00 (m, 1H), 3.12 (m, 3H), 3.27 (m, 1H), 3.64 (m, 1H), 4.24 (dd, J = 14.77, 8.42 Hz, 1H), 4.48 (d, J = 14.40 Hz, 1H), 7.24 (d, J = 6.10 Hz, 4H), 7.43 (s, 2H), 7.59 (s, 3H), 9.90 (s, 1H) | 359 |
| 71 | 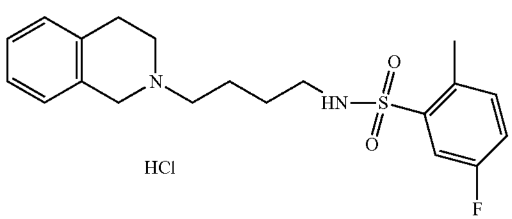 | N-[4-(3,4-Dihydro-1H-isoquinolin-2-yl)-butyl]-5-fluoro-2-methyl-benzenesulfonamide hydrochloride | | 377 |

| N° | STRUCTURE | Autonom | ¹H-NMR | MS (APCI) (M + H)⁺ |
|---|---|---|---|---|
| 72 | 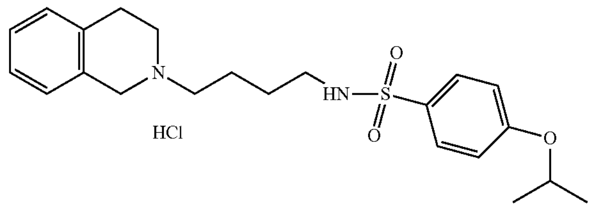 | N-[4-(3,4-Dihydro-1H-isoquinolin-2-yl)-butyl]-4-isopropoxy-benzenesulfonamide hydrochloride | | 403 |
| 73 | 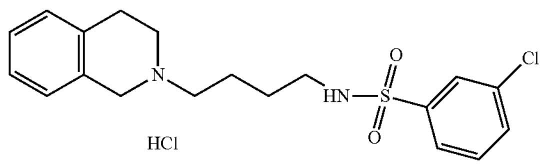 | 3-Chloro-N-[4-(3,4-dihydro-1H-isoquinolin-2-yl)-butyl]-benzenesulfonamide hydrochloride | | 379 |
| 74 | 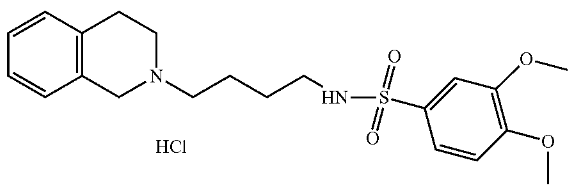 | N-[4-(3,4-Dihydro-1H-isoquinoline-2-yl)-butyl]-3,4-dimethoxy-benzenesulfonamide hydrochloride | | 405 |
| 75 | 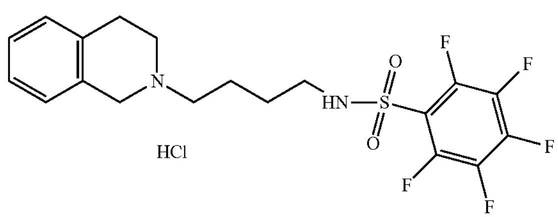 | N-[4-(3,4-Dihydro-1H-isoquinolin-2-yl)-butyl]-2,3,4,5,6-pentafluoro-benzenesulfonamide hydrochloride | | 435 |
| 76 | 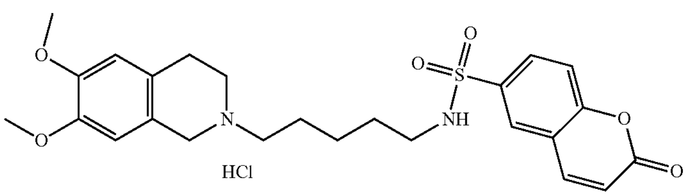 | 2-Oxo-2H-chromene-6-sulfonic acid [5-(6,7-dimethoxy-3,4-dihydro-1H-isoquinolin-2-yl)-pentyl]-amide hydrochloride | | 487 |

-continued

| N° | STRUCTURE | Autonom | ¹H-NMR | MS (APCI) (M + H)⁺ |
|---|---|---|---|---|
| 77 | 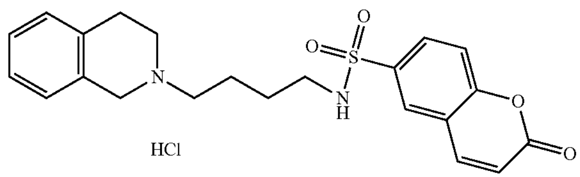 | 2-Oxo-2H-chromene-6-sulfonic acid [4-(3,4-dihydro-1H-isoquinolin-2-yl)-butyl]-amide hydrochloride | | 413 |
| 78 | 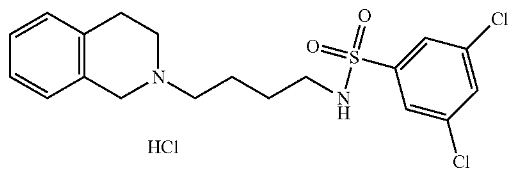 | 3,5-Dichloro-N-[4-(3,4-dihydro-1H-isoquinolin-2-yl)-butyl]-benzenesulfonamide hydrochloride | | 413 |
| 79 | 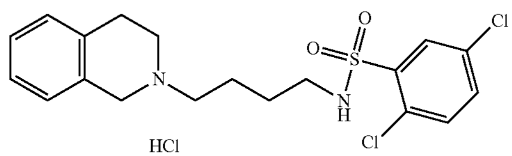 | 2,5-Dichloro-N-[4-(3,4-dihydro-1H-isoquinolin-2-yl)-butyl]-benzenesulfonamide hydrochloride | 1H NMR (300 MHz, DMSO-D6) δ ppm 1.45 (m, 2H), 1.75 (m, 2H), 2.89 (q, J = 6.74 Hz, 2H), 2.96 (m, 1H), 3.10 (m, 3H), 3.21 (m, 1H), 3.63 (m, 1H), 4.21 (dd, J = 15.23, 8.05 Hz, 1H), 4.44 (d, J = 14.94 Hz, 1H), 7.22 (m, 4H), 7.73 (m, 2H), 7.91 (d, J = 2.34 Hz, 1H), 8.19 (t, J = 5.71 Hz, 1H), 10.62 (s, 1H) | 413 |
| 80 | 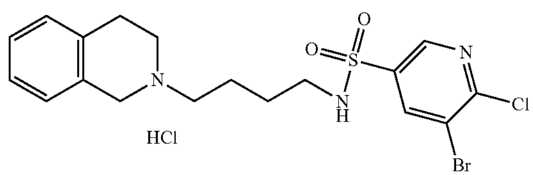 | 5-Bromo-6-chloro-pyridine-3-sulfonic acid [4-(3,4-dihydro-1H-isoquinolin-2-yl)-butyl]-amide hydrochloride | | 458 |
| 81 | 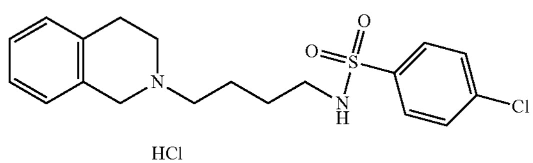 | 4-Chloro-N-[4-(3,4-dihydro-1H-isoquinolin-2-yl)-butyl]-benzenesulfonamide hydrochloride | 1H NMR (300 MHz, DMSO-D6) δ ppm 1.43 (m, 2H), 1.74 (m, 2H), 2.76 (q, J = 6.74 Hz, 2H), 2.98 (m, 1H), 3.10 (m, 3H), 3.14 (m, 1H), 3.63 (m, 1H), 4.21 (dd, J = 15.74, 7.83 Hz, 1H), 4.44 (d, J = 14.06 Hz, 1H), 7.21 (m, 4H), 7.67 (ddd, J = 8.86, 2.42, 2.20 Hz, 2H), 7.79 (ddd, J = 8.86, 2.42, 2.20 Hz, 2H), 7.84 (t, J = 5.86 Hz, 1H), 10.62 (s, 1H) | 379 |

-continued

| N° | STRUCTURE | Autonom | ¹H-NMR | MS (APCI) (M + H)⁺ |
|---|---|---|---|---|
| 82 | 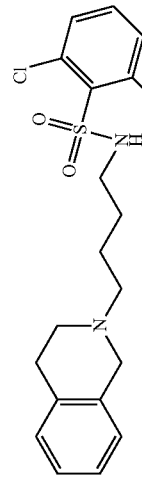 | 2,6-Dichloro-N-[4-(3,4-dihydro-1H-isoquinolin-2-yl)-butyl]-benzenesulfonamide hydrochloride | | 413 |
| 83 | 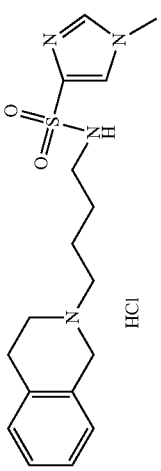 | 1-Methyl-1H-imidazole-4-sulfonic acid [4-(3,4-dihydro-1H-isoquinolin-2-yl)-butyl]-amide hydrochloride | | 349 |
| 84 | 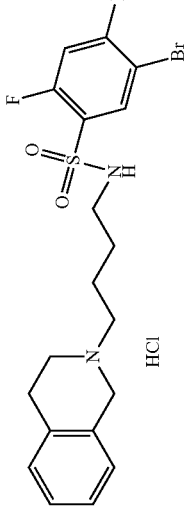 | 5-Bromo-N-[4-(3,4-dihydro-1H-isoquinolin-2-yl)-butyl]-2,4-difluoro-benzenesulfonamide hydrochloride | | 459 |
| 85 | 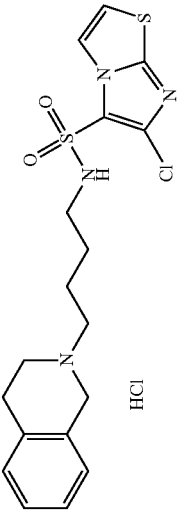 | 6-Chloro-imidazo[2,1-b]thiazole-5-sulfonic acid [4-(3,4-dihydro-1H-isoquinolin-2-yl)-butyl]-amide hydrochloride | | 425 |
| 86 | 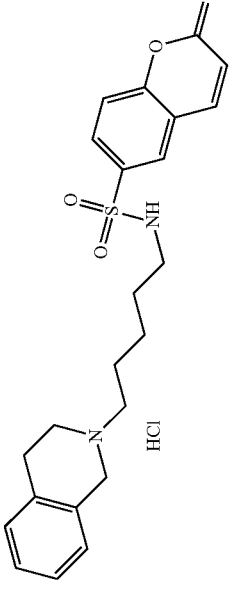 | 2-Oxo-2H-chromene-6-sulfonic acid [5-(3,4-dihydro-1H-isoquinolin-2-yl)-pentyl]-amide hydrochloride | | 427 |

| N° | STRUCTURE | Autonom | ¹H-NMR | MS (APCI) (M+H)⁺ |
|---|---|---|---|---|
| 87 | 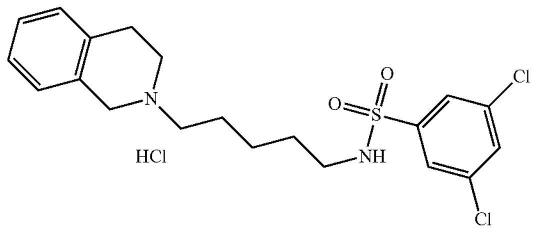 | 3,5-Dichloro-N-[5-(3,4-dihydro-1H-isoquinolin-2-yl)-pentyl]-benzenesulfonamide hydrochloride | | 427 |
| 88 | 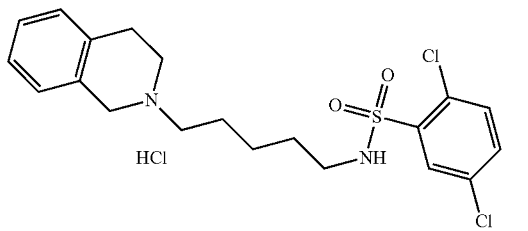 | 2,5-Dichloro-N-[5-(3,4-dihydro-1H-isoquinolin-2-yl)-pentyl]-benzenesulfonamide hydrochloride | 1H NMR (300 MHz, DMSO-D6) δ ppm 1.28 (m, 2H), 1.42 (m, 2H), 1.70 (m, 2H), 2.88 (m, 2H), 2.98 (m, 1H), 3.08 (m, 3H), 3.20 (m, 1H), 3.66 (m, 1H), 4.22 (dd, J = 15.45, 5.78 Hz, 1H), 4.47 (m, 1H), 7.21 (m, 4H), 7.71 (m, 2H), 7.91 (s, 1H), 8.12 (t, J = 5.42 Hz, 1H), 10.59 (s, 1H) | 427 |
| 89 | 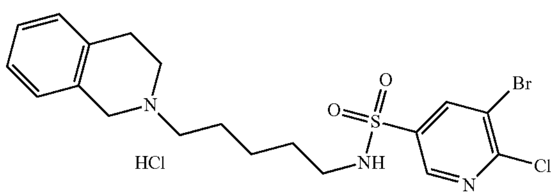 | 5-Bromo-6-chloro-pyridine-3-sulfonic acid [5-(3,4-dihydro-1H-isoquinolin-2-yl)-pentyl]-amide | | 473 |
| 90 | 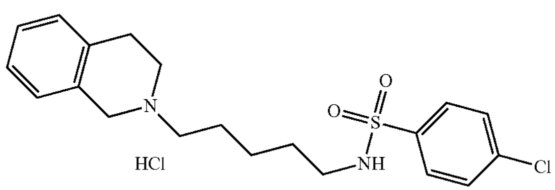 | 4-Chloro-N-[5-(3,4-dihydro-1H-isoquinolin-2-yl)-pentyl]-benzenesulfonamide hydrochloride | | 393 |

-continued

| N° | STRUCTURE | Autonom | ¹H-NMR | MS (APCI) (M + H)⁺ |
|---|---|---|---|---|
| 91 | 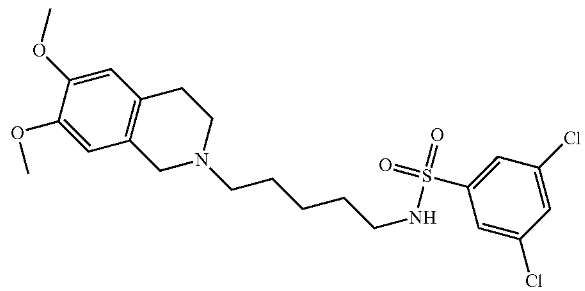 | 3,5-Dichloro-N-[5-(6,7-dimethoxy-3,4-dihydro-1H-isoquinolin-2-yl)-pentyl]-benzenesulfonamide | | 487 |
| 92 | 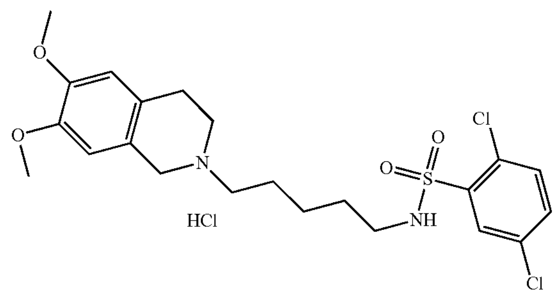 | 2,5-Dichloro-N-[5-(6,7-dimethoxy-3,4-dihydro-1H-isoquinolin-2-yl)-pentyl]-benzenesulfonamide hydrochloride | | 487 |
| 93 | 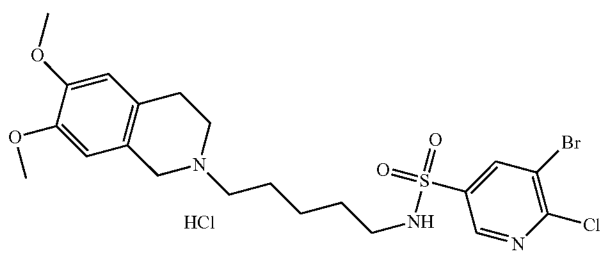 | 5-Bromo-6-chloro-pyridine-3-sulfonic acid [5-(6,7-dimethoxy-3,4-dihydro-1H-isoquinolin-2-yl)-pentyl]-amide hydrochloride | | 532 |

-continued

| N° | STRUCTURE | Autonom | ¹H-NMR | MS (APCI) (M + H)⁺ |
|---|---|---|---|---|
| 94 | 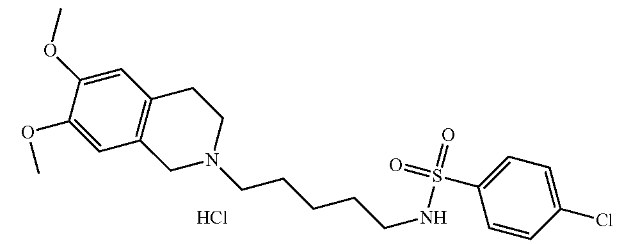 | 4-Chloro-N-[5-(6,7-dimethoxy-3,4-dihydro-1H-isoquinolin-2-yl)-pentyl]-benzenesulfonamide hydrochloride | | 453 |
| 95 | 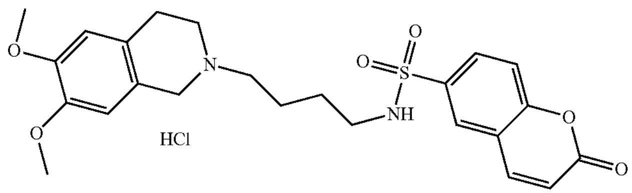 | 2-Oxo-2H-chromene-6-sulfonic acid [4-(6,7-dimethoxy-3,4-dihydro-1H-isoquinolin-2-yl)-butyl]-amide hydrochloride | | 473 |
| 96 | 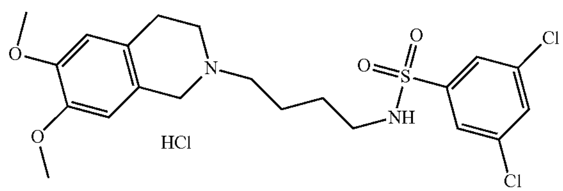 | 3,5-Dichloro-N-[4-(6,7-dimethoxy-3,4-dihydro-1H-isoquinolin-2-yl)-butyl]-benzenesulfonamide hydrochloride | | 473 |
| 97 | 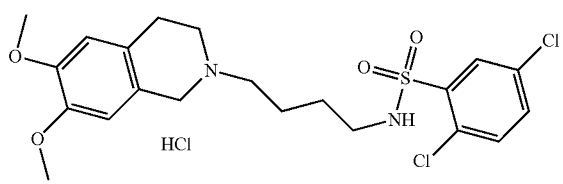 | 2,5-Dichloro-N-[4-(6,7-dimethoxy-3,4-dihydro-1H-isoquinolin-2-yl)-butyl]-benzenesulfonamide hydrochloride | 1H NMR (300 MHz, DMSO-D6) δ ppm 1.46 (m, 2H), 1.74 (m, 2H), 2.89 (m, 3H), 3.06 (m, 3H), 3.23 (m, 1H), 3.57 (m, 1H), 3.70 (s, 3H), 3.72 (s, 3H), 4.09 (m, 1H), 4.33 (d, J = 14.94 Hz, 1H), 6.77 (d, J = 11.27 Hz, 2H), 7.73 (m, 2H), 7.91 (d, J = 2.20 Hz, 1H), 8.18 (t, J = 5.71 Hz, 1H), 10.49 (s, 1H) | 473 |
| 98 | 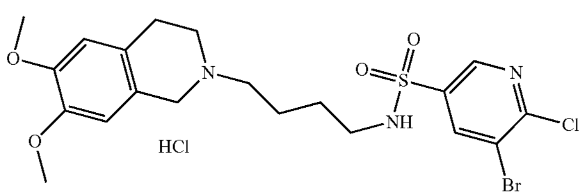 | 5-Bromo-6-chloro-pyridine-3-sulfonic acid [4-(6,7-dimethoxy-3,4-dihydro-1H-isoquinolin-2-yl)-butyl]-amide hydrochloride | | 518 |

-continued

| N° | STRUCTURE | Autonom | ¹H-NMR | MS (APCI) (M + H)⁺ |
|---|---|---|---|---|
| 99 | 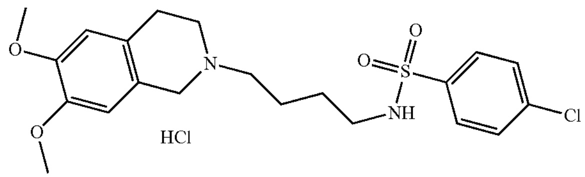 | 4-Chloro-N-[4-(6,7-dimethoxy-3,4-dihydro-1H-isoquinolin-2-yl)-butyl]-benzenesulfonamide hydrochloride | | 439 |
| 100 | 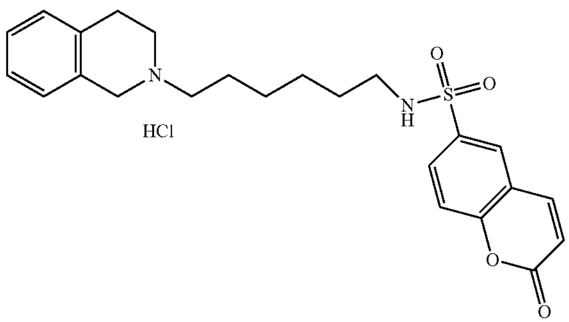 | 2-Oxo-2H-chromene-6-sulfonic acid [6-(3,4-dihydro-1H-isoquinolin-2-yl)-hexyl]-amide hydrochloride | | 441 |
| 101 | 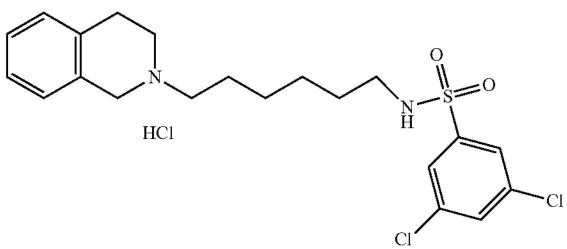 | 3,5-Dichloro-N-[6-(3,4-dihydro-1H-isoquinolin-2-yl)-hexyl]-benzenesulfonamide hydrochloride | | 441 |
| 102 | 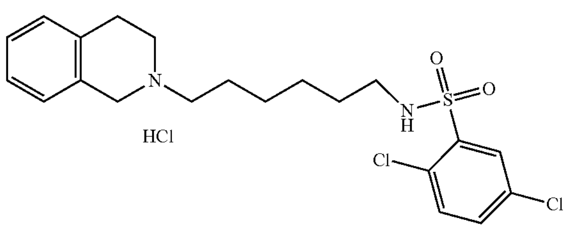 | 2,5-Dichloro-N-[6-(3,4-dihydro-1H-isoquinolin-2-yl)-hexyl]-benzenesulfonamide hydrochloride | | 441 |

| N° | STRUCTURE | Autonom | ¹H-NMR | MS (APCI) (M+H)⁺ |
|---|---|---|---|---|
| 103 | 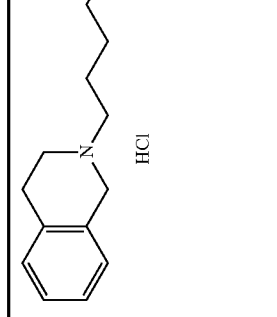 | 5-Bromo-6-chloro-pyridine-3-sulfonic acid [6-(3,4-dihydro-1H-isoquinolin-2-yl)-hexyl]-amide hydrochloride | | 486 |
| 104 | 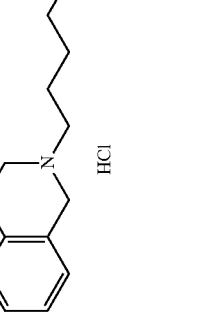 | 2,6-Dichloro-N-[6-(3,4-dihydro-1H-isoquinolin-2-yl)-hexyl]-benzenesulfonamide hydrochloride | | 441 |
| 105 | 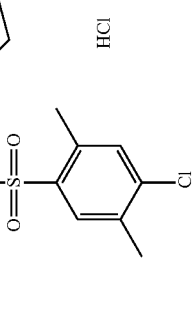 | N-[5-(3,4-Dihydro-1H-isoquinolin-2-yl)-pentyl]-2-methyl-5-nitro-benzenesulfonamide hydrochloride | | 418 |
| 106 | 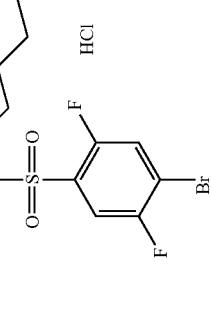 | 4-Bromo-N-[5-(3,4-dihydro-1H-isoquinolin-2-yl)-pentyl]-2,5-difluoro-benzenesulfonamide hydrochloride | | 473 |

-continued

| N° | STRUCTURE | Autonom | ¹H-NMR | MS (APCI) (M + H)⁺ |
|---|---|---|---|---|
| 107 | 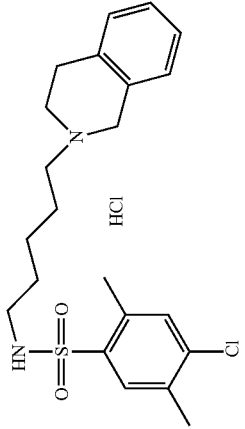 | 4-Chloro-N-[5-(3,4-dihydro-1H-isoquinolin-2-yl)-pentyl]-2,5-dimethyl-benzenesulfonamide hydrochloride | | 421 |
| 108 | 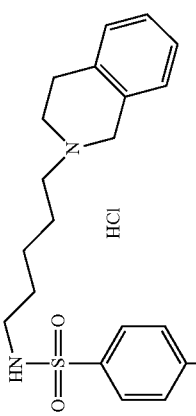 | N-[5-(3,4-Dihydro-1H-isoquinolin-2-yl)-pentyl]-4-isopropyl-benzenesulfonamide hydrochloride | | 401 |
| 109 | 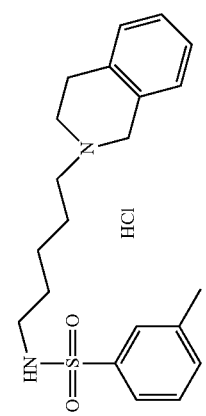 | N-[5-(3,4-Dihydro-1H-isoquinolin-2-yl)-pentyl]-3-methyl-benzenesulfonamide hydrochloride | | 373 |
| 110 | 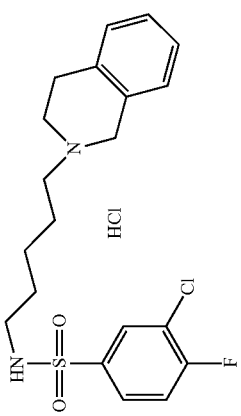 | 3-Chloro-N-[5-(3,4-dihydro-1H-isoquinolin-2-yl)-pentyl]-4-fluoro-benzenesulfonamide hydrochloride | | 411 |

| N° | STRUCTURE | Autonom | ¹H-NMR | MS (APCI) (M + H)⁺ |
|---|---|---|---|---|
| 111 | (structure) HCl | N-[5-(3,4-Dihydro-1H-isoquinolin-2-yl)-pentyl]-5-fluoro-2-methyl-benzenesulfonamide hydrochloride | | 391 |
| 112 | (structure) HCl | N-[5-(3,4-Dihydro-1H-isoquinolin-2-yl)-pentyl]-3-methoxy-benzenesulfonamide hydrochloride | | 389 |
| 113 | (structure) HCl | 3-Chloro-N-[5-(3,4-dihydro-1H-isoquinolin-2-yl)-pentyl]-benzenesulfonamide hydrochloride | | 393 |
| 114 | (structure) HCl | N-[5-(3,4-Dihydro-1H-isoquinolin-2-yl)-pentyl]-3,4-dimethoxy-benzenesulfonamide hydrochloride | | 419 |

| N° | STRUCTURE | Autonom | ¹H-NMR | MS (APCI) (M + H)⁺ |
|---|---|---|---|---|
| 115 | 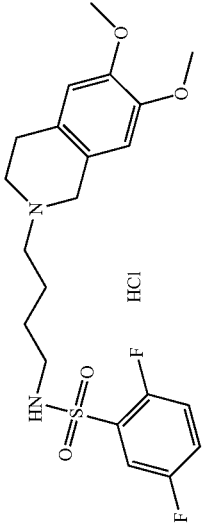 | N-[4-(6,7-Dimethoxy-3,4-dihydro-1H-isoquinolin-2-yl)-butyl]-2,5-difluoro-benzenesulfonamide hydrochloride | | 441 |
| 116 | 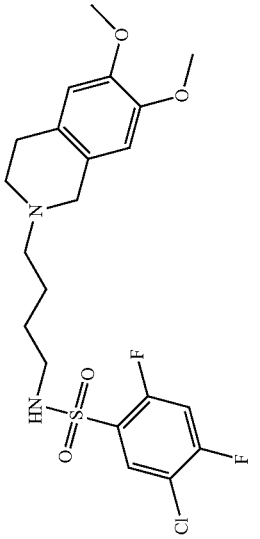 | 5-Chloro-N-[4-(6,7-dimethoxy-3,4-dihydro-1H-isoquinolin-2-yl)-butyl]-2,4-difluoro-benzenesulfonamide hydrochloride | 1H NMR (300 MHz, DMSO-D6) δ ppm 1.42 (m, 4H), 2.30 (m, 2H), 2.52 (m, 2H), 2.63 (m, 2H), 2.89 (m, 2H), 3.23 (m, 2H), 3.65 (s, 3H), 3.66 (s, 3H), 6.56 (s, 1H), 6.61 (s, 1H), 7.80 (t, J = 9.66 Hz, 1H), 7.89 (t, J = 7.69 Hz, 1H), 8.20 (s, 1H) | 475 |
| 117 | 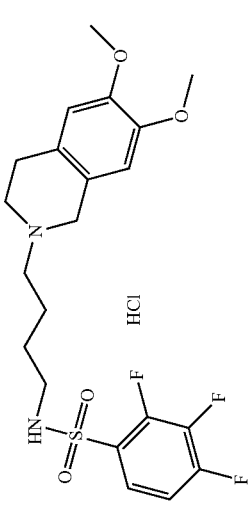 | N-[4-(6,7-Dimethoxy-3,4-dihydro-1H-isoquinolin-2-yl)-butyl]-2,3,4-trifluoro-benzenesulfonamide hydrochloride | | 459 |
| 118 | 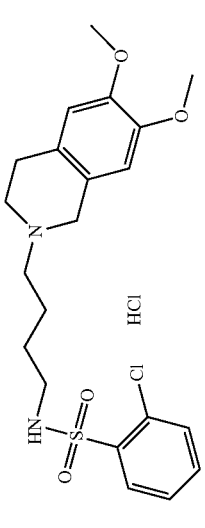 | 2-Chloro-N-[4-(6,7-dimethoxy-3,4-dihydro-1H-isoquinolin-2-yl)-butyl]-benzenesulfonamide hydrochloride | 1H NMR (300 MHz, DMSO-D6) δ ppm 1.44 (m, 2H), 1.70 (m, 2H), 2.86 (m, 3H), 3.07 (m, 2H), 3.18 (m, 2H), 3.56 (m, 1H), 3.70 (s, 3H), 3.71 (s, 3H), 4.10 (dd, J = 14.86, 7.25 Hz, 1H), 4.33 (m, 1H), 6.77 (d, J = 11.57 Hz, 2H), 7.53 (m, 1H), 7.65 (ddd, J = 14.86, 7.98, 1.76 Hz, 2H), 7.97 (m, 2H), 10.40 (s, 1H) | 439 |

| N° | STRUCTURE | Autonom | ¹H-NMR | MS (APCI) (M + H)⁺ |
|---|---|---|---|---|
| 119 | 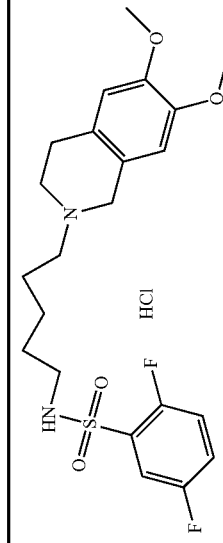 | N-[5-(6,7-Dimethoxy-3,4-dihydro-1H-isoquinolin-2-yl)-pentyl]-2,5-difluoro-benzenesulfonamide hydrochloride | | 455 |
| 120 | 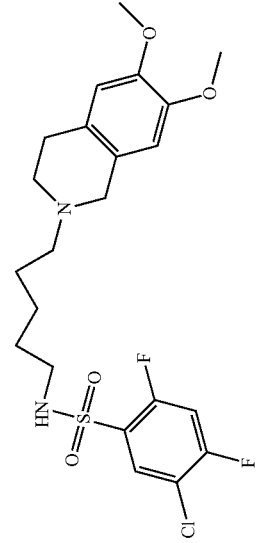 | 5-Chloro-N-[5-(6,7-dimethoxy-3,4-dihydro-1H-isoquinolin-2-yl)-pentyl]-2,4-difluoro-benzenesulfonamide | | 489 |
| 121 | 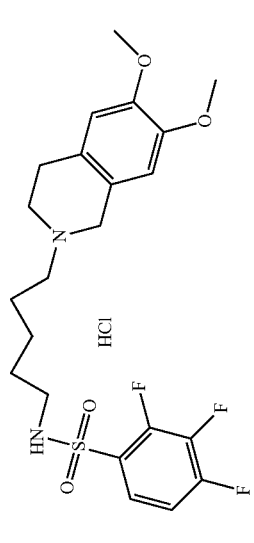 | N-[5-(6,7-Dimethoxy-3,4-dihydro-1H-isoquinolin-2-yl)-pentyl]-2,3,4-trifluoro-benzenesulfonamide hydrochloride | | 473 |
| 122 | 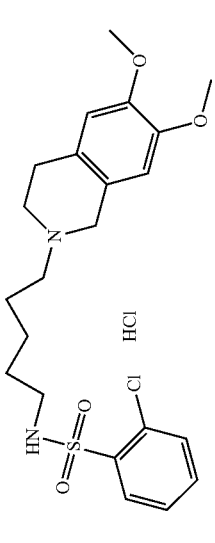 | 2-Chloro-N-[5-(6,7-dimethoxy-3,4-dihydro-1H-isoquinolin-2-yl)-pentyl]-benzenesulfonamide hydrochloride | | 453 |

| N° | STRUCTURE | Autonom | ¹H-NMR | MS (APCI) (M + H)⁺ |
|---|---|---|---|---|
| 123 | 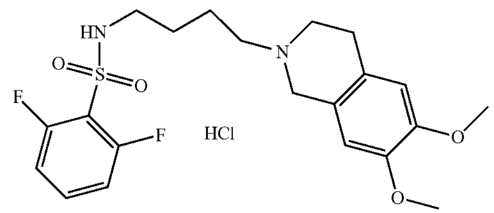 | N-[4-(6,7-Dimethoxy-3,4-dihydro-1H-isoquinolin-2-yl)-butyl]-2,6-difluoro-benzenesulfonamide hydrochloride | | 441 |
| 124 | 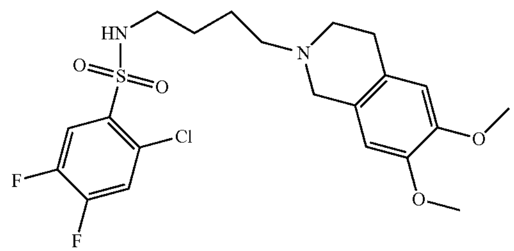 | 2-Chloro-N-[4-(6,7-dimethoxy-3,4-dihydro-1H-isoquinolin-2-yl)-butyl]-4,5-difluoro-benzenesulfonamide | | 475 |
| 125 | 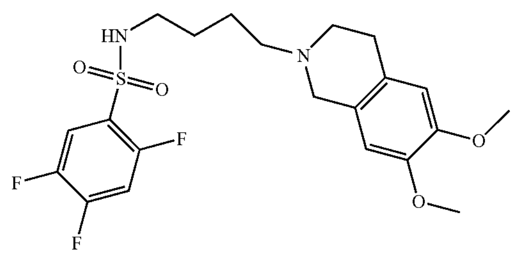 | N-[4-(6,7-Dimethoxy-3,4-dihydro-1H-isoquinolin-2-yl)-butyl]-2,4,5-trifluoro-benzenesulfonamide | | 459 |
| 126 | 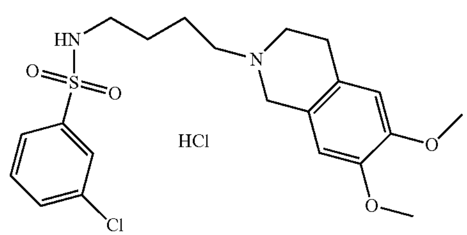 | 3-Chloro-N-[4-(6,7-dimethoxy-3,4-dihydro-1H-isoquinolin-2-yl)-butyl]-benzenesulfonamide hydrochloride | 1H NMR (300 MHz, DMSO-D6) δ ppm 1.44 (m, 2H), 1.74 (m, 2H), 2.78 (q, J = 6.59 Hz, 2H), 2.89 (m, 1H), 3.09 (m, 3H), 3.19 (m, 1H), 3.59 (m, 1H), 3.70 (s, 3H), 3.72 (s, 3H), 4.09 (m, 1H), 4.35 (m, 1H), 6.78 (d, J = 9.52 Hz, 2H), 7.64 (m, 1H), 7.75 (m, 3H), 7.90 (t, J = 5.78 Hz, 1H), 10.47 (s, 1H) | 439 |

-continued

| N° | STRUCTURE | Autonom | ¹H-NMR | MS (APCI) (M + H)⁺ |
|---|---|---|---|---|
| 127 | 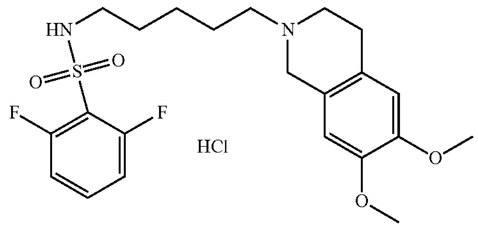 | N-[5-(6,7-Dimethoxy-3,4-dihydro-1H-isoquinolin-2-yl)-pentyl]-2,6-difluoro-benzenesulfonamide hydrochloride | | 455 |
| 128 | 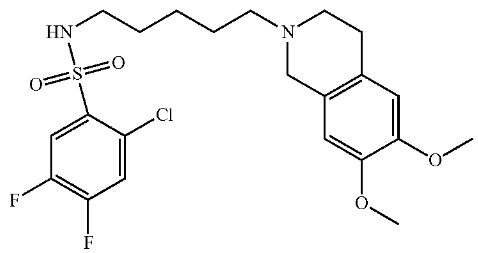 | 2-Chloro-N-[5-(6,7-dimethoxy-3,4-dihydro-1H-isoquinolin-2-yl)-pentyl]-4,5-difluoro-benzenesulfonamide | | 489 |
| 129 | 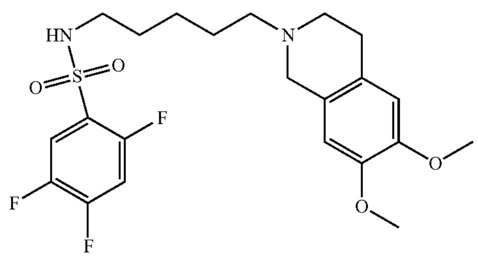 | N-[5-(6,7-Dimethoxy-3,4-dihydro-1H-isoquinolin-2-yl)-pentyl]-2,4,5-trifluoro-benzenesulfonamide | | 473 |
| 130 | 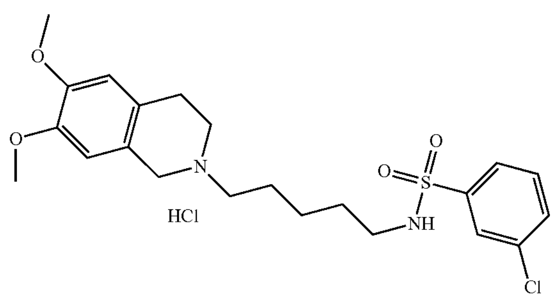 | 3-Chloro-N-[5-(6,7-dimethoxy-3,4-dihydro-1H-isoquinolin-2-yl)-pentyl]-benzenesulfonamide hydrochloride | | 453 |

-continued

| N° | STRUCTURE | Autonom | ¹H-NMR | MS (APCI) (M + H)⁺ |
|---|---|---|---|---|
| 131 | 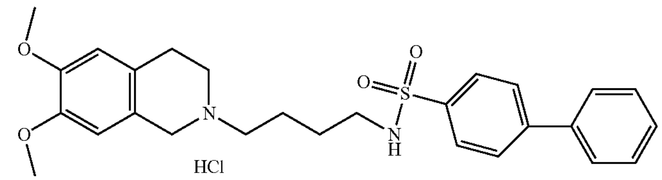 | Biphenyl-4-sulfonic acid [4-(6,7-dimethoxy-3,4-dihydro-1H-isoquinolin-2-yl)-butyl]-amide hydrochloride | | 481 |
| 132 | 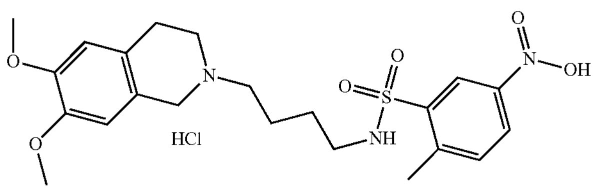 | N-[4-(6,7-Dimethoxy-3,4-dihydro-1H-isoquinolin-2-yl)-butyl]-2-methyl-5-nitro-benzenesulfonamide hydrochloride | | 464 |
| 133 | 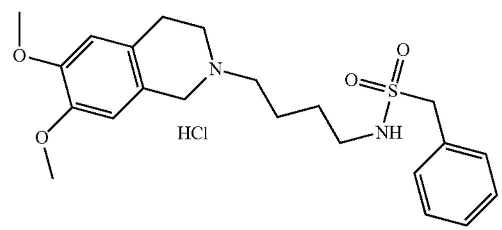 | N-[4-(6,7-Dimethoxy-3,4-dihydro-1H-isoquinolin-2-yl)-butyl]-C-phenyl-methanesulfonamide hydrochloride | | 419 |
| 134 | 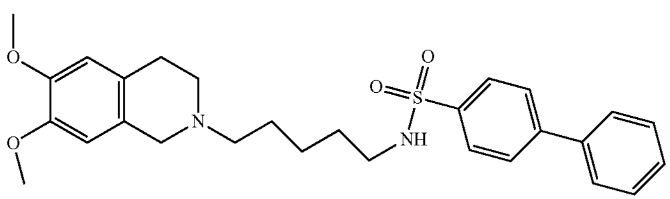 | Biphenyl-4-sulfonic acid [5-(6,7-dimethoxy-3,4-dihydro-1H-isoquinolin-2-yl)-pentyl]-amide | | 495 |

-continued

| N° | STRUCTURE | Autonom | 1H-NMR | MS (APCI) (M + H)+ |
|---|---|---|---|---|
| 135 | 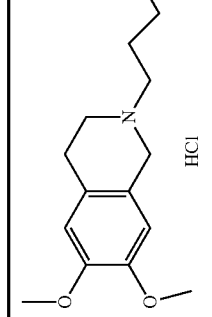 | N-[5-(6,7-Dimethoxy-3,4-dihydro-1H-isoquinolin-2-yl)-pentyl]-C-phenyl-methanesulfonamide hydrochloride | | 433 |
| 136 | 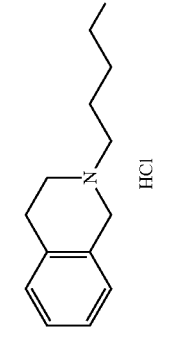 | Benzo[b]thiophene-3-sulfonic acid [4-(3,4-dihydro-1H-isoquinolin-2-yl)-butyl]-amide hydrochloride | | 401 |
| 137 | 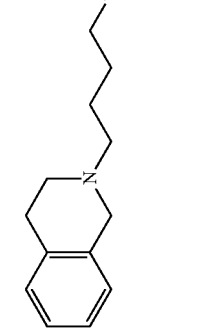 | 7-Chloro-benzo[1,2,5]oxadiazole-4-sulfonic acid [4-(3,4-dihydro-1H-isoquinolin-2-yl)-butyl]-amide | | 421 |
| 138 | 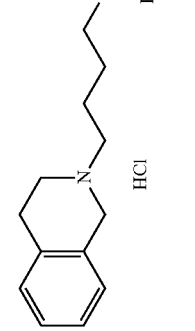 | N-[4-(3,4-Dihydro-1H-isoquinolin-2-yl)-butyl]-2,4-dinitro-benzenesulfonamide hydrochloride | | 435 |
| 139 | 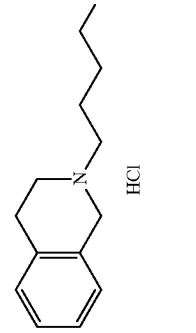 | Benzo[b]thiophene-2-sulfonic acid [4-(3,4-dihydro-1H-isoquinolin-2-yl)-butyl]-amide hydrochloride | | 401 |

| N° | STRUCTURE | Autonom | 1H-NMR | MS (APCI) (M + H)+ |
|---|---|---|---|---|
| 140 | 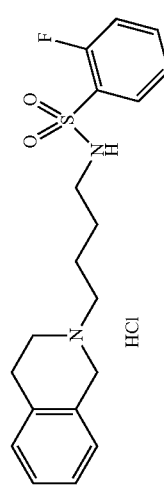 | N-[4-(3,4-Dihydro-1H-isoquinolin-2-yl)-butyl]-2,5-difluoro-benzenesulfonamide hydrochloride | 1H NMR (300 MHz, DMSO-D6) δ ppm 1.46 (m, 2H), 1.75 (m, 2H), 2.90 (m, 2H), 3.01 (m, 1H), 3.13 (m, 3H), 3.24 (m, 1H), 3.64 (m, 1H), 4.21 (m, 1H), 4.45 (m, 1H), 7.23 (m, 4H), 7.56 (m, 3H), 8.19 (t, J = 5.64 Hz, 1H), 10.59 (s, 1H) | 381 |
| 141 | 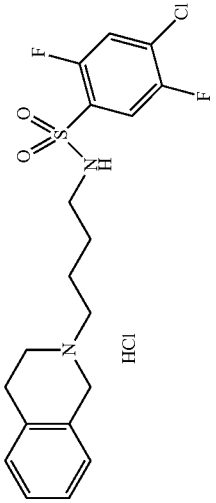 | 4-Chloro-N-[4-(3,4-dihydro-1H-isoquinolin-2-yl)-butyl]-2,5-difluoro-benzenesulfonamide hydrochloride | 1H NMR (300 MHz, DMSO-D6) δ ppm 1.47 (m, 2H), 1.75 (m, 2H), 2.91 (q, J = 6.69 Hz, 2H), 3.01 (m, 1H), 3.12 (m, 2H), 3.23 (m, 2H), 3.64 (m, 1H), 4.21 (dd, J = 14.64, 7.32 Hz, 1H), 4.45 (d, J = 15.67 Hz, 1H), 7.22 (m, 4H), 7.77 (dd, J = 8.27, 6.22 Hz, 1H), 7.97 (dd, J = 9.44, 5.78 Hz, 1H), 8.28 (t, J = 5.78 Hz, 1H), 10.59 (s, 1H) | 415 |
| 142 | 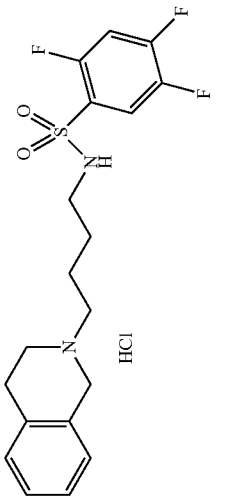 | N-[4-(3,4-Dihydro-1H-isoquinolin-2-yl)-butyl]-2,4,5-trifluoro-benzenesulfonamide hydrochloride | 1H NMR (300 MHz, DMSO-D6) δ ppm 1.45 (m, 2H), 1.74 (m, 2H), 2.92 (m, 3H), 3.15 (m, 2H), 3.24 (m, 2H), 3.63 (m, 1H), 4.21 (dd, J = 15.23, 7.47 Hz, 1H), 4.45 (m, 1H), 7.22 (m, 4H), 7.86 (m, 2H), 8.22 (m, 1H), 10.65 (s, 1H) | 399 |
| 143 | 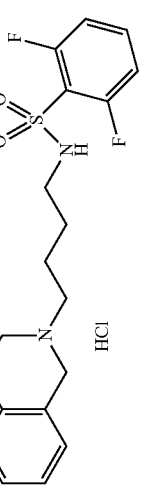 | N-[4-(3,4-Dihydro-1H-isoquinolin-2-yl)-butyl]-2,6-difluoro-benzenesulfonamide hydrochloride | | 381 |

| N° | STRUCTURE | Autonom | 1H-NMR | MS (APCI) (M + H)+ |
|---|---|---|---|---|
| 144 | 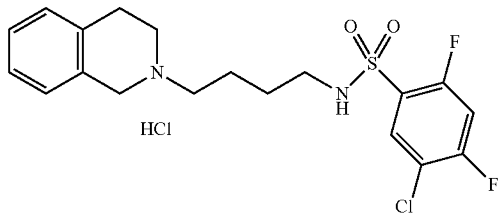 | 5-Chloro-N-[4-(3,4-dihydro-1H-isoquinolin-2-yl)-butyl]-2,4-difluoro-benzenesulfonamide hydrochloride | 1H NMR (300 MHz, DMSO-D6) δ ppm 1.46 (m, 2H), 1.76 (m, 2H), 2.89 (q, J = 6.74 Hz, 2H), 3.01 (m, 1H), 3.18 (m, 4H), 3.61 (m, 1H), 4.21 (dd, J = 15.23, 7.47 Hz, 1H), 4.45 (m, 1H), 7.16 (s, 1H), 7.24 (m, 3H), 7.85 (t, J = 9.66 Hz, 1H), 7.93 (t, J = 7.69 Hz, 1H), 8.24 (t, J = 5.64 Hz, 1H), 10.60 (s, 1H) | 415 |
| 145 | 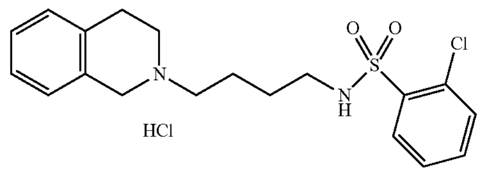 | 2-Chloro-N-[4-(3,4-dihydro-1H-isoquinolin-2-yl)-butyl]-benzenesulfonamide hydrochloride | 1H NMR (300 MHz, DMSO-D6) δ ppm 1.44 (m, 2H), 1.73 (m, 2H), 2.85 (q, J = 6.74 Hz, 2H), 3.01 (m, 1H), 3.09 (m, 2H), 3.23 (m, 2H), 3.59 (m, 1H), 4.20 (m, 1H), 4.43 (m, 1H), 7.22 (m, 4H), 7.53 (m, 2H), 7.63 (m, 2H), 7.96 (m, 2H), 10.57 (s, 1H) | 379 |
| 146 | 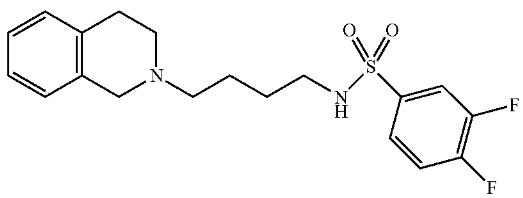 | N-[4-(3,4-Dihydro-1H-isoquinolin-2-yl)-butyl]-3,4-difluoro-benzenesulfonamide | | 381 |
| 147 | 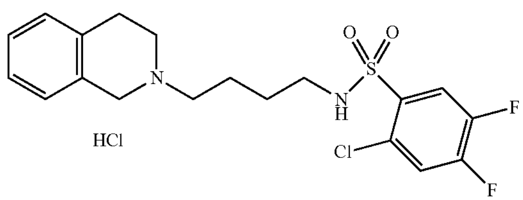 | 2-Chloro-N-[4-(3,4-dihydro-1H-isoquinolin-2-yl)-butyl]-4,5-difluoro-benzenesulfonamide hydrochloride | 1H NMR (300 MHz, DMSO-D6) δ ppm 1.44 (m, 2H), 1.74 (m, 2H), 2.87 (m, 2H), 2.98 (m, 1H), 3.11 (s, 3H), 3.21 (s, 1H), 3.60 (m, 1H), 4.21 (dd, J = 14.28, 6.81 Hz, 1H), 4.44 (m, 1H), 7.22 (m, 4H), 7.98 (m, 2H), 8.19 (d, J = 5.34 Hz, 1H), 10.58 (s, 1H) | 415 |
| 148 | 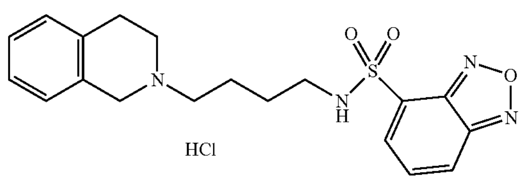 | Benzo[1,2,5]oxadiazole-4-sulfonic acid [4-(3,4-dihydro-1H-isoquinolin-2-yl)-amide hydrochloride | | 387 |

-continued

| N° | STRUCTURE | Autonom | ¹H-NMR | MS (APCI) (M + H)⁺ |
|---|---|---|---|---|
| 149 | 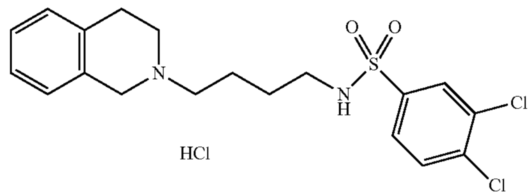 | 3,4-Dichloro-N-[4-(3,4-dihydro-1H-isoquinolin-2-yl)-butyl]-benzenesulfonamide hydrochloride | | 413 |
| 150 | 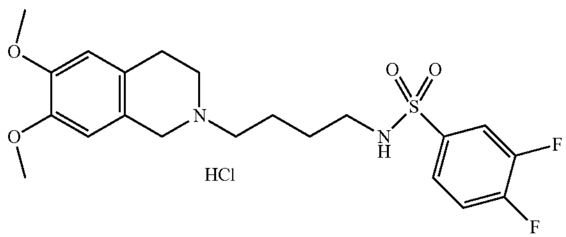 | N-[4-(6,7-Dimethoxy-3,4-dihydro-1H-isoquinolin-2-yl)-butyl]-3,4-difluoro-benzenesulfonamide hydrochloride | | 441 |
| 151 | 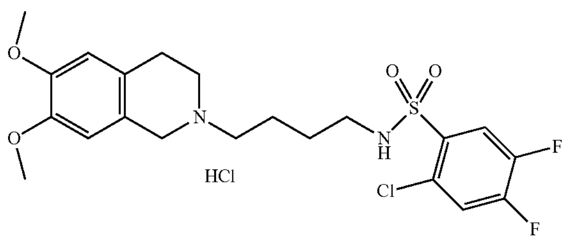 | 2-Chloro-N-[4-(6,7-dimethoxy-3,4-dihydro-1H-isoquinolin-2-yl)-butyl]-4,5-difluoro-benzenesulfonamide hydrochloride | | 475 |
| 152 | 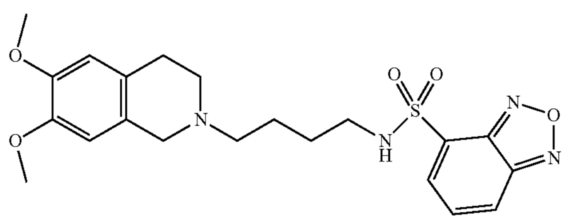 | Benzo[1,2,5]oxadiazole-4-sulfonic acid [4-(6,7-dimethoxy-3,4-dihydro-1H-isoquinolin-2-yl)-butyl]-amide | | 447 |

| N° | STRUCTURE | Autonom | ¹H-NMR | MS (APCI) (M + H)⁺ |
|---|---|---|---|---|
| 153 | 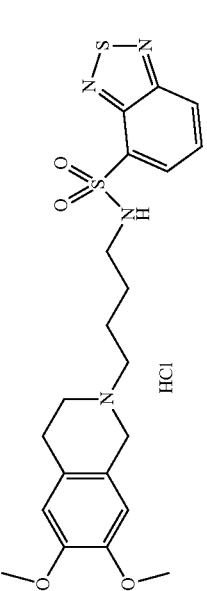 HCl | Benzo[1,2,5]thiadiazole-4-sulfonic acid [4-(6,7-dimethoxy-3,4-dihydro-1H-isoquinolin-2-yl)-butyl]-amide hydrochloride | | 463 |
| 154 | 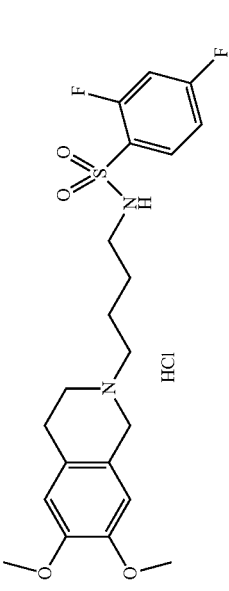 HCl | N-[4-(6,7-Dimethoxy-3,4-dihydro-1H-isoquinolin-2-yl)-butyl]-2,4-difluoro-benzenesulfonamide hydrochloride | 1H NMR (300 MHz, DMSO-D6) δ ppm 1.44 (m, 2H), 1.72 (m, 2H), 2.86 (d, J = 6.44 Hz, 2H), 2.89 (m, 1H), 3.10 (m, 4H), 3.57 (m, 1H), 3.69 (s, 3H), 3.70 (s, 3H), 4.09 (dd, J = 15.08, 7.17 Hz, 1H), 4.32 (d, J = 14.20 Hz, 1H), 6.76 (d, J = 10.25 Hz, 2H), 7.28 (t, J = 8.35 Hz, 1H), 7.53 (m, 1H), 7.83 (m, 1H), 8.05 (t, J = 5.42 Hz, 1H), 10.47 (s, 1H) | 441 |
| 155 | 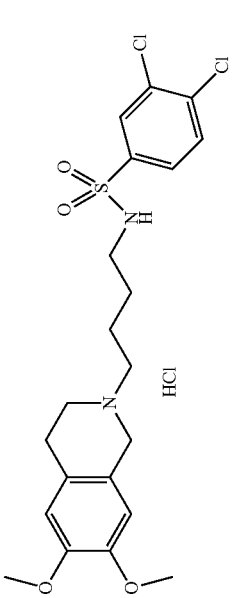 HCl | 3,4-Dichloro-N-[4-(6,7-dimethoxy-3,4-dihydro-1H-isoquinolin-2-yl)-butyl]-benzenesulfonamide hydrochloride | 1H NMR (300 MHz, DMSO-D6) δ ppm 1.44 (m, 2H), 1.73 (m, 2H), 2.77 (m, 2H), 2.88 (m, 1H), 3.09 (m, 4H), 3.58 (m, 1H), 3.69 (s, 3H), 3.70 (s, 3H), 4.09 (m, 1H), 4.34 (m, 1H), 6.76 (d, J = 9.96 Hz, 2H), 7.74 (d, J = 8.20 Hz, 1H), 7.88 (d, J = 7.91 Hz, 1H), 7.97 (s, 2H), 10.47 (s, 1H) | 473 |
| 156 | 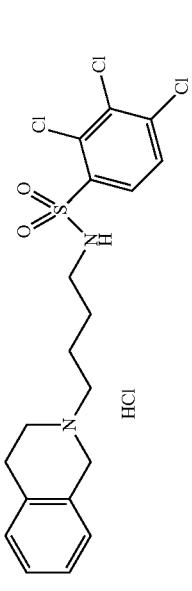 HCl | 2,3,4-Trichloro-N-[4-(3,4-dihydro-1H-isoquinolin-2-yl)-butyl]-benzenesulfonamide hydrochloride | 1H NMR (300 MHz, DMSO-D6) δ ppm 1.46 (m, 2H), 1.75 (m, 2H), 2.87 (m, 2H), 3.00 (m, 1H), 3.14 (d, J = 5.27 Hz, 2H), 3.24 (m, 2H), 3.66 (d, J = 2.34 Hz, 1H), 4.23 (dd, J = 15.52, 7.76 Hz, 1H), 4.46 (d, J = 15.08 Hz, 1H), 7.23 (m, 4H), 7.87 (m, 1H), 7.96 (m, 1H), 8.28 (t, J = 5.56 Hz, 1H), 10.44 (s, 1H) | 447 |

| N° | STRUCTURE | Autonom | ¹H-NMR | MS (APCI) (M + H)⁺ |
|---|---|---|---|---|
| 157 | 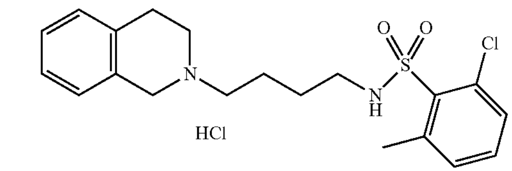 | 2-Chloro-N-[4-(3,4-dihydro-1H-isoquinolin-2-yl)-butyl]-6-methyl-benzenesulfonamide hydrochloride | | 393 |
| 158 | 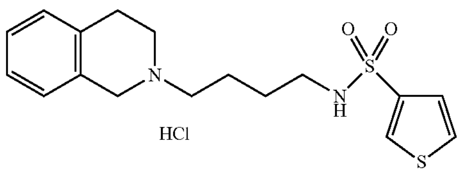 | Thiophene-3-sulfonic acid [4-(3,4-dihydro-1H-isoquinolin-2-yl)-butyl]-amide hydrochloride | 1H NMR (300 MHz, DMSO-D6) δ ppm 1.47 (m, 2H), 1.76 (m, 2H), 2.81 (q, J = 6.39 Hz, 2H), 3.03 (m, 1H), 3.12 (m, 2H), 3.26 (m, 2H), 3.66 (m, 1H), 4.21 (m, 1H), 4.46 (m, 1H), 7.25 (ddd, J = 6.26, 3.51, 3.26 Hz, 4H), 7.20 (m, 1H), 7.25 (m, 3H), 7.33 (m, 1H), 7.66 (m, 1H), 7.76 (dd, J = 5.12, 2.93 Hz, 1H), 8.15 (dd, J = 2.93, 1.32 Hz, 1H), 10.49 (s, 1H) | 351 |
| 159 | 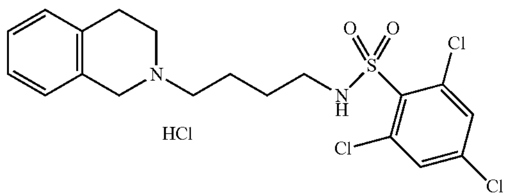 | 2,4,6-Trichloro-N-[4-(3,4-dihydro-1H-isoquinolin-2-yl)-butyl]-benzenesulfonamide hydrochloride | 1H NMR (300 MHz, DMSO-D6) δ ppm 1.49 (m, 2H), 1.77 (m, 2H), 2.93 (q, J = 6.64 Hz, 2H), 3.04 (m, 1H), 3.12 (m, 2H), 3.26 (m, 2H), 3.64 (m, 1H), 4.21 (m, 1H), 4.45 (m, 1H), 7.23 (m, 4H), 7.88 (s, 2H), 8.33 (t, J = 5.71 Hz, 1H), 10.60 (s, 1H) | 447 |
| 160 | 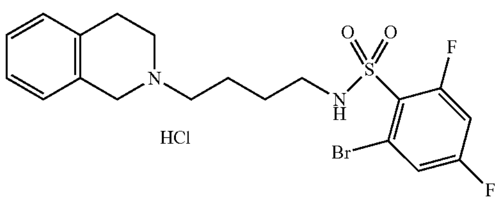 | 2-Bromo-N-[4-(3,4-dihydro-1H-isoquinolin-2-yl)-[4,6-difluoro-benzenesulfonamide hydrochloride | 1H NMR (300 MHz, DMSO-D6) δ ppm 1.49 (m, 2H), 1.76 (m, 2H), 2.94 (q, J = 6.39 Hz, 2H), 3.04 (m, 1H), 3.15 (m, 2H), 3.29 (m, 2H), 3.65 (m, 1H), 4.25 (m, 1H), 4.47 (m, 1H), 7.22 (m, 4H), 7.62 (ddd, J = 11.57, 8.93, 2.64 Hz, 1H), 7.76 (m, 1H), 8.29 (t, J = 5.86 Hz, 1H), 10.28 (s, 1H) | 459 |
| 161 | 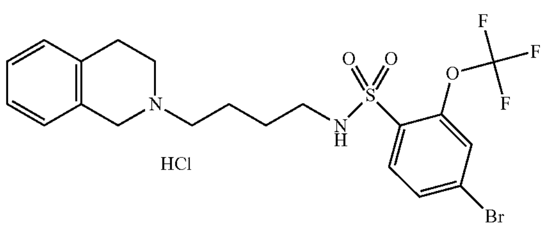 | 4-Bromo-N-[4-(3,4-dihydro-1H-isoquinolin-2-yl)-butyl]-2-trifluoromethoxy-benzenesulfonamide hydrochloride | | 507 |

| N° | STRUCTURE | Autonom | ¹H-NMR | MS (APCI) (M + H)⁺ |
|---|---|---|---|---|
| 162 | 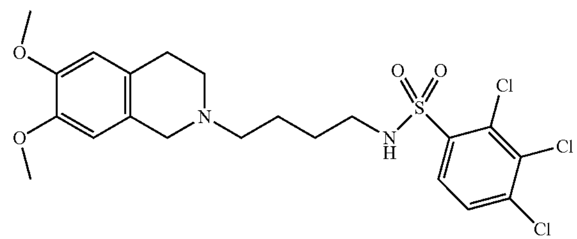 | 2,3,4-Trichloro-N-[4-(6,7-dimethoxy-3,4-dihydro-1H-isoquinolin-2-yl)-butyl]-benzenesulfonamide | | 507 |
| 163 | 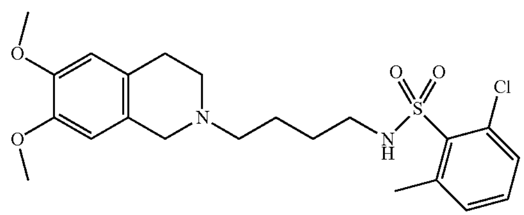 | 2-Chloro-N-[4-(6,7-dimethoxy-3,4-dihydro-1H-isoquinolin-2-yl)-butyl]-6-methyl-benzenesulfonamide | | 453 |
| 164 | 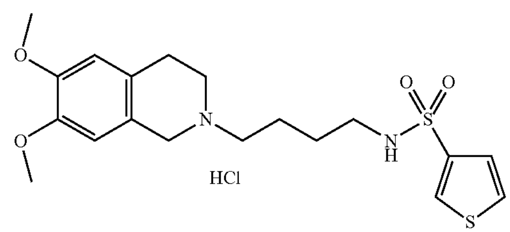 | Thiophene-3-sulfonic acid [4-(6,7-dimethoxy-3,4-dihydro-1H-isoquinolin-2-yl)-butyl]-amide hydrochloride | | 411 |
| 165 | 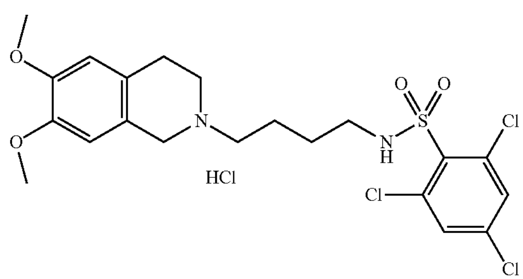 | 2,4,6-Trichloro-N-[4-(6,7-dimethoxy-3,4-dihydro-1H-isoquinolin-2-yl)-butyl]-benzenesulfonamide hydrochloride | | 507 |

| N° | STRUCTURE | Autonom | ¹H-NMR | MS (APCI) (M + H)⁺ |
|---|---|---|---|---|
| 166 | 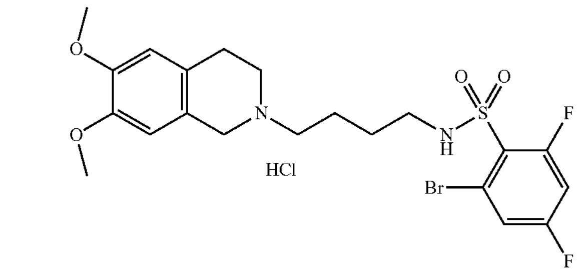 | 2-Bromo-N-[4-(6,7-dimethoxy-3,4-dihydro-1H-isoquinolin-2-yl)-butyl]-4,6-difluoro-benzenesulfonamide hydrochloride | | 519 |
| 167 | 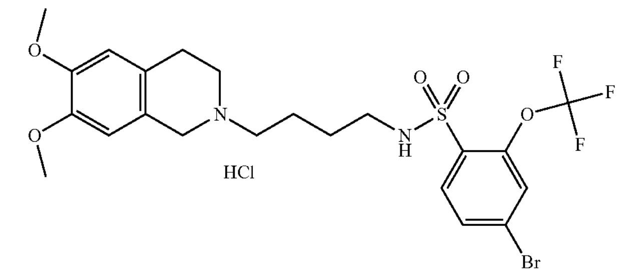 | 4-Bromo-N-[4-(6,7-dimethoxy-3,4-dihydro-1H-isoquinolin-2-yl)-butyl]-2-trifluoromethoxy-benzenesulfonamide hydrochloride | | 567 |
| 168 | 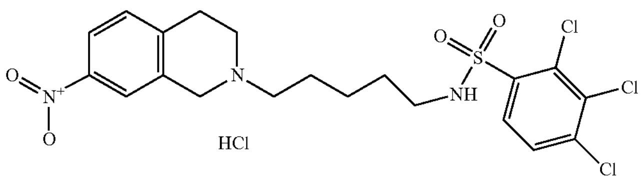 | 2,3,4-Trichloro-N-[5-(7-nitro-3,4-dihydro-1H-isoquinolin-2-yl)-pentyl]-benzenesulfonamide hydrochloride | | 506 |
| 169 | 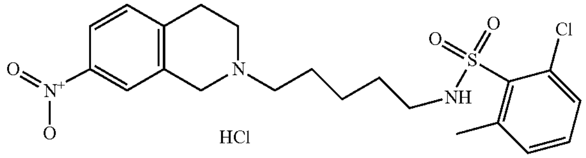 | 2-Chloro-6-methyl-N-[5-(7-nitro-3,4-dihydro-1H-isoquinolin-2-yl)-pentyl]-benzenesulfonamide hydrochloride | | 452 |

| N° | STRUCTURE | Autonom | ¹H-NMR | MS (APCI) (M + H)⁺ |
|---|---|---|---|---|
| 170 | 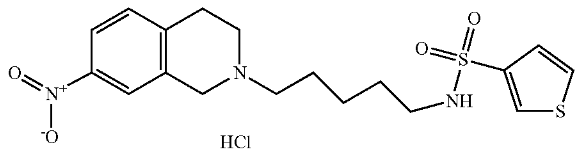 | Thiophene-3-sulfonic acid [5-(7-nitro-3,4-dihydro-1H-isoquinolin-2-yl)-pentyl]-amide hydrochloride | | 410 |
| 171 | 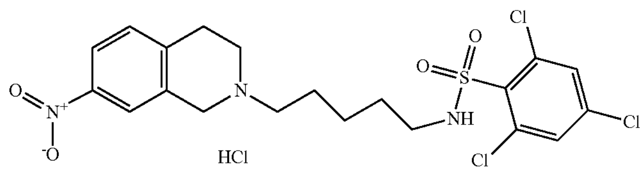 | 2,4,6-Trichloro-N-[5-(7-nitro-3,4-dihydro-1H-isoquinolin-2-yl)-pentyl]-benzenesulfonamide hydrochloride | | 506 |
| 172 | 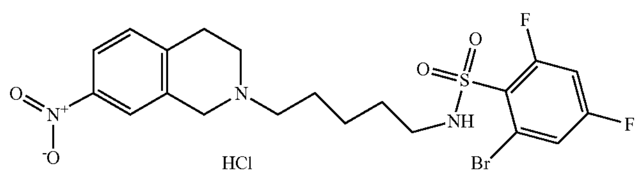 | 2-Bromo-4,6-difluoro-N-[5-(7-nitro-3,4-dihydro-1H-isoquinolin-2-yl)-pentyl]-benzenesulfonamide hydrochloride | | 518 |
| 173 | 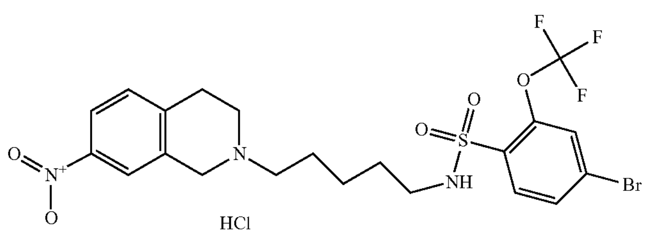 | 4-Bromo-N-[5-(7-nitro-3,4-dihydro-1H-isoquinolin-2-yl)-pentyl]-2-trifluoromethoxy-benzenesulfonamide hydrochloride | | 566 |
| 174 | 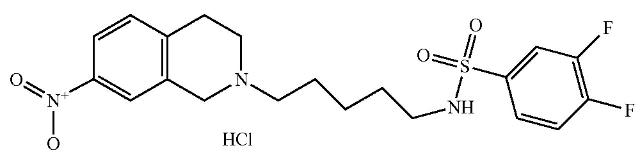 | 3,4-Difluoro-N-[5-(7-nitro-3,4-dihydro-1H-isoquinolin-2-yl)-pentyl]-benzenesulfonamide hydrochloride | | 440 |

| N° | STRUCTURE | Autonom | ¹H-NMR | MS (APCI) (M + H)⁺ |
|---|---|---|---|---|
| 175 | 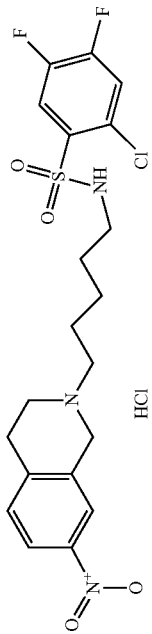 HCl | 2-Chloro-4,5-difluoro-N-[5-(7-nitro-3,4-dihydro-1H-isoquinolin-2-yl)-pentyl]-benzenesulfonamide | | 474 |
| 176 | 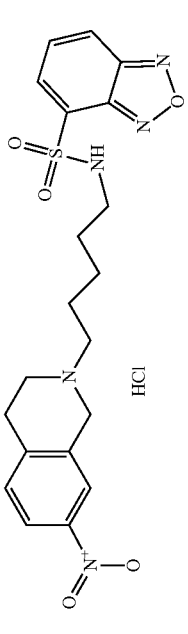 HCl | Benzo[1,2,5]oxadiazole-4-sulfonic acid [5-(7-nitro-3,4-dihydro-1H-isoquinolin-2-yl)-pentyl]-amide hydrochloride | | 446 |
| 177 | 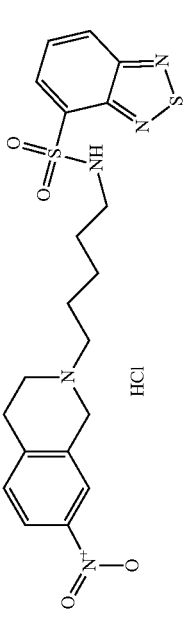 HCl | Benzo[1,2,5]thiadiazole-4-sulfonic acid [5-(7-nitro-3,4-dihydro-1H-isoquinolin-2-yl)-pentyl]-amide hydrochloride | | 462 |
| 178 | 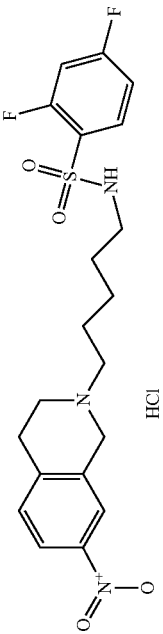 HCl | 2,4-Difluoro-N-[5-(7-nitro-3,4-dihydro-1H-isoquinolin-2-yl)-pentyl]-benzenesulfonamide hydrochloride | | 440 |
| 179 | 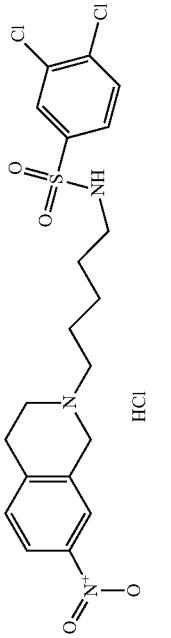 HCl | 3,4-Dichloro-N-[5-(7-nitro-3,4-dihydro-1H-isoquinolin-2-yl)-pentyl]-benzenesulfonamide hydrochloride | | 472 |

| N° | STRUCTURE | Autonom | ¹H-NMR | MS (APCI) (M + H)⁺ |
|---|---|---|---|---|
| 180 | 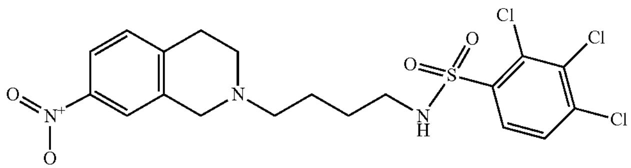 | 2,3,4-Trichloro-N-[4-(7-nitro-3,4-dihydro-1H-isoquinolin-2-yl)-butyl]-benzenesulfonamide | | 494 |
| 181 | 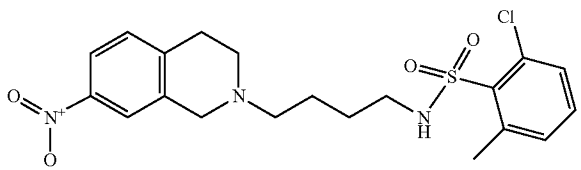 | 2-Chloro-6-methyl-N-[4-(7-nitro-3,4-dihydro-1H-isoquinolin-2-yl)-butyl]-benzenesulfonamide | | 438 |
| 182 | 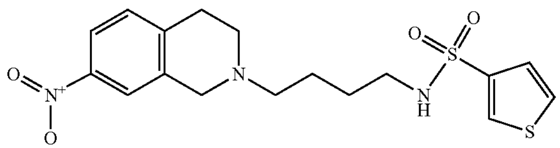 | Thiophene-3-sulfonic acid [4-(7-nitro-3,4-dihydro-1H-isoquinolin-2-yl)-butyl]-amide | | 396 |
| 183 | 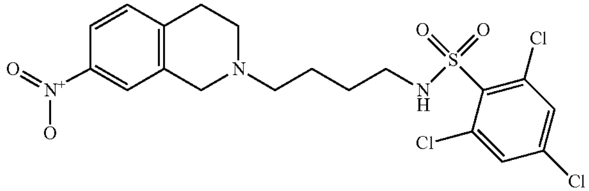 | 2,4,6-Trichloro-N-[4-(7-nitro-3,4-dihydro-1H-isoquinolin-2-yl)-butyl]-benzenesulfonamide | | 492 |
| 184 | 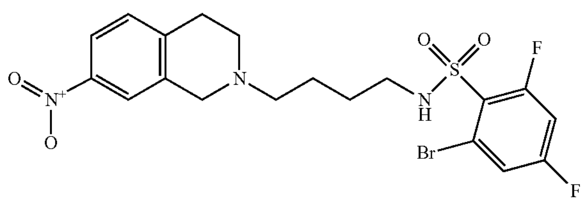 | 2-Bromo-4,6-difluoro-N-[4-(7-nitro-3,4-dihydro-1H-isoquinolin-2-yl)-butyl]-benzenesulfonamide | | 504 |

-continued

| N° | STRUCTURE | Autonom | ¹H-NMR | MS (APCI) (M + H)⁺ |
|---|---|---|---|---|
| 185 | 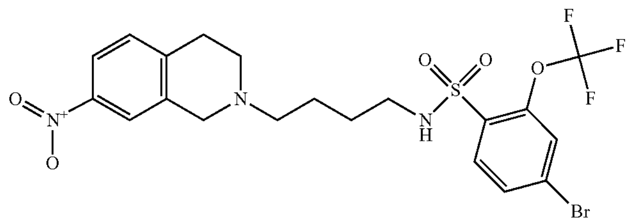 | 4-Bromo-N-[4-(7-nitro-3,4-dihydro-1H-isoquinolin-2-yl)-butyl]-2-trifluoromethoxy-benzenesulfonamide | | 552 |
| 186 | 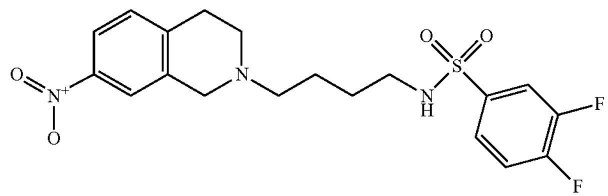 | 3,4-Difluoro-N-[4-(7-nitro-3,4-dihydro-1H-isoquinolin-2-yl)-butyl]-benzenesulfonamide | | 426 |
| 187 | 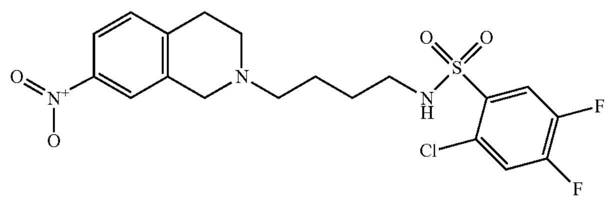 | 2-Chloro-4,5-difluoro-N-[4-(7-nitro-3,4-dihydro-1H-isoquinolin-2-yl)-butyl]-benzenesulfonamide | | 460 |
| 188 | 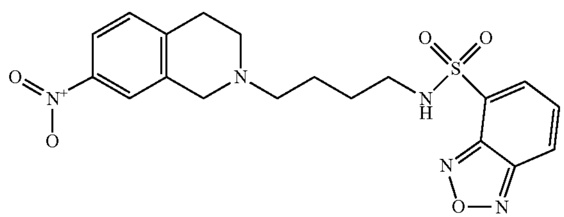 | Benzo[1,2,5]oxadiazole-4-sulfonic acid [4-(7-nitro-3,4-dihydro-1H-isoquinolin-2-yl)-butyl]-amide | | 432 |

-continued

| N° | STRUCTURE | Autonom | ¹H-NMR | MS (APCI) (M + H)⁺ |
|---|---|---|---|---|
| 189 | 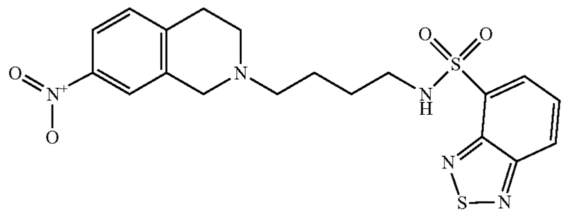 | Benzo[1,2,5]thiadiazole-4-sulfonic acid [4-(7-nitro-3,4-dihydro-1H-isoquinolin-2-yl)-butyl]-amide | | 448 |
| 190 | 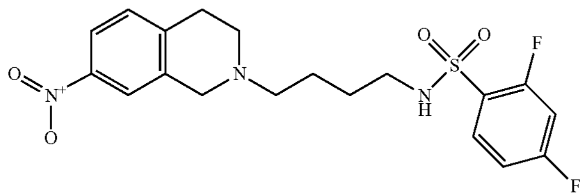 | 2,4-Difluoro-N-[4-(7-nitro-3,4-dihydro-1H-isoquinolin-2-yl)-butyl]-benzenesulfonamide | | 426 |
| 191 | 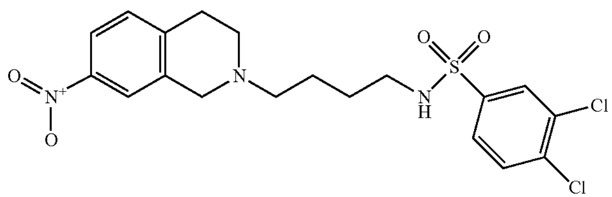 | 3,4-Dichloro-N-[4-(7-nitro-3,4-dihydro-1H-isoquinolin-2-yl)-butyl]-benzenesulfonamide | | 458 |
| 192 | 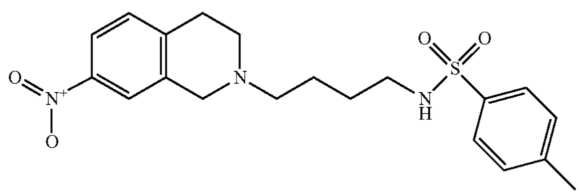 | 4-Methyl-N-[4-(7-nitro-3,4-dihydro-1H-isoquinolin-2-yl)-butyl]-benzenesulfonamide | | 404 |

| N° | STRUCTURE | Autonom | ¹H-NMR | MS (APCI) (M + H)⁺ |
|---|---|---|---|---|
| 193 | 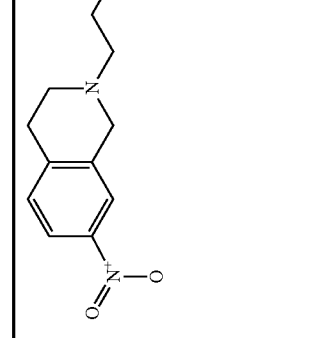 | 2-Naphthalen-1-yl-ethanesulfonic acid [4-(7-nitro-3,4-dihydro-1H-isoquinolin-2-yl)-butyl]-amide | | 468 |
| 194 | 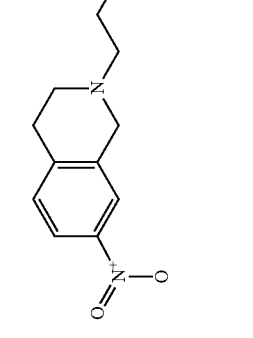 | Quinoline-8-sulfonic acid [4-(7-nitro-3,4-dihydro-1H-isoquinolin-2-yl)-butyl]-amide | | 441 |
| 195 | 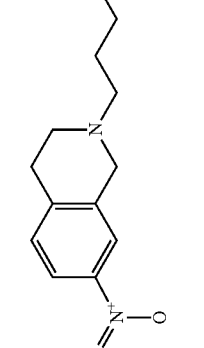 | 3-Nitro-N-[4-(7-nitro-3,4-dihydro-1H-isoquinolin-2-yl)-butyl]-benzenesulfonamide | | 435 |
| 196 | 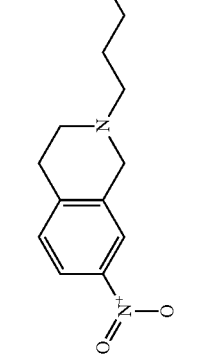 | 2-Methyl-5-nitro-N-[4-(7-nitro-3,4-dihydro-1H-isoquinolin-2-yl)-butyl]-benzenesulfonamide | | 449 |

| N° | STRUCTURE | Autonom | ¹H-NMR | MS (APCI) (M + H)⁺ |
|---|---|---|---|---|
| 197 | 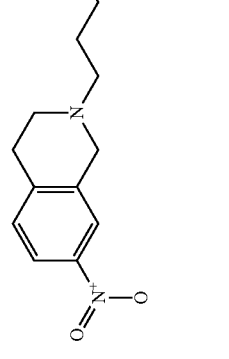 | 4-Bromo-2,5-difluoro-N-[4-(7-nitro-3,4-dihydro-1H-isoquinolin-2-yl)-butyl]-benzenesulfonamide | | 504 |
| 198 | 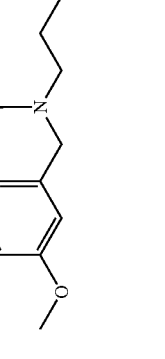 | N-[4-(6,7-Dimethoxy-3,4-dihydro-1H-isoquinolin-2-yl)-butyl]-4-methyl-benzenesulfonamide | | 419 |
| 199 | 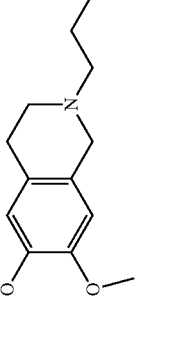 | 2-Naphthalen-1-yl-ethanesulfonic acid [4-(6,7-dimethoxy-3,4-dihydro-1H-isoquinolin-2-yl)-butyl]-amide | | 483 |
| 200 | 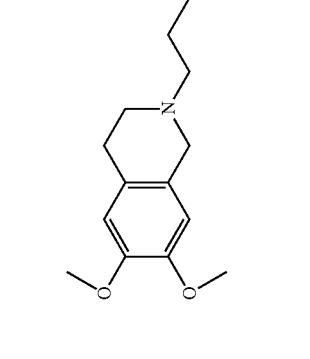 | Quinoline-8-sulfonic acid [4-(6,7-dimethoxy-3,4-dihydro-1H-isoquinolin-2-yl)-butyl]-amide | | 456 |

-continued

| N° | STRUCTURE | Autonom | ¹H-NMR | MS (APCI) (M + H)⁺ |
|---|---|---|---|---|
| 201 | 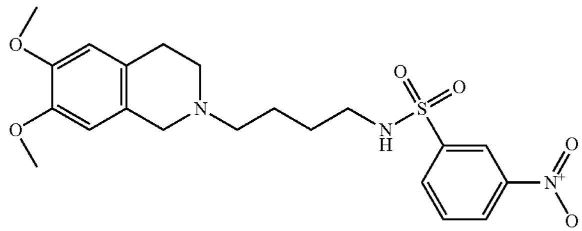 | N-[4-(6,7-Dimethoxy-3,4-dihydro-1H-isoquinolin-2-yl)-butyl]-3-nitro-benzenesulfonamide | | 450 |
| 202 | 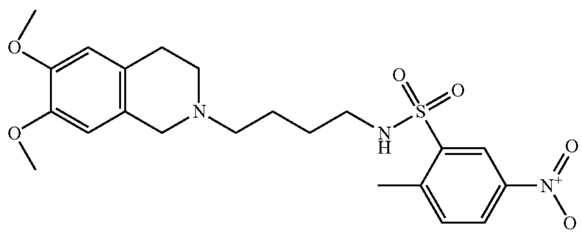 | N-[4-(6,7-Dimethoxy-3,4-dihydro-1H-isoquinolin-2-yl)-butyl]-2-methyl-5-nitro-benzenesulfonamide | | 464 |
| 203 | 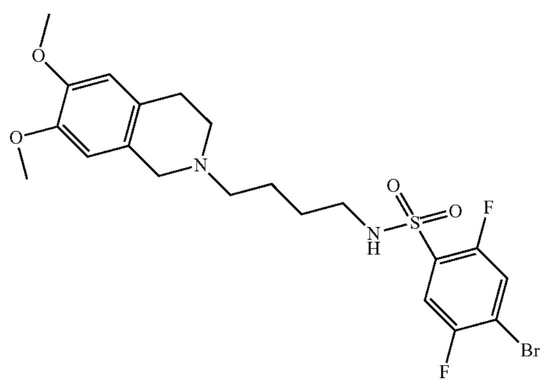 | 4-Bromo-N-[4-(6,7-dimethoxy-3,4-dihydro-1H-isoquinolin-2-yl)-butyl]-2,5-difluoro-benzenesulfonamide | | 519 |

-continued

| N° | STRUCTURE | Autonom | ¹H-NMR | MS (APCI) (M + H)⁺ |
|---|---|---|---|---|
| 204 | 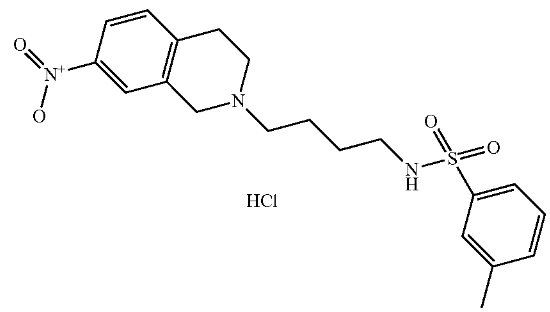 | 3-Methyl-N-[4-(7-nitro-3,4-dihydro-1H-isoquinolin-2-yl)-butyl]-benzenesulfonamide hydrochloride | | 404 |
| 205 | 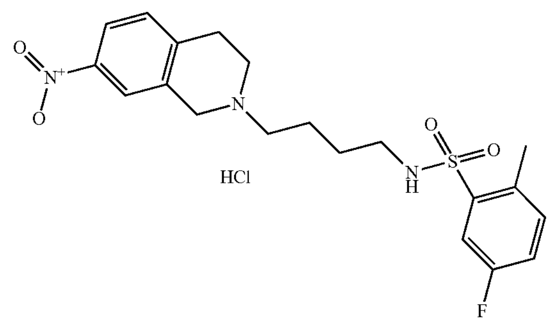 | 5-Fluoro-2-methyl-N-[4-(7-nitro-3,4-dihydro-1H-isoquinolin-2-yl)-butyl]-benzenesulfonamide hydrochloride | | 422 |
| 206 | 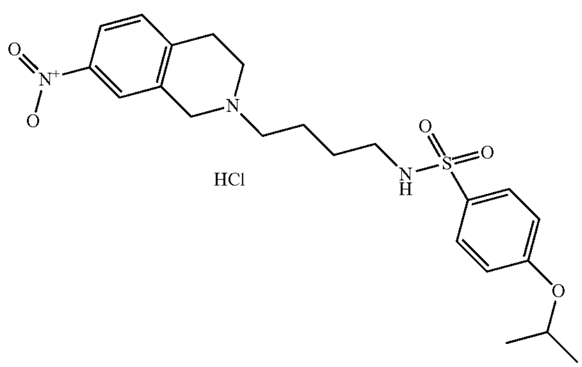 | 4-Isopropoxy-N-[4-(7-nitro-3,4-dihydro-1H-isoquinolin-2-yl)-butyl]-benzenesulfonamide hydrochloride | | 448 |

-continued
| N° | STRUCTURE | Autonom | ¹H-NMR | MS (APCI) (M + H)⁺ |
|---|---|---|---|---|
| 207 | 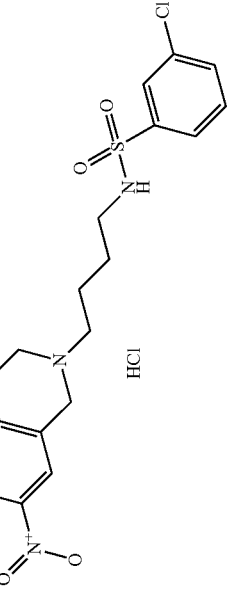 | 3-Chloro-N-[4-(7-nitro-3,4-dihydro-1H-isoquinolin-2-yl)-butyl]-benzenesulfonamide hydrochloride | | 424 |
| 208 | 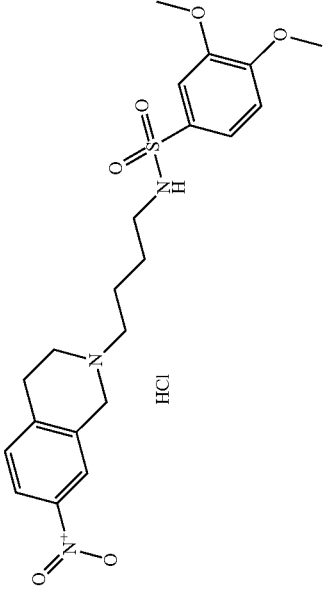 | 3,4-Dimethoxy-N-[4-(7-nitro-3,4-dihydro-1H-isoquinolin-2-yl)-butyl]-benzenesulfonamide hydrochloride | | 450 |
| 209 | 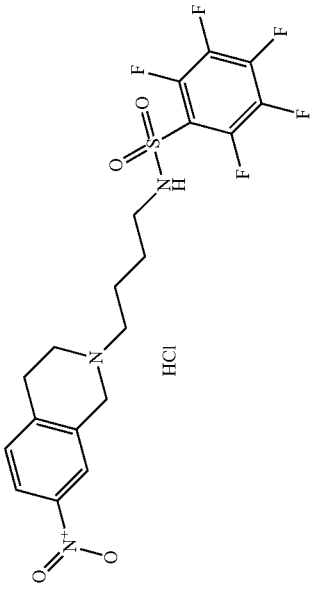 | 2,3,4,5,6-Pentafluoro-N-[4-(7-nitro-3,4-dihydro-1H-isoquinolin hydrochloride | | 480 |

| N° | STRUCTURE | Autonom | 1H-NMR | MS (APCI) (M + H)+ |
|---|---|---|---|---|
| 210 | (structure shown) HCl | N-[4-(6,7-Dimethoxy-3,4-dihydro-1H-isoquinolin-2-yl)-butyl]-3-methyl-benzenesulfonamide hydrochloride | 1H NMR (300 MHz, DMSO-D6) δ ppm 1.43 (m, 2H), 1.73 (m, 2H), 2.38 (s, 3H), 2.74 (q, J = 6.59 Hz, 2H), 2.87 (m, 1H), 3.07 (m, 3H), 3.17 (m, 1H), 3.58 (m, 1H), 3.70 (s, 3H), 3.72 (s, 3H), 4.11 (s, 1H), 4.35 (m, 1H), 6.77 (d, J = 9.66 Hz, 2H), 7.46 (m, 2H), 7.60 (m, 3H), 10.52 (s, 1H) | 419 |
| 211 | (structure shown) HCl | N-[4-(6,7-Dimethoxy-3,4-dihydro-1H-isoquinolin-2-yl)-butyl]-5-fluoro-2-methyl-benzenesulfonamide hydrochloride | 1H NMR (300 MHz, DMSO-D6) δ ppm 1.43 (m, 2H), 1.72 (m, 2H), 2.53 (s, 3H), 2.82 (q, J = 6.74 Hz, 2H), 2.91 (m, 1H), 3.10 (m, 3H), 3.25 (m, 1H), 3.58 (m, 1H), 3.70 (s, 3H), 3.72 (s, 3H), 4.07 (m, 1H), 4.33 (m, 1H), 6.75 (s, 1H), 6.79 (s, 1H), 7.42 (m, 2H), 7.56 (dd, J = 8.93, 2.78 Hz, 1H), 7.94 (t, J = 5.86 Hz, 1H), 10.47 (s, 1H) | 437 |

| N° | STRUCTURE | Autonom | ¹H-NMR | MS (APCI) (M + H)⁺ |
|---|---|---|---|---|
| 212 | 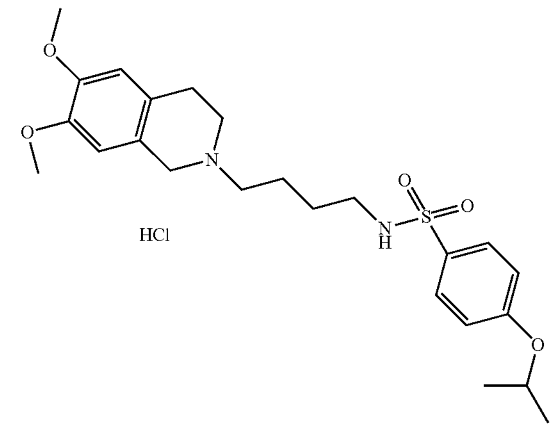 | N-[4-(6,7-Dimethoxy-3,4-dihydro-1H-isoquinolin-2-yl)-butyl]-4-isopropoxy-benzenesulfonamide hydrochloride | | 463 |
| 213 | 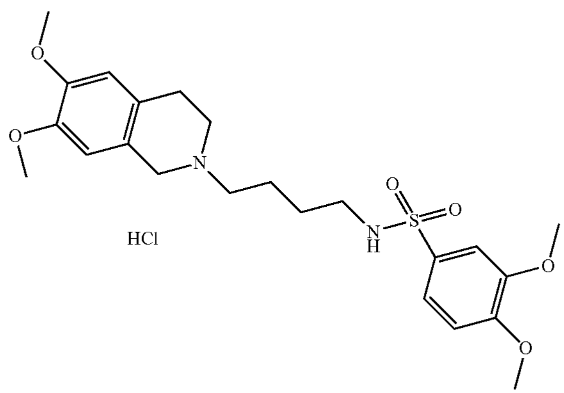 | N-[4-(6,7-Dimethoxy-3,4-dihydro-1H-isoquinolin-2-yl)-butyl]-3,4-dimethoxy-benzenesulfonamide hydrochloride | | 465 |

| N° | STRUCTURE | Autonom | ¹H-NMR | MS (APCI) (M + H)⁺ |
|---|---|---|---|---|
| 214 | 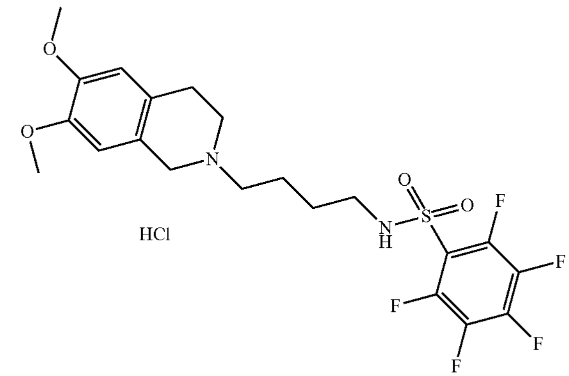 | N-[4-(6,7-Dimethoxy-3,4-dihydro-1H-isoquinolin-2-yl)-butyl]-2,3,4,5,6-pentafluoro-benzenesulfonamide hydrochloride | | 495 |
| 215 | 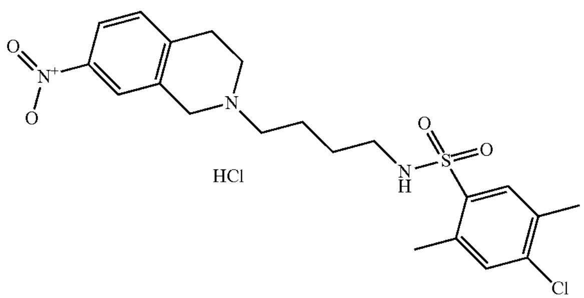 | 4-Chloro-2,5-dimethyl-N-[4-(7-nitro-3,4-dihydro-1H-isoquinolin-2-yl)-butyl]-benzenesulfonamide hydrochloride | | 452 |
| 216 | 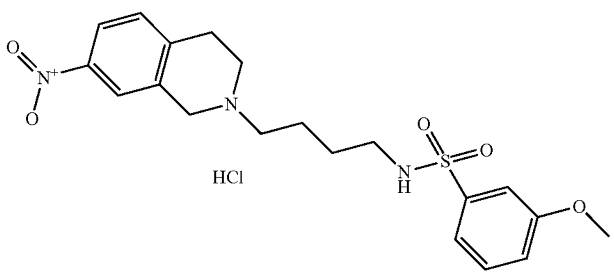 | 3-Methoxy-N-[4-(7-nitro-3,4-dihydro-1H-isoquinolin-2-yl)-butyl]-benzenesulfonamide hydrochloride | | 420 |

| N° | STRUCTURE | Autonom | ¹H-NMR | MS (APCI) (M+H)⁺ |
|---|---|---|---|---|
| 217 | 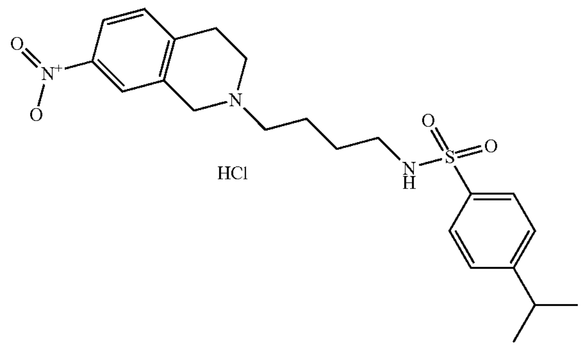 | 4-Isopropyl-N-[4-(7-nitro-3,4-dihydro-1H-isoquinolin-2-yl)-butyl]-benzenesulfonamide hydrochloride | | 432 |
| 218 | 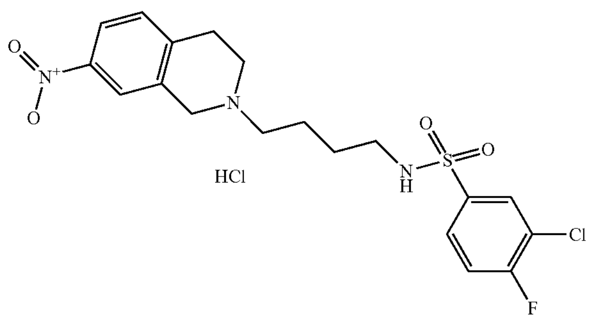 | 3-Chloro-4-fluoro-N-[4-(7-nitro-3,4-dihydro-1H-isoquinolin-2-yl)-butyl]-benzenesulfonamide hydrochloride | | 442 |
| 219 | 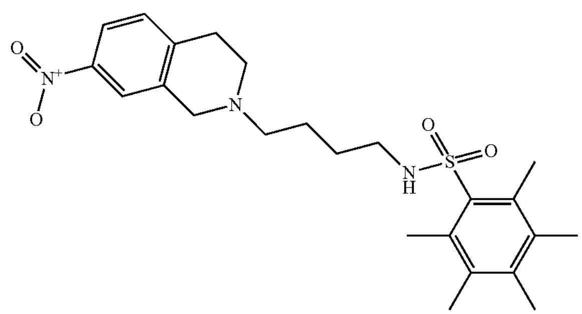 | 2,3,4,5,6-Pentamethyl-N-[4-(7-nitro-3,4-dihydro-1H-isoquinolin-2-yl)-butyl]-benzenesulfonamide | | 460 |

| N° | STRUCTURE | Autonom | 1H-NMR | MS (APCI) (M + H)+ |
|---|---|---|---|---|
| 220 | (structure shown) · HCl | 4-Chloro-N-[4-(6,7-dimethoxy-3,4-dihydro-1H-isoquinolin-2-yl)-butyl]-2,5-dimethyl-benzenesulfonamide hydrochloride | 1H NMR (300 MHz, DMSO-D6) δ ppm 1.43 (m, 2H), 1.71 (m, 2H), 2.34 (s, 3H), 2.77 (q, J = 6.78 Hz, 2H), 2.91 (m, 1H), 3.09 (m, 3H), 3.24 (m, 1H), 3.55 (m, 1H), 3.70 (s, 3H), 3.72 (s, 3H), 4.09 (m, 1H), 4.33 (m, 1H), 6.75 (s, 1H), 6.79 (s, 1H), 7.50 (s, 1H), 7.75 (s, 1H), 7.81 (t, J = 5.78 Hz, 1H), 10.51 (s, 1H) | 467 |
| 221 | (structure shown) · HCl | N-[4-(6,7-Dimethoxy-3,4-dihydro-1H-isoquinolin-2-yl)-butyl]-3-methoxy-benzenesulfonamide hydrochloride | 1H NMR (300 MHz, DMSO-D6) δ ppm 1.44 (m, 2H), 1.75 (m, 2H), 2.76 (q, J = 6.59 Hz, 2H), 2.90 (m, 1H), 3.09 (m, 2H), 3.18 (m, 2H), 3.61 (m, 1H), 3.71 (s, 3H), 3.72 (s, 3H), 3.82 (s, 3H), 4.08 (m, 1H), 4.34 (d, J = 14.64 Hz, 1H), 6.76 (s, 1H), 6.80 (s, 1H), 7.21 (d, J = 8.20 Hz, 1H), 7.29 (m, 1H), 7.35 (d, J = 7.91 Hz 1H), 7.52 (t, J = 7.91 Hz, 1H), 7.71 (s, 1H), 10.25 (s, 1H) | 435 |
| 222 | (structure shown) · HCl | N-[4-(6,7-Dimethoxy-3,4-dihydro-1H-isoquinolin-2-yl)-butyl]-4-isopropyl-benzenesulfonamide hydrochloride | | 447 |

| N° | STRUCTURE | Autonom | ¹H-NMR | MS (APCI) (M+H⁺) |
|---|---|---|---|---|
| 223 | 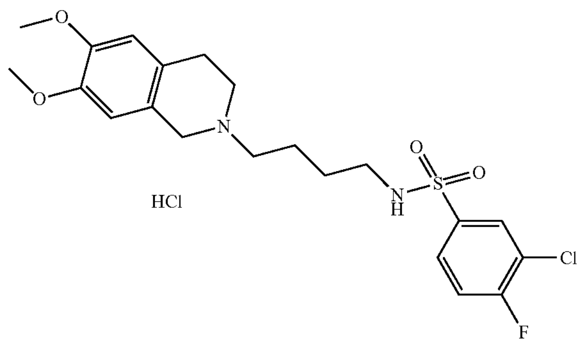 | 3-Chloro-N-[4-(6,7-dimethoxy-3,4-dihydro-1H-isoquinolin-2-yl)-butyl]-4-fluoro-benzenesulfonamide hydrochloride | 1H NMR (300 MHz, DMSO-D6) δ ppm 1.44 (m, 2H), 1.75 (m, 2H), 2.79 (q, J = 6.59 Hz, 2H), 2.89 (m, 1H), 3.09 (m, 3H), 3.23 (m, 1H), 3.58 (m, 1H), 3.70 (s, 3H), 3.72 (s, 3H), 4.09 (m, 1H), 4.34 (d, J = 14.20 Hz, 1H), 6.76 (s, 1H), 6.79 (s, 1H), 7.67 (t, J = 8.93 Hz, 1H), 7.82 (m, 1H), 7.92 (s, 1H), 7.98 (dd, J = 6.88, 2.20 Hz, 1H), 10.51 (s, 1H) | 457 |
| 224 | 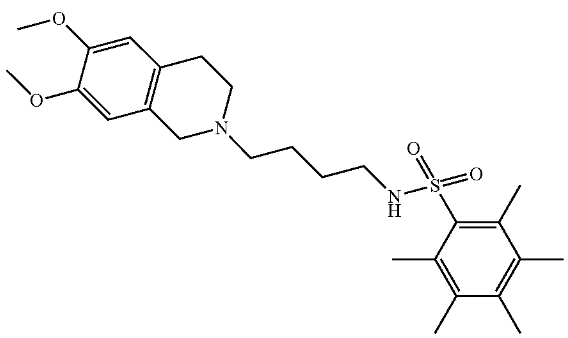 | N-[4-(6,7-Dimethoxy-3,4-dihydro-1H-isoquinolin-2-yl)-butyl]-2,3,4,5,6-pentamethyl-benzenesulfonamide | | 475 |
| 225 | 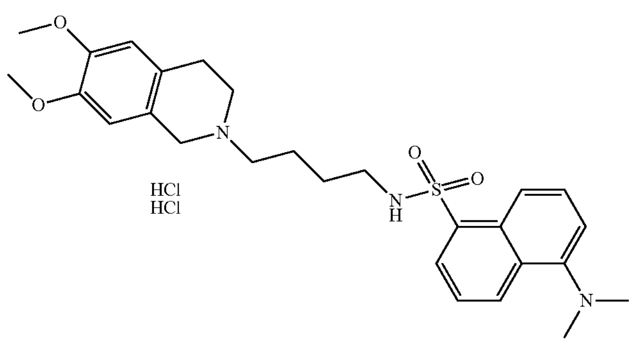 | 5-Dimethylamino-naphthalene-1-sulfonic acid [4-(6,7-dimethoxy-3,4-dihydro-1H-isoquinolin-2-yl)-butyl]-amide dihydrochloride | | 498 |

| N° | STRUCTURE | Autonom | ¹H-NMR | MS (APCI) (M + H)⁺ |
|---|---|---|---|---|
| 226 | 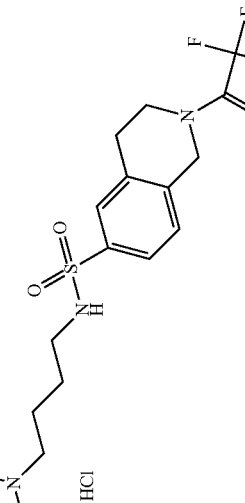 | 2-(2,2,2-Trifluoro-acetyl)-1,2,3,4-tetrahydro-isoquinoline-6-sulfonic acid [4-(7-nitro-3,4-dihydro-1H-isoquinolin-2-yl)-butyl]-amide hydrochloride | | 541 |
| 227 | 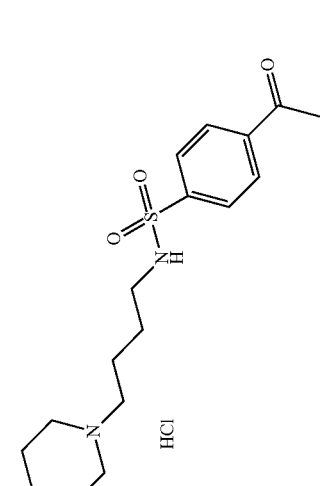 | 4-Acetyl-N-[4-(7-nitro-3,4-dihydro-1H-isoquinolin-2-yl)-butyl]-benzenesulfonamide hydrochloride | | 432 |
| 228 | 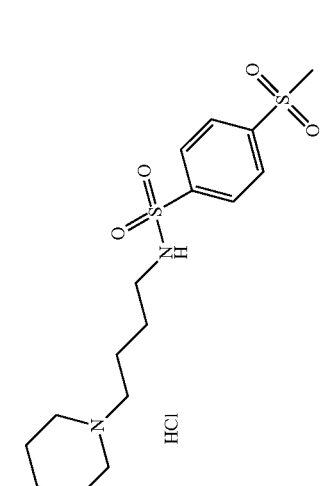 | 4-Methanesulfonyl-N-[4-(7-nitro-3,4-dihydro-1H-isoquinolin-2-yl)-butyl]-benzenesulfonamide hydrochloride | | 468 |

| N° | STRUCTURE | Autonom | ¹H-NMR | MS (APCI) (M + H)⁺ |
|---|---|---|---|---|
| 229 | 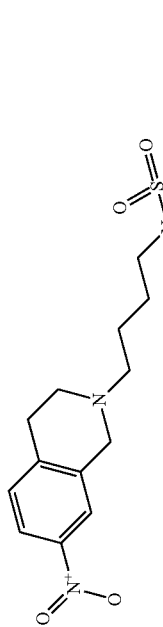 | Biphenyl-4-sulfonic acid [4-(7-nitro-3,4-dihydro-1H-isoquinolin-2-yl)-butyl]-amide hydrochloride | | 466 |
| 230 | 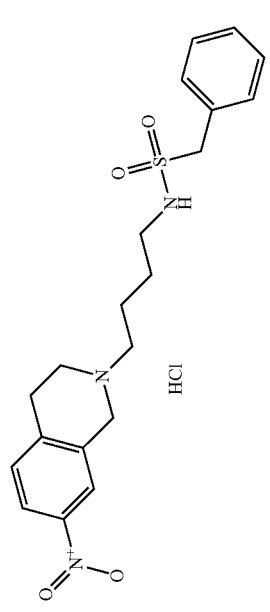 | N-[4-(7-Nitro-3,4-dihydro-1H-isoquinolin-2-yl)-butyl]-C-phenyl-methanesulfonamide hydrochloride | | 404 |
| 231 | 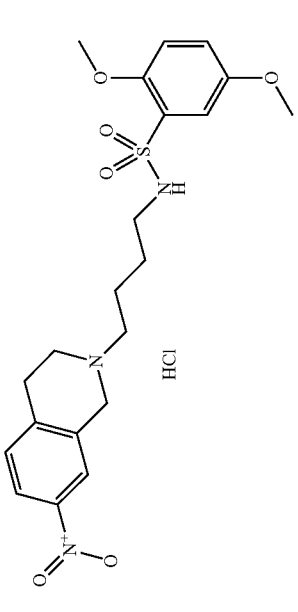 | 2,5-Dimethoxy-N-[4-(7-nitro-3,4-dihydro-1H-isoquinolin-2-yl)-butyl]-benzenesulfonamide hydrochloride | | 450 |

| N° | STRUCTURE | Autonom | ¹H-NMR | MS (APCI) (M + H)⁺ |
|---|---|---|---|---|
| 232 | 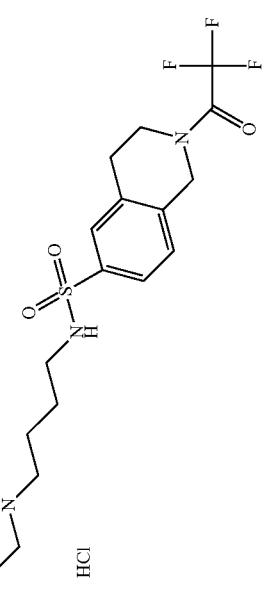 HCl | 2-(2,2,2-Trifluoro-acetyl)-1,2,3,4-tetrahydro-isoquinoline-6-sulfonic acid [4-(6,7-dimethoxy-3,4-dihydro-1H-isoquinolin-2-yl)-butyl]-amide hydrochloride | | 556 |
| 233 | 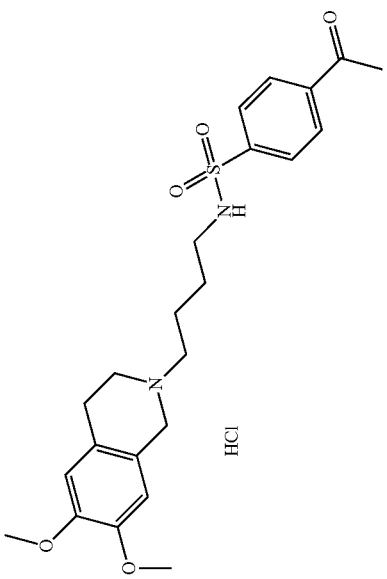 HCl | 4-Acetyl-N-[4-(6,7-dimethoxy-3,4-dihydro-1H-isoquinolin-2-yl)-butyl]-benzenesulfonamide hydrochloride | | 447 |

| N° | STRUCTURE | Autonom | ¹H-NMR | MS (APCI) (M + H)⁺ |
|---|---|---|---|---|
| 234 | 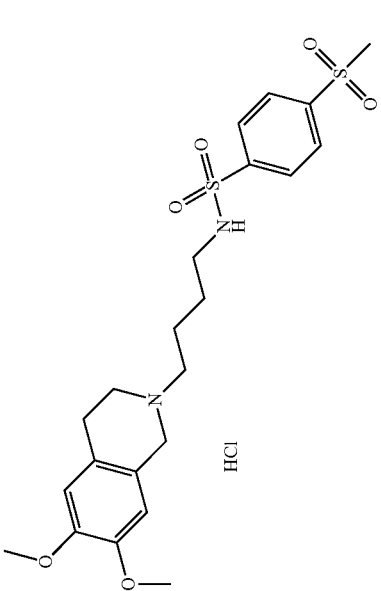 HCl | N-[4-(6,7-Dimethoxy-3,4-dihydro-1H-isoquinolin-2-yl)-butyl]-4-methanesulfonyl-benzenesulfonamide hydrochloride | | 483 |
| 235 | 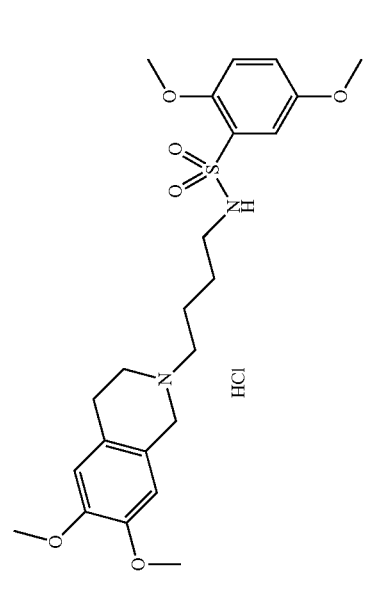 HCl | N-[4-(6,7-Dimethoxy-3,4-dihydro-1H-isoquinolin-2-yl)-butyl]-2,5-dimethoxy-benzenesulfonamide hydrochloride | 1H NMR (300 MHz, DMSO-D6) δ ppm 1.42 (m, 2H), 1.72 (m, 2H), 2.78 (q, J = 6.44 Hz, 2H), 2.91 (m, 1H), 3.09 (m, 3H), 3.25 (m, 1H), 3.55 (m, 1H), 3.70 (s, 3H), 3.71 (s, 3H), 3.73 (s, 3H), 3.83 (s, 3H), 4.10 (m, 1H), 4.34 (m, 1H), 6.75 (s, 1H), 6.79 (s, 1H), 7.17 (m, 2H), 7.22 (m, 1H), 7.32 (m, 1H), 10.29 (s, 1H) | 465 |
| 236 | 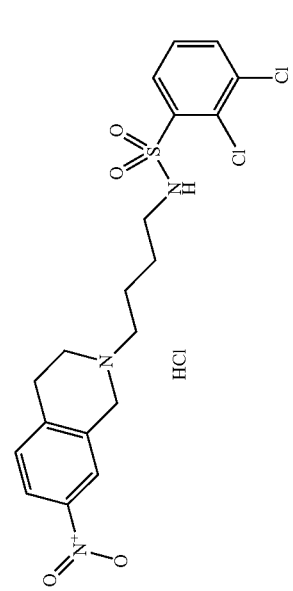 HCl | 2,3-Dichloro-N-[4-(7-nitro-3,4-dihydro-1H-isoquinolin-2-yl)-butyl]-benzenesulfonamide hydrochloride | | 458 |

-continued

| N° | STRUCTURE | Autonom | ¹H-NMR | MS (APCI) (M + H)⁺ |
|---|---|---|---|---|
| 237 | 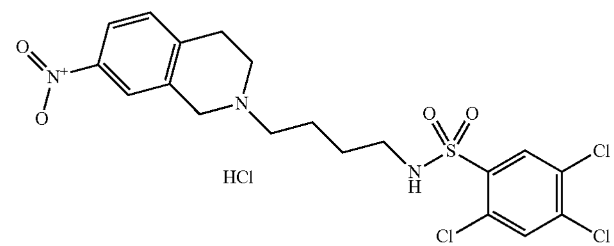 | 2,4,5-Trichloro-N-[4-(7-nitro-3,4-dihydro-1H-isoquinolin-2-yl)-butyl]-benzenesulfonamide hydrochloride | | 492 |
| 238 | 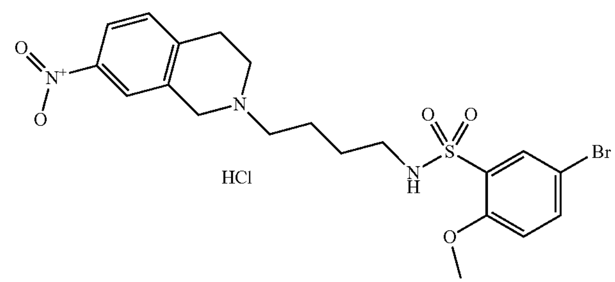 | 5-Bromo-2-methoxy-N-[4-(7-nitro-3,4-dihydro-1H-isoquinolin-2-yl)-butyl]-benzenesulfonamide hydrochloride | | 498 |
| 239 | 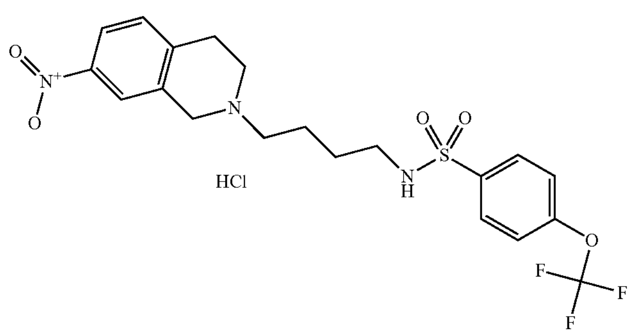 | N-[4-(7-Nitro-3,4-dihydro-1H-isoquinolin-2-yl)-butyl]-4-trifluoromethoxy-benzenesulfonamide hydrochloride | | 474 |

| N° | STRUCTURE | Autonom | ¹H-NMR | MS (APCI) (M + H)⁺ |
|---|---|---|---|---|
| 240 | 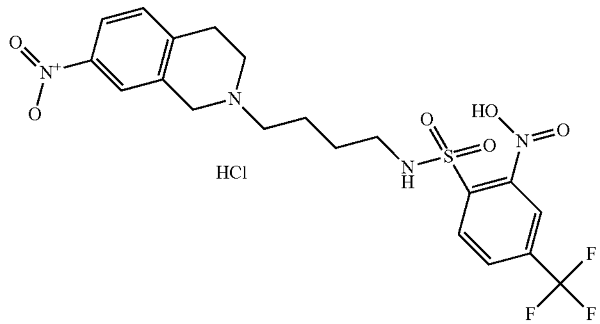 | 2-Nitro-N-[4-(7-nitro-3,4-dihydro-1H-isoquinolin-2-yl)-butyl]-4-trifluoromethyl-benzenesulfonamide hydrochloride | | 503 |
| 241 | 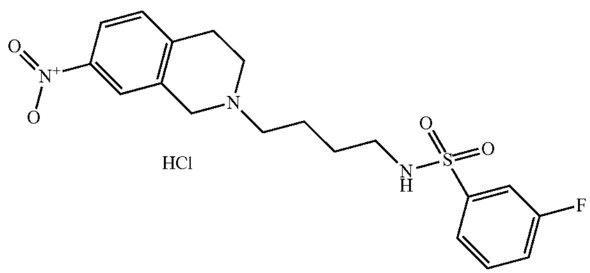 | 3-Fluoro-N-(4-(7-nitro-3,4-dihydro-1H-isoquinolin-2-yl)-butyl]-benzenesulfonamide hydrochloride | | 408 |
| 242 | 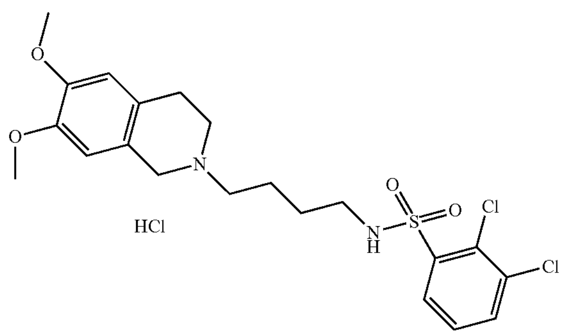 | 2,3-Dichloro-N-[4-(6,7-dimethoxy-3,4-dihydro-1H-isoquinolin-2-yl)-butyl]-benzenesulfonamide hydrochloride | 1H NMR (300 MHz, DMSO-D6) δ ppm 1.45 (m, 2H), 1.72 (m, 2H), 2.87 (m, 3H), 3.09 (m, 3H), 3.22 (m, 1H), 3.57 (m, 1H), 3.70 (s, 3H), 3.71 (s, 3H), 4.07 (m, 1H), 4.33 (m, 1H), 6.75 (s, 1H), 6.79 (s, 1H), 7.56 (t, J = 7.98 Hz, 1H), 7.94 (ddd, J = 5.42, 1.54 Hz, 2H), 8.18 (t, J = 5.64 Hz, 1H), 10.29 (s, 1H) | 473 |

| N° | STRUCTURE | Autonom | ¹H-NMR | MS (APCI) (M+H)⁺ |
|---|---|---|---|---|
| 243 | 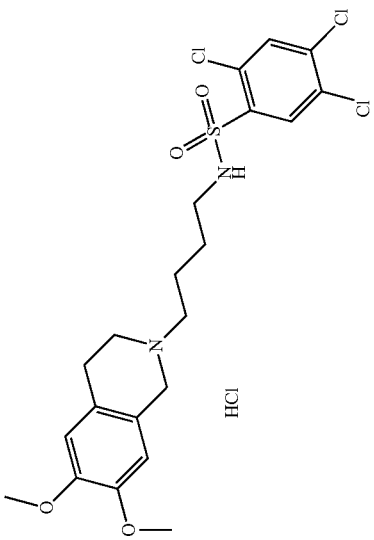 | 2,4,5-Trichloro-N-[4-(6,7-dimethoxy-3,4-dihydro-1H-isoquinolin-2-yl)-butyl]-benzenesulfonamide hydrochloride | 1H NMR (300 MHz, DMSO-D6) δ ppm 1.45 (m, 2H), 1.69 (m, 2H), 2.89 (m, 3H), 3.10 (m, 3H), 3.24 (m, 1H), 3.58 (m, 1H), 3.70 (s, 3H), 3.71 (s, 3H), 4.10 (m, 1H), 4.34 (m, 1H), 6.75 (s, 1H), 6.79 (s, 1H), 8.06 (s, 1H), 8.13 (s, 1H), 8.26 (t, J = 5.64 Hz, 1H), 10.18 (s, 1H) | 507 |
| 244 | 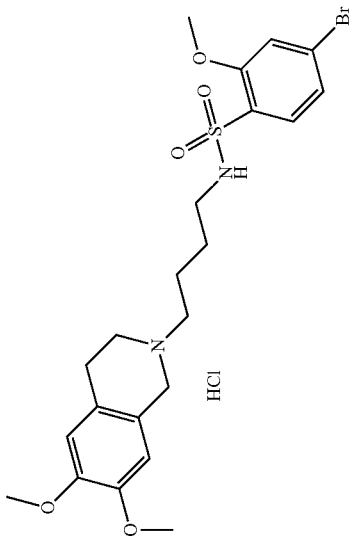 | 4-Bromo-N-[4-(6,7-dimethoxy-3,4-dihydro-1H-isoquinolin-2-yl)-butyl]-2-methoxy-benzenesulfonamide hydrochloride | | 513 |

| N° | STRUCTURE | Autonom | ¹H-NMR | MS (APCI) (M + H)⁺ |
|---|---|---|---|---|
| 245 | 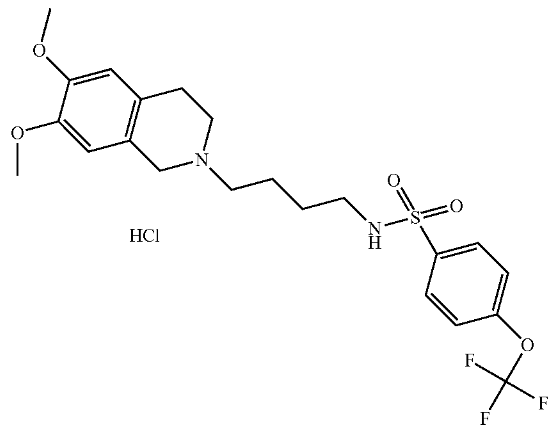 | N-[4-(6,7-Dimethoxy-3,4-dihydro-1H-isoquinolin-2-yl)-butyl]-4-trifluoromethoxy-benzenesulfonamide hydrochloride | | 489 |
| 246 | 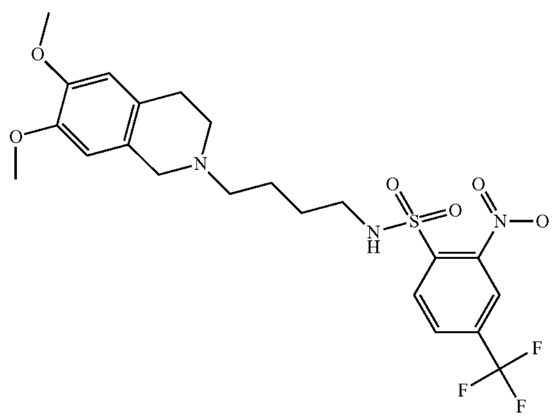 | N-[4-(6,7-Dimethoxy-3,4-dihydro-1H-isoquinolin-2-yl)-butyl]-2-nitro-4-trifluoromethyl-benzenesulfonamide | | 518 |

| N° | STRUCTURE | Autonom | ¹H-NMR | MS (APCI) (M + H)⁺ |
|---|---|---|---|---|
| 247 | 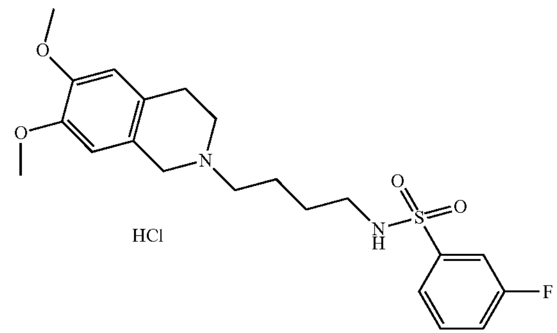 | N-[4-(6,7-Dimethoxy-3,4-dihydro-1H-isoquinolin-2-yl)-butyl]-3-fluoro-benzenesulfonamide hydrochloride | | 423 |
| 248 | 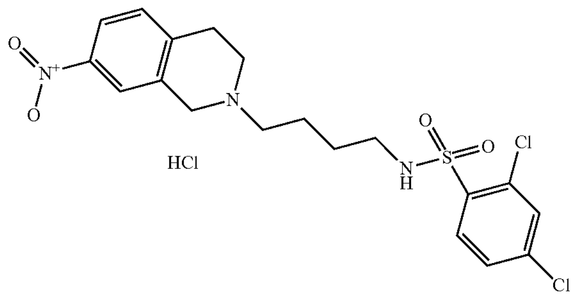 | 2,4-Dichloro-N-[4-(7-nitro-3,4-dihydro-1H-isoquinolin-2-yl)-butyl]-benzenesulfonamide hydrochloride | | 458 |
| 249 | 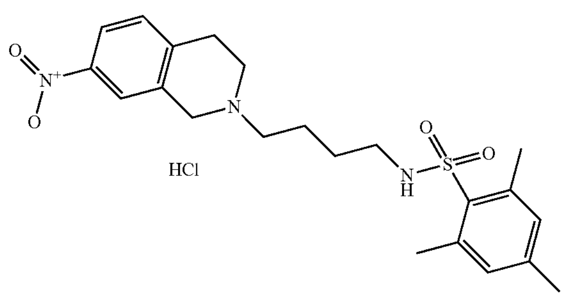 | 2,4,6-Trimethyl-N-[4-(7-nitro-3,4-dihydro-1H-isoquinolin-2-yl)-butyl]-benzenesulfonamide hydrochloride | | 432 |

-continued

| N° | STRUCTURE | Autonom | ¹H-NMR | MS (APCI) (M + H)⁺ |
|---|---|---|---|---|
| 250 | 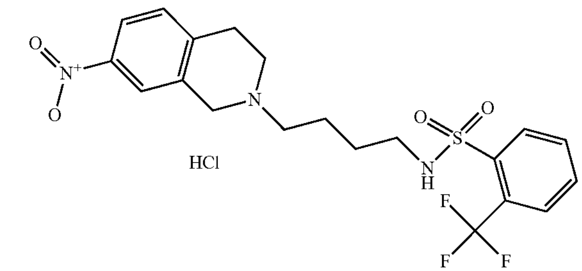 | N-[4-(7-Nitro-3,4-dihydro-1H-isoquinolin-2-yl)-butyl]-2-trifluoromethyl-benzenesulfonamide hydrochloride | | 458 |
| 251 | 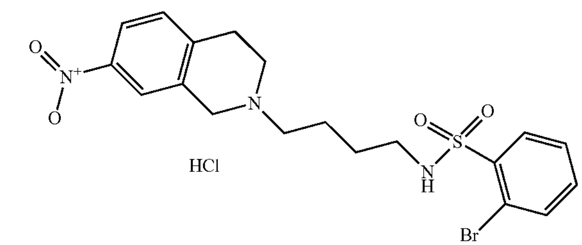 | 2-Bromo-N-[4-(7-nitro-3,4-dihydro-1H-isoquinolin-2-yl)-butyl]-benzenesulfonamide hydrochloride | | 468 |
| 252 | 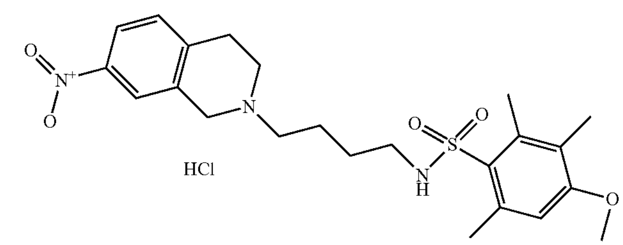 | 4-Methoxy-2,3,6-trimethyl-N-[4-(7-nitro-3,4-dihydro-1H-isoquinolin-2-yl)-butyl]-benzenesulfonamide hydrochloride | | 462 |
| 253 | 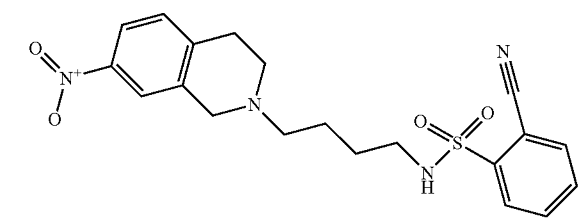 | 2-Cyano-N-[4-(7-nitro-3,4-dihydro-1H-isoquinolin-2-yl)-butyl]-benzenesulfonamide | | 415 |

-continued

| N° | STRUCTURE | Autonom | ¹H-NMR | MS (APCI) (M + H)⁺ |
|---|---|---|---|---|
| 254 | 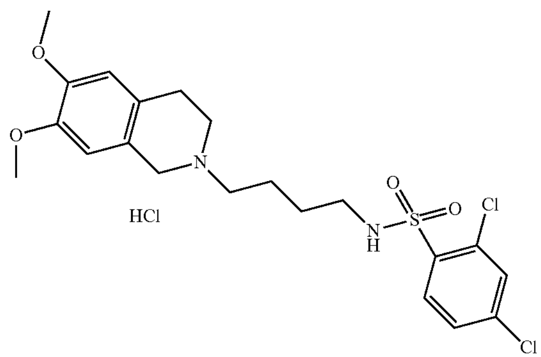 | 2,4-Dichloro-N-[4-(6,7-dimethoxy-3,4-dihydro-1H-isoquinolin-2-yl)-butyl]-benzenesulfonamide hydrochloride | | 473 |
| 255 | 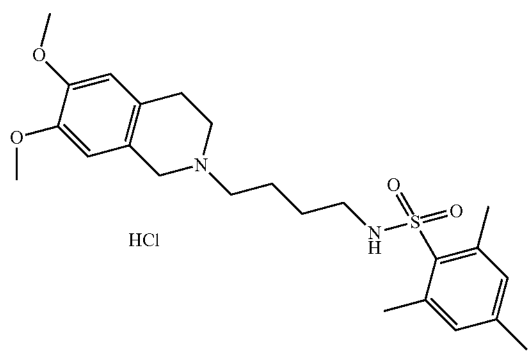 | N-[4-(6,7-Dimethoxy-3,4-dihydro-1H-isoquinolin-2-yl)-butyl]-2,4,6-trimethyl-benzenesulfonamide hydrochloride | | 447 |

| N° | STRUCTURE | Autonom | ¹H-NMR | MS (APCI) (M + H)⁺ |
|---|---|---|---|---|
| 256 |  HCl | N-[4-(6,7-Dimethoxy-3,4-dihydro-1H-isoquinolin-2-yl)-butyl]-2-trifluoromethyl-benzenesulfonamide hydrochloride | | 473 |
| 257 |  HCl | 2-Bromo-N-[4-(6,7-dimethoxy-3,4-dihydro-1H-isoquinolin-2-yl)-butyl]-benzenesulfonamide hydrochloride | | 483 |

-continued
| N° | STRUCTURE | Autonom | ¹H-NMR | MS (APCI) (M + H)⁺ |
|---|---|---|---|---|
| 258 | 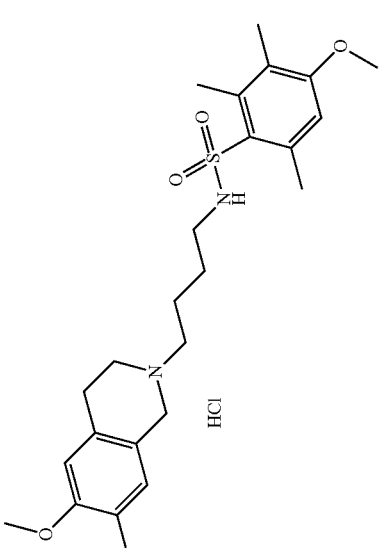 | N-[4-(6,7-Dimethoxy-3,4-dihydro-1H-isoquinolin-2-yl)-butyl]-4-methoxy-2,3,6-trimethyl-benzenesulfonamide hydrochloride | | 477 |
| 259 | 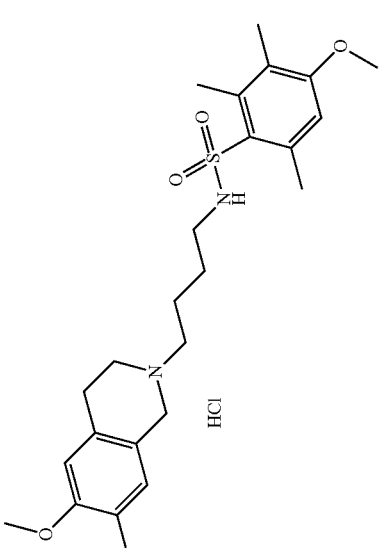 | 2-Cyano-N-[4-(6,7-dimethoxy-3,4-dihydro-1H-isoquinolin-2-yl)-butyl]-benzenesulfonamide hydrochloride | | 430 |

| N° | STRUCTURE | Autonom | ¹H-NMR | MS (APCI) (M + H)⁺ |
|---|---|---|---|---|
| 260 | 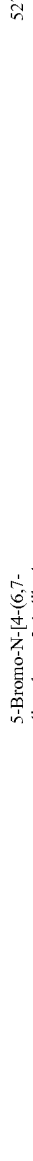 | 5-Bromo-N-[4-(6,7-dimethoxy-3,4-dihydro-1H-isoquinolin-2-yl)-butyl]-2-methoxy-benzenesulfonamide oxalate | | 527 |
| 261 | 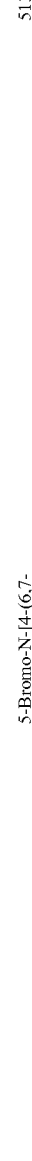 | 5-Bromo-N-[4-(6,7-dimethoxy-3,4-dihydro-1H-isoquinolin-2-yl)-butyl]-2-methoxy-benzenesulfonamide oxalate | | 513 |
| 262 | 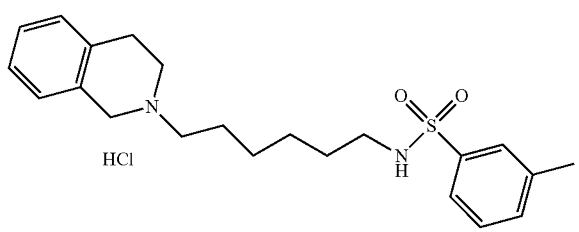 | N-[6-(3,4-Dihydro-1H-isoquinolin-2-yl)-hexyl]-3-methyl-benzenesulfonamide hydrochloride | | 387 |

| N° | STRUCTURE | Autonom | ¹H-NMR | MS (APCI) (M + H)⁺ |
|---|---|---|---|---|
| 263 | 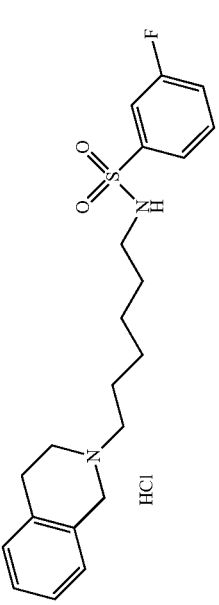 | N-[6-(3,4-Dihydro-1H-isoquinolin-2-yl)-hexyl]-3-fluoro-benzenesulfonamide hydrochloride | | 391 |
| 264 | 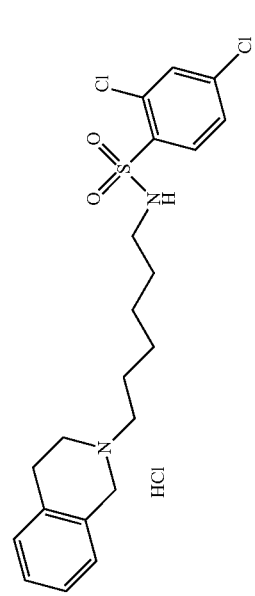 | 2,4-Dichloro-N-[6-(3,4-dihydro-1H-isoquinolin-2-yl)-hexyl]-benzenesulfonamide hydrochloride | | 441 |
| 265 | 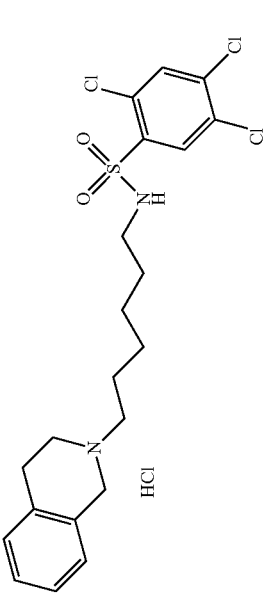 | 2,4,5-Trichloro-N-[6-(3,4-dihydro-1H-isoquinolin-2-yl)-hexyl]-benzenesulfonamide hydrochloride | | 475 |
| 266 | 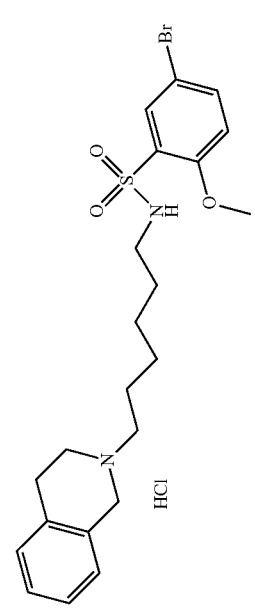 | 5-Bromo-N-[6-(3,4-dihydro-1H-isoquinolin-2-yl)-hexyl]-2-methoxy-benzenesulfonamide hydrochloride | | 481 |

-continued

| N° | STRUCTURE | Autonom | ¹H-NMR | MS (APCI) (M + H)⁺ |
|---|---|---|---|---|
| 267 | 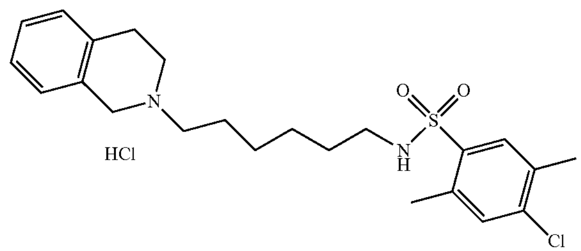 | 4-Chloro-N-[6-(3,4-dihydro-1H-isoquinolin-2-yl)-hexyl]-2,5-dimethyl-benzenesulfonamide hydrochloride | | 435 |
| 268 | 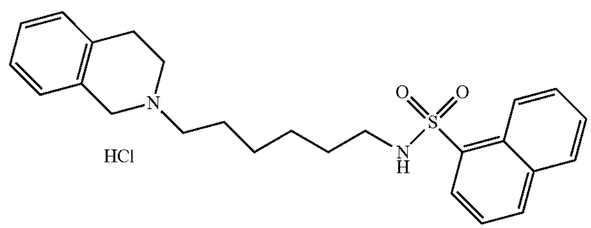 | Naphthalene-1-sulfonic acid [6-(3,4-dihydro-1H-isoquinolin-2-yl)-hexyl]-amide hydrochloride | | 423 |
| 269 | 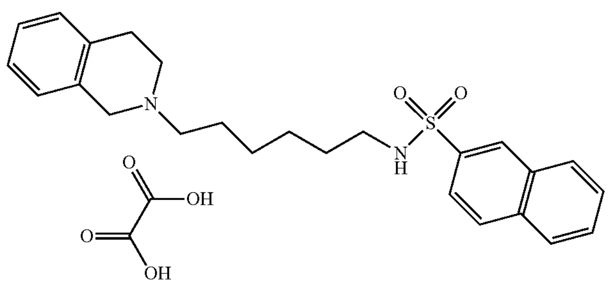 | Naphthalene-2-sulfonic acid [6-(3,4-dihydro-1H-isoquinolin-2-yl)-hexyl]-amide oxalate | | 423 |

-continued

| N° | STRUCTURE | Autonom | ¹H-NMR | MS (APCI) (M + H)⁺ |
|---|---|---|---|---|
| 270 | 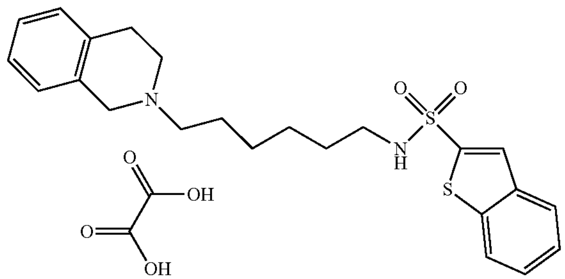 | Benzo[b]thiophene-2-sulfonic acid [6-(3,4-dihydro-1H-isoquinolin-2-yl)-hexyl]-amide oxalate | | 429 |
| 271 | 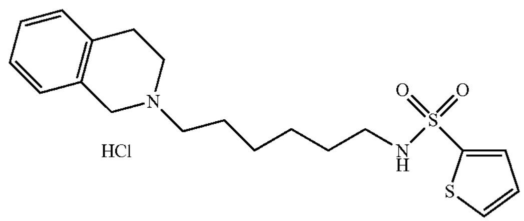 | Thiophene-2-sulfonic acid [6-(3,4-dihydro-1H-isoquinolin-2-yl)-hexyl]-amide hydrochloride | | 379 |
| 272 | 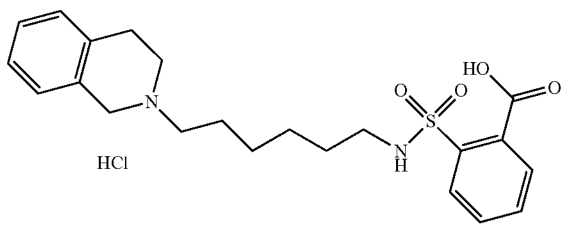 | N-[6-(3,4-Dihydro-1H-isoquinolin-2-yl)-hexyl]-2-nitro-benzenesulfonamide hydrochloride | | 418 |
| 273 | 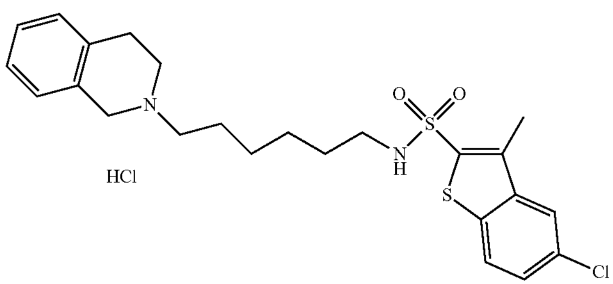 | 5-Chloro-3-methyl-benzo[b]thiophene-2-sulfonic acid [6-(3,4-dihydro-1H-isoquinolin-2-yl)-hexyl]-amide hydrochloride | | 477 |

-continued

| N° | STRUCTURE | Autonom | ¹H-NMR | MS (APCI) (M + H)⁺ |
|---|---|---|---|---|
| 274 | 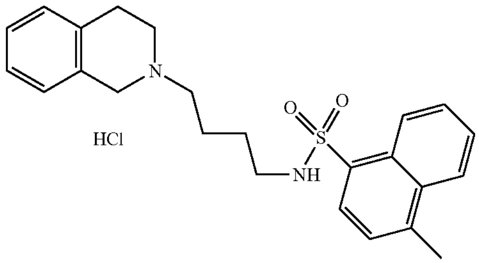 | 4-Methyl-naphthalene-1-sulfonic acid [4-(3,4-dihydro-1H-isoquinolin-2-yl)-butyl]-amide hydrochloride | | 409 |
| 275 | 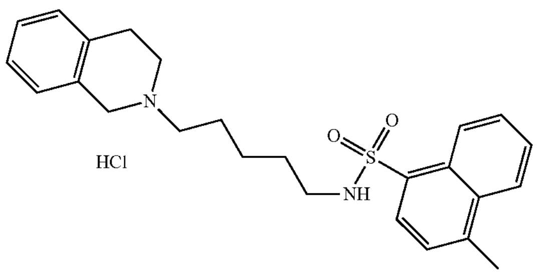 | 4-Methyl-naphthalene-1-sulfonic acid [5-(3,4-dihydro-1H-isoquinolin-2-yl)-pentyl]-amide hydrochloride | | 423 |
| 276 | 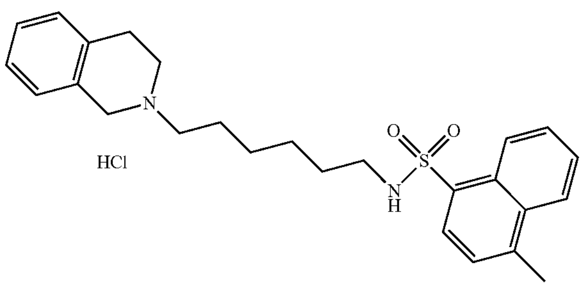 | 4-Methyl-naphthalene-1-sulfonic acid [6-(3,4-dihydro-1H-isoquinolin-2-yl)-hexyl]-amide hydrochloride | | 437 |

-continued

| N° | STRUCTURE | Autonom | ¹H-NMR | MS (APCI) (M + H)⁺ |
|---|---|---|---|---|
| 277 | 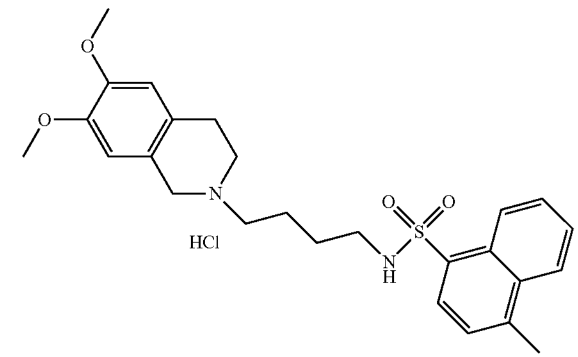 | 4-Methyl-naphthalene-1-sulfonic acid [4-(6,7-dimethoxy-3,4-dihydro-1H-isoquinolin-2-yl)-butyl]-amide hydrochloride | | 469 |
| 278 | 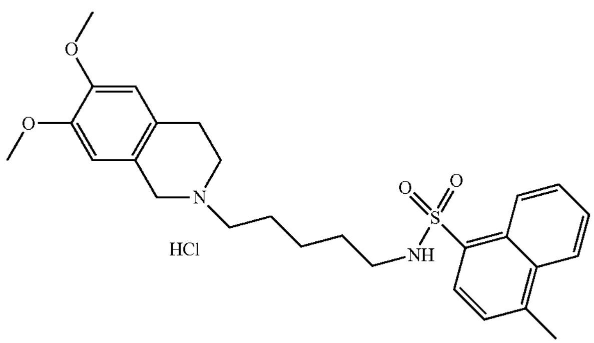 | 4-Methyl-naphthalene-1-sulfonic acid [5-(6,7-dimethoxy-3,4-dihydro-1H-isoquinolin-2-yl)-pentyl]-amide hydrochloride | | 483 |
| 279 | 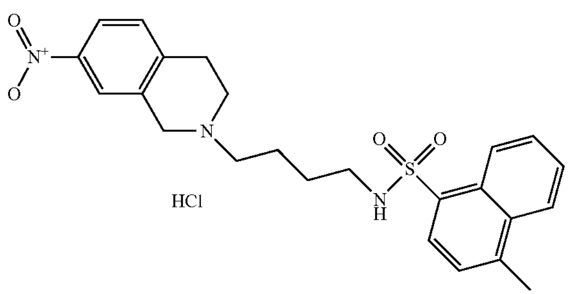 | 4-Methyl-naphthalene-1-sulfonic acid [4-(7-nitro-3,4-dihydro-1H-isoquinolin-2-yl)-butyl]-amide hydrochloride | | 454 |

| N° | STRUCTURE | Autonom | 1H-NMR | MS (APCI) (M + H)+ |
|---|---|---|---|---|
| 280 | 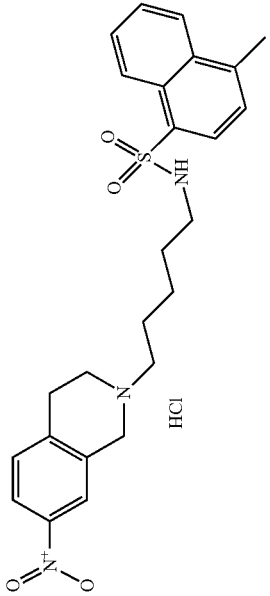 | 4-Methyl-naphthalene-1-sulfonic acid [5-(7-nitro-3,4-dihydro-1H-isoquinolin-2-yl)-pentyl]-amide hydrochloride | | 468 |
| 281 | 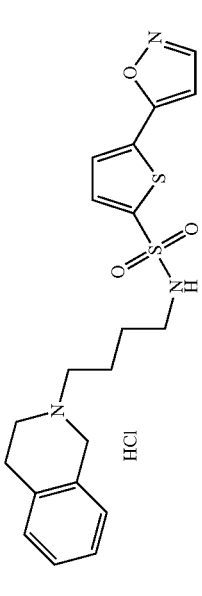 | 5-Isoxazol-5-yl-thiophene-2-sulfonic acid [4-(3,4-dihydro-1H-isoquinolin-2-yl)-butyl]-amide hydrochloride | 1H NMR (300 MHz, DMSO-D6) δ ppm 1.50 (m, 2H), 1.78 (m, 2H), 2.92 (q, J = 6.74 Hz, 2H), 3.01 (m, 1H), 3.13 (m, 3H), 3.22 (m, 1H), 3.64 (m, 1H), 4.22 (dd J = 15.45, 8.13 Hz, 1H), 4.46 (m,1H), 7.10 (s, 1H), 7.22 (m, 4H), 7.69 (d, J = 3.95 Hz, 1H), 7.76 (d, J = 3.95 Hz, 1H), 8.20 (t, J = 5.78 Hz, 1H), 8.73 (d, J = 1.90 Hz, 1H), 10.54 (s, 1H) | 418 |
| 282 | 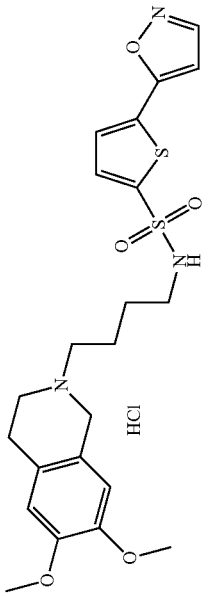 | 5-Isoxazol-5-yl-thiophene-2-sulfonic acid [4-(6,7-dimethoxy-3,4-dihydro-1H-isoquinolin-2-yl)-butyl]-amide hydrochloride | | 478 |
| 283 | 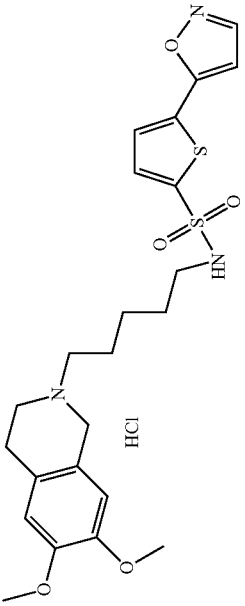 | 5-Isoxazol-5-yl-thiophene-2-sulfonic acid [5-(6,7-dimethoxy-3,4-dihydro-1H-isoquinolin-2-yl)-pentyl]-amide hydrochloride | | 492 |

| N° | STRUCTURE | Autonom | ¹H-NMR | MS (APCI) (M + H)⁺ |
|---|---|---|---|---|
| 284 | 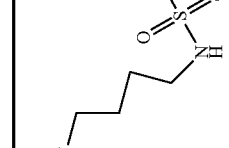 | 5-Isoxazol-5-yl-thiophene-2-sulfonic acid [4-(7-nitro-3,4-dihydro-1H-isoquinolin-2-yl)-butyl]-amide hydrochloride | | 463 |
| 285 | 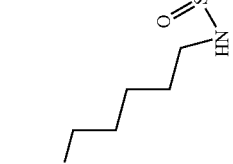 | 5-Isoxazol-5-yl-thiophene-2-sulfonic acid [5-(7-nitro-3,4-dihydro-1H-isoquinolin-2-yl)-pentyl]-amide hydrochloride | | 477 |
| 286 | 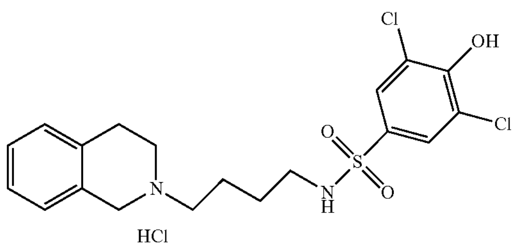 | 3,5-Dichloro-N-[4-(3,4-dihydro-1H-isoquinolin-2-yl)-butyl]-4-hydroxy-benzenesulfonamide hydrochloride | | 429 |
| 287 | 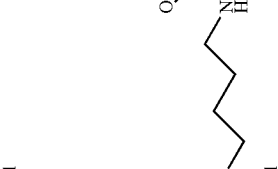 | 3,5-Dichloro-N-[4-(3,4-dihydro-1H-isoquinolin-2-yl)-butyl]-2-hydroxy-benzenesulfonamide hydrochloride | | 429 |

-continued

| N° | STRUCTURE | Autonom | ¹H-NMR | MS (APCI) (M + H)⁺ |
|---|---|---|---|---|
| 288 | 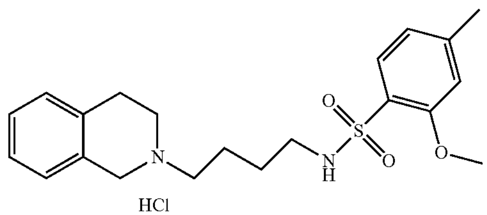 | N-[4-(3,4-Dihydro-1H-isoquinolin-2-yl)-butyl]-2-methoxy-4-methyl-benzenesulfonamide hydrochloride | | 389 |
| 289 | 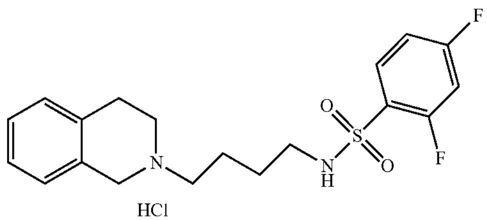 | N-[4-(3,4-Dihydro-1H-isoquinolin-2-yl)-butyl]-2,4-difluoro-benzenesulfonamide hydrochloride | | 381 |
| 290 | 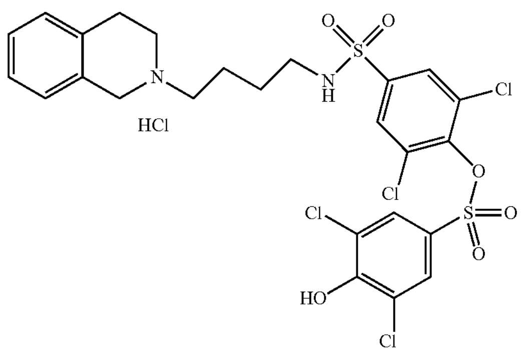 | 3,5-Dichloro-4-hydroxy-benzenesulfonic acid 2,6-dichloro-4-[4-(3,4-dihydro-1H-isoquinolin-2-yl)-butylsulfamoyl]-phenyl ester hydrochloride | | 653 |

| N° | STRUCTURE | Autonom | ¹H-NMR | MS (APCI) (M + H)⁺ |
|---|---|---|---|---|
| 291 | 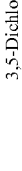 | 3,5-Dichloro-2-hydroxy-benzenesulfonic acid 2,4-dichloro-6-[4-(3,4-dihydro-1H-isoquinolin-2-yl)-butylsulfamoyl]-phenyl ester hydrochloride | | 653 |
| 292 | 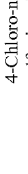 | 4-Chloro-naphthalene-1-sulfonic acid [4-(3,4-dihydro-1H-isoquinolin-2-yl)-butyl]-amide hydrochloride | | 429 |
| 293 | 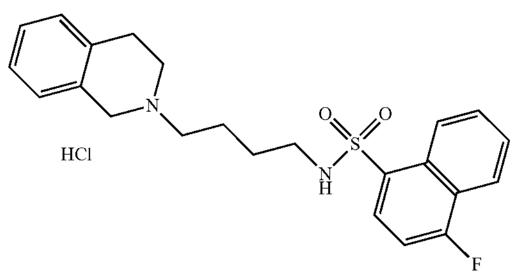 | 4-Fluoro-naphthalene-1-sulfonic acid [4-(3,4-dihydro-1H-isoquinolin-2-yl)-butyl]-amide hydrochloride | | 413 |

-continued

| N° | STRUCTURE | Autonom | ¹H-NMR | MS (APCI) (M + H)⁺ |
|---|---|---|---|---|
| 294 | 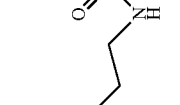 HCl | Dibenzofuran-2-sulfonic acid [4-(3,4-dihydro-1H-isoquinolin-2-yl)-butyl]-amide hydrochloride | | 435 |
| 295 |  HCl | 2,3-Dihydro-benzofuran-5-sulfonic acid [4-(3,4-dihydro-1H-isoquinolin-2-yl)-butyl]-amide hydrochloride | | 387 |
| 296 |  HCl | Biphenyl-2-sulfonic acid [4-(3,4-dihydro-1H-isoquinolin-2-yl)-butyl]-amide hydrochloride | | 421 |
| 297 | 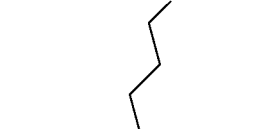 HCl | 1,2-Dimethyl-1H-imidazole-4-sulfonic acid [4-(3,4-dihydro-1H-isoquinolin-2-yl)-butyl]-amide hydrochloride | | 363 |

-continued

| N° | STRUCTURE | Autonom | ¹H-NMR | MS (APCI) (M + H)⁺ |
|---|---|---|---|---|
| 298 | 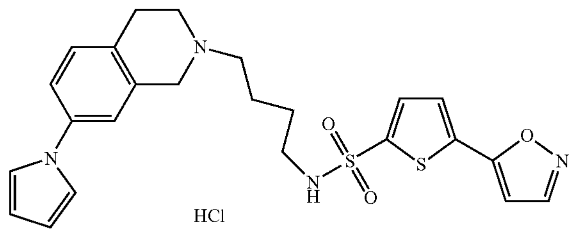 | 5-Isoxazol-5-yl-thiophene-2-sulfonic acid [4-(7-pyrrol-1-yl-3,4-dihydro-1H-isoquinolin-2-yl)-butyl]-amide hydrochloride | | 483 |
| 299 | 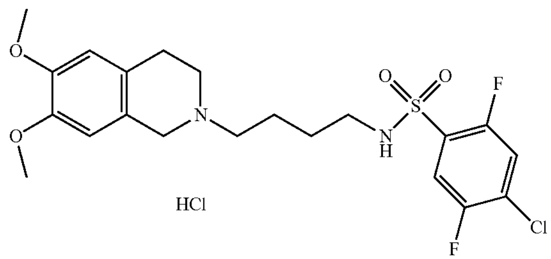 | 4-Chloro-N-[4-(6,7-dimethoxy-3,4-dihydro-1H-isoquinolin-2-yl)-butyl]-2-5-difluoro-benzenesulfonamide hydrochloride | | 475 |
| 300 | 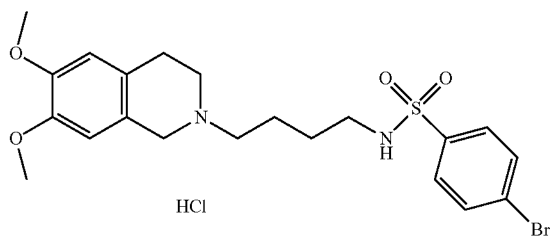 | 4-Bromo-N-[4-(6,7-dimethoxy-3,4-dihydro-1H-isoquinolin-2-yl)-butyl]-benzenesulfonamide hydrochloride | | 483 |
| 301 | 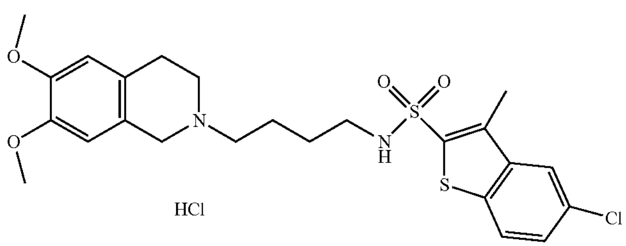 | 5-Chloro-3-methyl-benzo[b]thiophene-2-sulfonic acid [4-(6,7-dimethoxy-3,4-dihydro-1H-isoquinolin-2-yl)-butyl]-amide hydrochloride | | 509 |

| N° | STRUCTURE | Autonom | ¹H-NMR | MS (APCI) (M + H)⁺ |
|---|---|---|---|---|
| 302 | 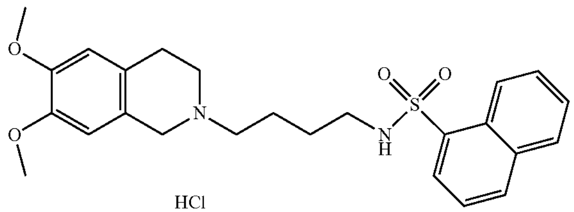 | Naphthalene-1-sulfonic acid [4-(6,7-dimethoxy-3,4-dihydro-1H-isoquinolin-2-yl)-butyl]-amide hydrochloride | | 455 |
| 303 | 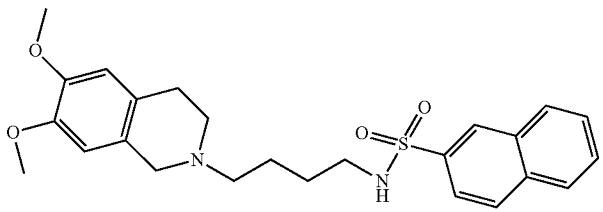 | Naphthalene-2-sulfonic acid [4-(6,7-dimethoxy-3,4-dihydro-1H-isoquinolin-2-yl)-butyl]-amide hydrochloride | | 455 |
| 304 | 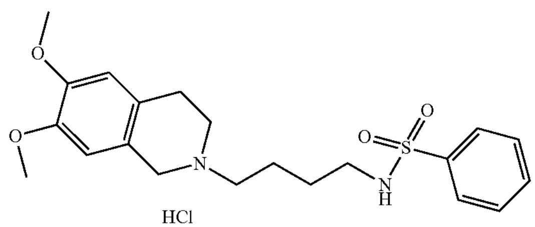 | N-[4-(6,7-Dimethoxy-3,4-dihydro-1H-isoquinolin-2-yl)-butyl]-benzenesulfonamide hydrochloride | | 405 |
| 305 | 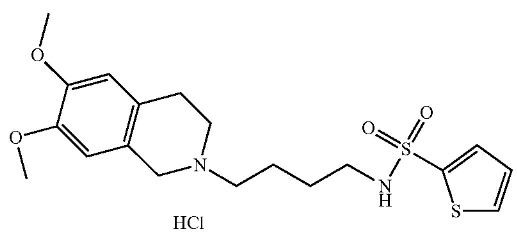 | Thiophene-2-sulfonic acid [4-(6,7-dimethoxy-3,4-dihydro-1H-isoquinolin-2-yl)-butyl]-amide hydrochloride | | 411 |

| N° | STRUCTURE | Autonom | ¹H-NMR | MS (APCI) (M + H)⁺ |
|---|---|---|---|---|
| 306 | 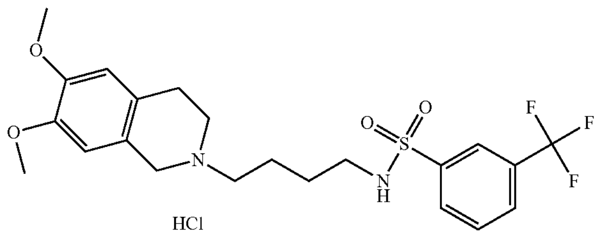 | N-[4-(6,7-Dimethoxy-3,4-dihydro-1H-isoquinolin-2-yl)-butyl]-3-trifluoromethyl-benzenesulfonamide hydrochloride | | 473 |
| 307 | 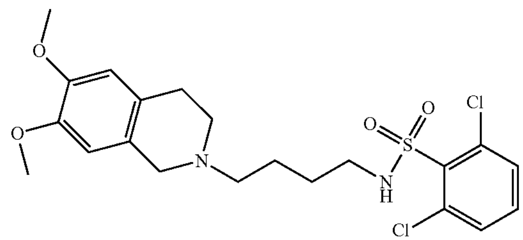 | 2,6-Dichloro-N-[4-(6,7-dimethoxy-3,4-dihydro-1H-isoquinolin-2-yl)-butyl]-benzenesulfonamide | | 473 |
| 308 | 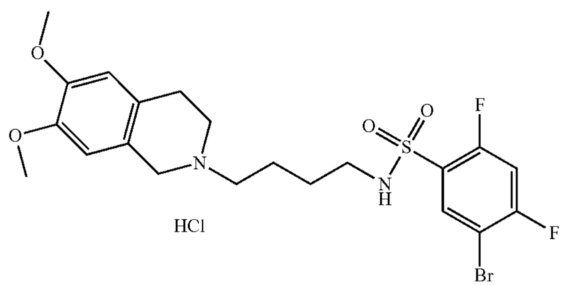 | 5-Bromo-N-[4-(6,7-dimethoxy-3,4-dihydro-1H-isoquinolin-2-yl)-butyl]-2,4-difluoro-benzenesulfonamide hydrochloride | | 519 |
| 309 | 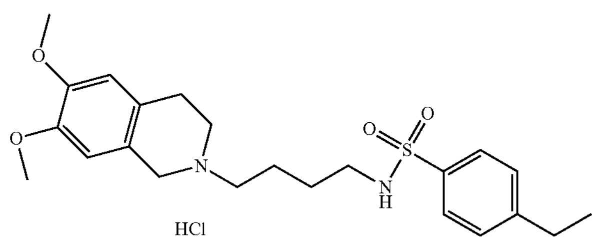 | N-[4-(6,7-Dimethoxy-3,4-dihydro-1H-isoquinolin-2-yl)-butyl]-4-ethyl-benzenesulfonamide hydrochloride | | 433 |

| N° | STRUCTURE | Autonom | ¹H-NMR | MS (APCI) (M + H)⁺ |
|---|---|---|---|---|
| 310 |  HCl | N-[4-(6,7-Dimethoxy-3,4-dihydro-1H-isoquinolin-2-yl)-butyl]-2-methoxy-4-methyl-benzenesulfonamide hydrochloride | | 449 |
| 311 |  HCl | N-[4-(6,7-Dimethoxy-3,4-dihydro-1H-isoquinolin-2-yl)-butyl]-4-methoxy-benzenesulfonamide hydrochloride | | 435 |
| 312 |  HCl | 1-Methyl-1H-imidazole-4-sulfonic acid [4-(6,7-dimethoxy-3,4-dihydro-1H-isoquinolin-2-yl)-butyl]-amide hydrochloride | | 409 |
| 313 |  HCl | Benzo[b]thiophene-2-sulfonic acid [4-(6,7-dimethoxy-3,4-dihydro-1H-isoquinolin-2-yl)-butyl]-amide hydrochloride | | 461 |

-continued

| N° | STRUCTURE | Autonom | ¹H-NMR | MS (APCI) (M + H)⁺ |
|---|---|---|---|---|
| 314 | 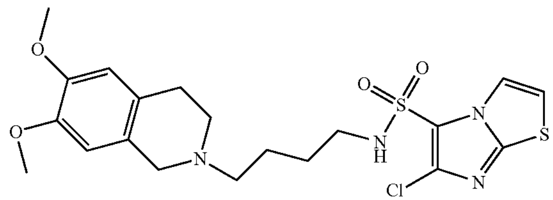 | 6-Chloro-imidazo[2,1-b]thiazole-5-sulfonic acid [4-(6,7-dimethoxy-3,4-dihydro-1H-isoquinolin-2-yl)-butyl]-amide hydrochloride | | 485 |
| 315 | 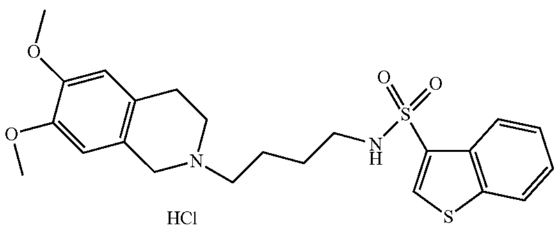 | Benzo[b]thiophene-3-sulfonic acid [4-(6,7-dimethoxy-3,4-dihydro-1H-isoquinolin-2-yl)-butyl]-amide hydrochloride | | 461 |
| 316 | 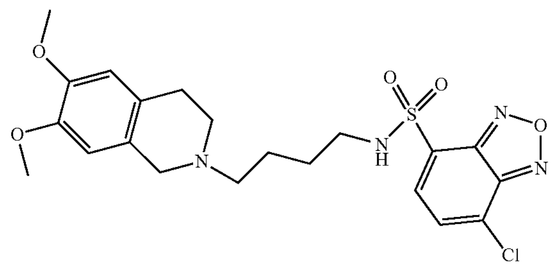 | 7-Chloro-benzo[1,2,5]oxadiazole-4-sulfonic acid [4-(6,7-dimethoxy-3,4-dihydro-1H-isoquinolin-2-yl)-butyl]-amide | | 481 |
| 317 | 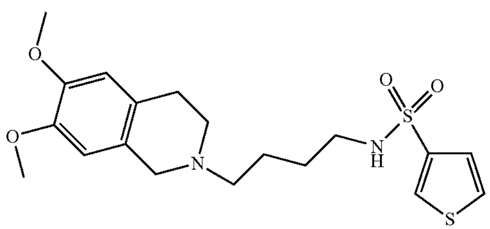 | Thiophene-3-sulfonic acid [4-(6,7-dimethoxy-3,4-dihydro-1H-isoquinolin-2-yl)-butyl]-amide | | 411 |

| N° | STRUCTURE | Autonom | ¹H-NMR | MS (APCI) (M + H)⁺ |
|---|---|---|---|---|
| 318 | 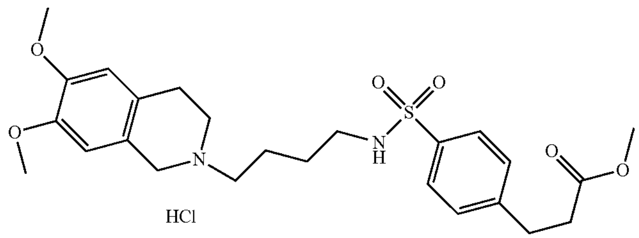 | 3-[4-[4-(6,7-Dimethoxy-3,4-dihydro-1H-isoquinolin-2-yl)-butylsulfamoyl]-phenyl]-propionic acid methyl ester hydrochloride | | 491 |
| 319 | 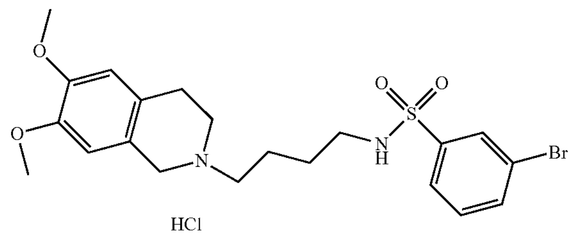 | 3-Bromo-N-[4-(6,7-dimethoxy-3,4-dihydro-1H-isoquinolin-2-yl)-butyl]-benzenesulfonamide hydrochloride | | 483 |
| 320 | 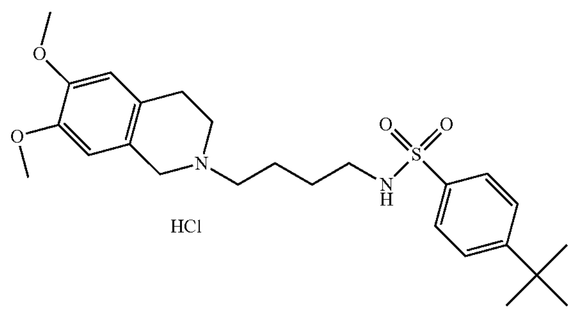 | 4-tert-Butyl-N-[4-(6,7-dimethoxy-3,4-dihydro-1H-isoquinolin-2-yl)-butyl]-benzenesulfonamide hydrochloride | | 461 |

| N° | STRUCTURE | Autonom | ¹H-NMR | MS (APCI) (M + H)⁺ |
|---|---|---|---|---|
| 321 | 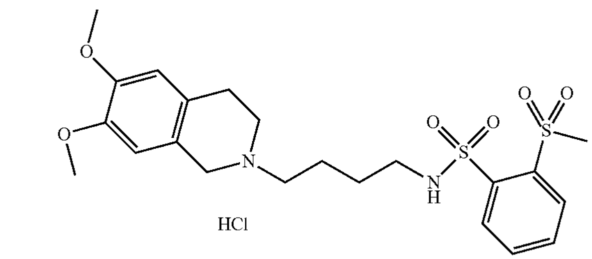 | N-[4-(6,7-Dimethoxy-3,4-dihydro-1H-isoquinolin-2-yl)-butyl]-2-methanesulfonyl-benzenesulfonamide hydrochloride | | 483 |
| 322 | 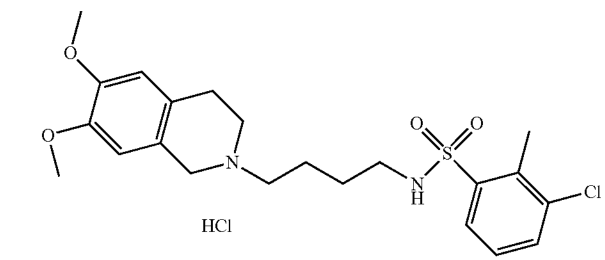 | 3-Chloro-N-[4-(6,7-dimethoxy-3,4-dihydro-1H-isoquinolin-2-yl)-butyl]-2-methyl-benzenesulfonamide hydrochloride | | 453 |
| 323 | 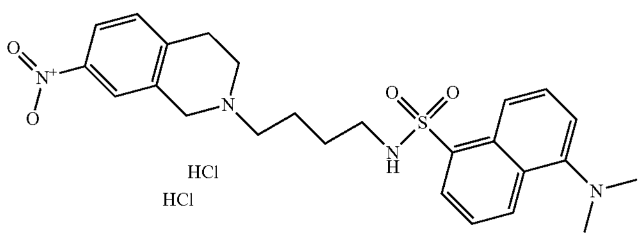 | 5-Dimethylamino-naphthalene-1-sulfonic acid [4-(7-nitro-3,4-dihydro-1H-isoquinolin-2-yl)-butyl]-amide hydrochloride | | 483 |
| 324 | 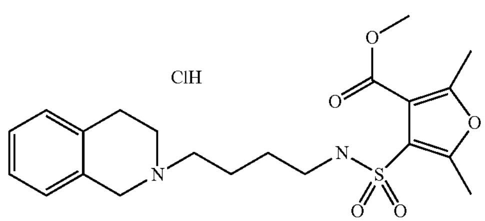 | 4-[4-(3,4-Dihydro-1H-isoquinolin-2-yl)-butyl sulfamoyl]-2,5-dimethyl-furan-3-carboxylic acid methyl ester hydrochloride | | 421 |

-continued

| N° | STRUCTURE | Autonom | ¹H-NMR | MS (APCI) (M + H)⁺ |
|---|---|---|---|---|
| 325 | ClH | 2-Oxo-2,3-dihydro-benzothiazole-6-sulfonic acid [4-(3,4-dihydro-1H-isoquinolin-2-yl)-butyl]-amide hydrochloride | | 418 |
| 326 | ClH | N-[4-(3,4-Dihydro-1H-isoquinolin-2-yl)-butyl]-4-fluoro-3-methyl-benzene-sulfonamide hydrochloride | | 377 |
| 327 | ClH | 2-Oxo-2,3-dihydro-benzooxazole-6-sulfonic acid [4-(3,4-dihydro-1H-isoquinolin-2-yl)-butyl]-amide hydrochloride | | 402 |
| 328 | ClH | 4-Cyclohexyl-N-[4-(3,4-dihydro-1H-isoquinolin-2-yl)-butyl]-benzenesulfonamide hydrochloride | | 427 |

-continued

| N° | STRUCTURE | Autonom | ¹H-NMR | MS (APCI) (M + H)⁺ |
|---|---|---|---|---|
| 329 | 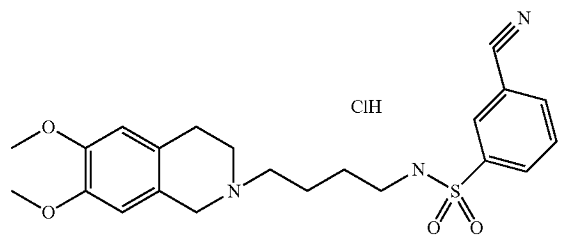 | 3-Cyano-N-[4-(6,7-dimethoxy-3,4-dihydro-1H-isoquinolin-2-yl)-butyl]-benzenesulfonamide hydrochloride | | 430 |
| 330 | 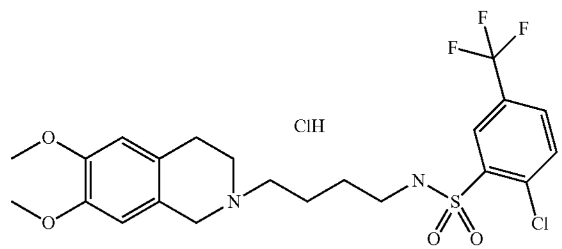 | 2-Chloro-N-[4-(6,7-dimethoxy-3,4-dihydro-1H-isoquinolin-2-yl)-butyl]-5-trifluoromethyl-benzenesulfonamide hydrochloride | | 507 |
| 331 | 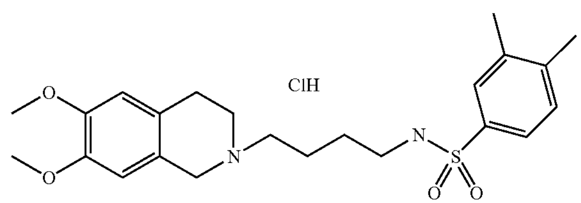 | N-[4-(6,7-Dimethoxy-3,4-dihydro-1H-isoquinolin-2-yl)-butyl]-3,4-dimethyl-benzenesulfonamide hydrochloride | | 433 |
| 332 | 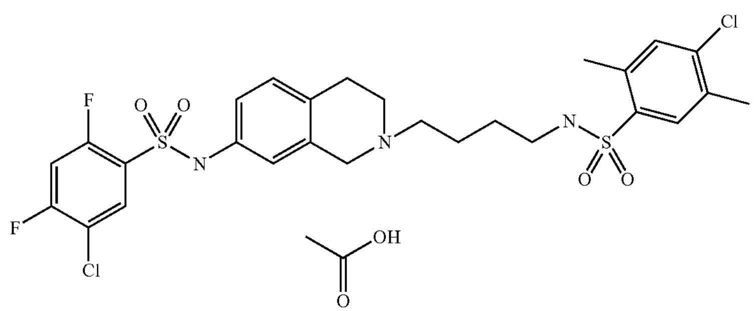 | | | 632 |

| N° | STRUCTURE | Autonom | ¹H-NMR | MS (APCI) (M + H)⁺ |
|---|---|---|---|---|
| 333 | 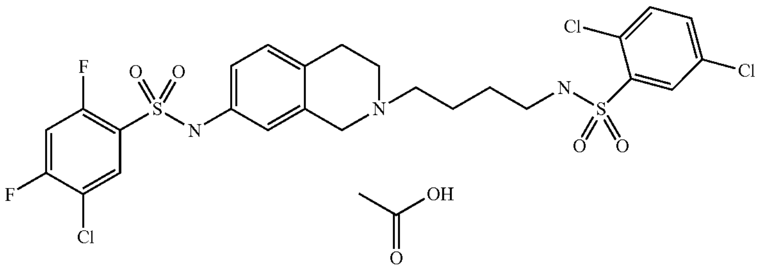 | | | 638 |
| 334 | 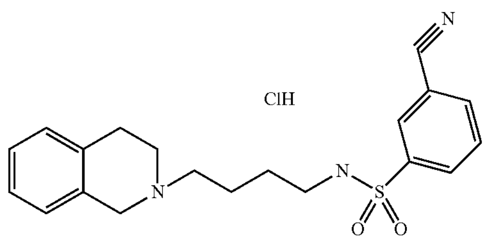 | 3-Cyano-N-[4-(3,4-dihydro-1H-isoquinolin-2-yl)-butyl]-benzenesulfonamide hydrochloride | | 370 |
| 335 | 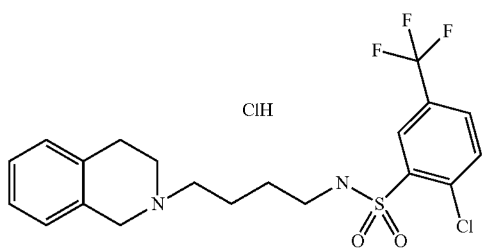 | 2-Chloro-N-[4-(3,4-dihydro-1H-isoquinolin-2-yl)-butyl]-5-trifluoromethyl-benzenesulfonamide hydrochloride | | 447 |
| 336 | 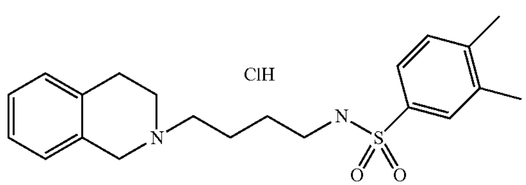 | N-[4-(3,4-Dihydro-1H-isoquinolin-2-yl)-butyl]-3,4-dimethyl-benzenesulfonamide hydrochloride | | 373 |

-continued
| N° | STRUCTURE | Autonom | ¹H-NMR | MS (APCI) (M + H)⁺ |
|---|---|---|---|---|
| 337 | 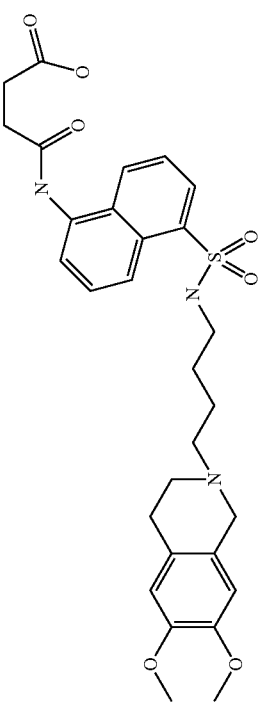 | N-{5-[4-(6,7-Dimethoxy-3,4-dihydro-1H-isoquinolin-2-yl)-butylsulfamoyl]-naphthalen-1-yl}-succinamic acid | | 570 |
| 338 | 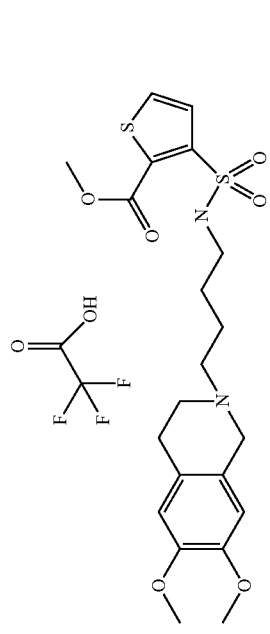 | 3-[4-(6,7-Dimethoxy-3,4-dihydro-1H-isoquinolin-2-yl)-butylsulfamoyl]-thiophene-2-carboxylic acid methyl ester trifluoroacetate | | 469 |

BIOLOGICAL ASSAYS

Radioligand Binding

Radioligand binding assays were performed using the Cloned Human Serotonin Receptor, Subtype 7 (h5HT$_7$), expressed in CHO cells, coated on Flashplate (Basic FlashPlate Cat.: SMP200) from PerkinElmer (Cat.: 6120512). The protocol assay was essentially the recommended protocol in the Technical Data Sheet by PerkinEmer Life and Analytical Sciences. The Mass membrane protein/well was typically 12 μg and the Receptor/well was about 9-10 fmoles. The Flashplate were let equilibrate at room temperature for one hour before the addition of the components of the assay mixture. The binding buffer was: 50 mM Tris-HCl, pH 7.4, containing 10 mM MgCl$_2$, 0.5 mM EDTA and 0.5% BSA. The radioligand was [$^{125}$I]LSD at a final concentration of 0.82 nM. Nonspecific binding was determined with 50 μM of Clozapine. The assay volume was 25 μl. TopSeal-A were applied onto Flashplate microplates and they were incubated at room temperature for 240 minutes in darkness. The radioactivity were quantified by liquid scintillation spectrophotometry (Wallac 1450 Microbeta Trilux) with a count delay of 4 minutes prior to counting and a counting time of 30 seconds per well. Competition binding data were analyzed by using the LIGAND program (Munson and Rodbard, LIGAND: A versatile, computerized approach for characterization of ligand-binding systems. *Anal. Biochem.* 107: 220-239, 1980) and assays were performed in triplicate determinations for each point. Results for representative compounds are given in the table 2 below:

TABLE 2

| COMPOUND | 5-HT7 IC-50 (nM) |
|---|---|
| 2 | 59.2 |
| 5 | 33.2 |
| 116 | 31.1 |
| 118 | 39.2 |
| 140 | 60.8 |
| 142 | 80.4 |
| 151 | 39 |
| 160 | 74.4 |
| 210 | 37.3 |
| 220 | 67.4 |
| 235 | 68.4 |
| 257 | 57.2 |

The invention claimed is:

1. A method for treating a central nervous disorder comprising administering to a patient in need thereof a therapeutically effective amount of the compound of formula (I)

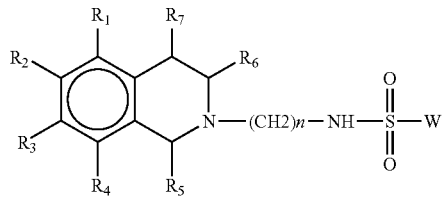

(I)

wherein

W is substituted or unsubstituted alkyl, substituted or unsubstituted alkenyl, substituted or unsubstituted cycloalkyl, substituted or unsubstituted aryl, substituted or unsubstituted heterocyclyl;

$R_1$, $R_2$, $R_3$, $R_4$, $R_5$, $R_6$ and $R_7$ are each independently selected from the group formed by hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR$_8$, —C(O)OR$_8$, —C(O)NR$_8$R$_9$—C═NR$_8$, —CN, —OR$_8$, —OC(O)R$_8$, —S(O)$_t$—R$_8$, —NR$_8$R$_9$, —NR$_8$C(O)R$_9$, —NO2, —N═CR$_8$R$_9$ or halogen, wherein t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen;

n is 4, 5 or 6;

or a pharmaceutically acceptable salt or isomer thereof, wherein the central nervous disorder is sleep disorder, shift worker syndrome, jet lag, depression, seasonal affective disorder, migraine, anxiety, psychosis, schizophrenia, pain, cognition and memory disorders, neuronal degeneration resulting from ischemic events, cardiovascular diseases, irritable bowel syndrome, inflammatory bowel disease, spastic colon or urinary incontinence.

2. The method of claim 1, wherein n is 4 or 5.

3. The method of claim 2, wherein n is 4.

4. The method of claim 1, wherein W is an aromatic group and is substituted or unsubstituted aryl or substituted or unsubstituted heterocyclyl.

5. The method of claim 4, wherein W is substituted or unsubstituted phenyl.

6. The method of claim 1, wherein W is selected from alkyl-substituted, alkoxy-substituted and/or halo-substituted phenyl.

7. The method of claim 1, wherein $R_5$, $R_6$ and $R_7$ are each H.

8. The method of claim 1, wherein $R_1$ and $R_4$ are each H.

9. The method of claim 1, wherein $R_2$ and $R_3$ are each alkoxy.

10. The method of claim 9, wherein $R_2$ and $R_3$ are each methoxy.

* * * * *